US010301623B2

(12) United States Patent
Allen et al.

(10) Patent No.: US 10,301,623 B2
(45) Date of Patent: May 28, 2019

(54) PHASED SMALL RNAS

(71) Applicant: Monsanto Technology LLC, St. Louis, MO (US)

(72) Inventors: Edwards Allen, O'Fallon, MO (US); Liang Guo, St. Louis, MO (US); Sara E. Heisel, St. Louis, MO (US); Sergey I. Ivashuta, Ballwin, MO (US); Yuanji Zhang, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 155 days.

(21) Appl. No.: 15/052,062

(22) Filed: Feb. 24, 2016

(65) Prior Publication Data

US 2016/0168569 A1 Jun. 16, 2016

Related U.S. Application Data

(63) Continuation of application No. 13/775,477, filed on Feb. 25, 2013, now Pat. No. 9,309,512, which is a continuation of application No. 11/897,611, filed on Aug. 31, 2007, now Pat. No. 8,404,928.

(60) Provisional application No. 60/841,608, filed on Aug. 31, 2006.

(51) Int. Cl.
*C12N 15/82* (2006.01)
*C12N 15/113* (2010.01)

(52) U.S. Cl.
CPC .......... *C12N 15/113* (2013.01); *C12N 15/827* (2013.01); *C12N 15/8218* (2013.01); *C12N 15/8245* (2013.01); *C12N 15/8254* (2013.01); *C12N 15/8266* (2013.01)

(58) Field of Classification Search
CPC .................................................... C12N 15/113
USPC .......................................................... 800/285
See application file for complete search history.

(56) References Cited

U.S. PATENT DOCUMENTS 5,004,863 A 4/1991 Umbeck
5,015,580 A 5/1991 Christou et al.
5,107,065 A 4/1992 Shewmaker et al.
5,159,135 A 10/1992 Umbeck
5,190,931 A 3/1993 Inouye
5,208,149 A 5/1993 Inouye
5,272,065 A 12/1993 Inouye et al.
5,416,011 A 5/1995 Hinchee et al.
5,453,566 A 9/1995 Shewmaker et al.
5,463,174 A 10/1995 Moloney et al.
5,500,365 A 3/1996 Fischhoff et al.
5,518,908 A 5/1996 Corbin et al.
5,538,880 A 7/1996 Lundquist et al.
5,550,318 A 8/1996 Adams et al.
5,569,834 A 10/1996 Hinchee et al.
5,591,616 A 1/1997 Hiei et al.
5,633,435 A 5/1997 Barry et al.
5,750,848 A 5/1998 Krüger et al.
5,750,871 A 5/1998 Moloney et al.
5,759,829 A 6/1998 Shewmaker et al.
5,763,245 A 6/1998 Greenplate et al.
5,780,708 A 7/1998 Lundquist et al.
5,824,877 A 10/1998 Hinchee et al.
5,846,797 A 12/1998 Strickland
5,888,732 A 3/1999 Hartley et al.
5,914,451 A 6/1999 Martinell et al.
5,981,840 A 11/1999 Zhao et al.
6,118,047 A 9/2000 Anderson et al.
6,153,812 A 11/2000 Fly et al.
6,160,208 A 12/2000 Lundquist et al.
6,194,636 B1 2/2001 McElroy et al.
6,207,879 B1 3/2001 McElroy et al.
6,232,526 B1 5/2001 McElroy et al.
6,277,608 B1 8/2001 Hartley et al.
6,288,312 B1 9/2001 Christou et al.
6,372,965 B1 4/2002 Lightner et al.
6,384,301 B1 5/2002 Martinell et al.
6,399,861 B1 6/2002 Anderson et al.
6,403,865 B1 6/2002 Koziel et al.
6,426,446 B1 7/2002 McElroy et al.
6,426,448 B1 7/2002 Booth, Jr. et al.
6,429,357 B1 8/2002 McElroy et al.
6,433,252 B1 8/2002 Kriz et al.
6,437,217 B1 8/2002 McElroy et al.
6,583,338 B2 6/2003 McElroy et al.
6,624,344 B1 9/2003 Rangan et al.
6,759,575 B2 7/2004 Michiels et al.
6,872,872 B1 3/2005 Lightner et al.
7,002,058 B2 2/2006 Martinell et al.
(Continued)

FOREIGN PATENT DOCUMENTS

CN 101600798 A 12/2009
WO WO 95/06128 A2 3/1995
(Continued)

OTHER PUBLICATIONS

Fusaro et al. 2006, EMBO 7:1168-1175.*
Allen et al., "Evolution of microRNA genes by inverted duplication of target gene sequences in *Arabidopsis thaliana," Nature Genetics,* 36(12):1282-1290 (2004).
Allen et al., "MicroRNA-Directed Phasing during Trans-Acting siRNA Biogenesis in Plants," *Cell,* 121:207-221 (2005).
Altschul et al., "Basic Local Alignment Search Tool," *J. Mol. Biol.,* 215:403-410 (1990).
Altschul et al., "Gapped BLAST and PSI-BLAST: a new generation of protein database search programs," *Nucleic Acids Res.,* 25(17):3389-3402 (1997).
(Continued)

*Primary Examiner* — Li Zheng
(74) *Attorney, Agent, or Firm* — Amanda Carmany-Rampey; David R. Marsh; Arnold & Porter Kaye Scholer LLP

(57) ABSTRACT

This invention discloses recombinant DNA constructs encoding phased small RNAs useful in regulating expression of one or more genes of interest. Also disclosed by this invention are transgenic plant cells, plants, and seeds containing a recombinant DNA construct of this invention.

4 Claims, 9 Drawing Sheets

Specification includes a Sequence Listing.

(56) References Cited

U.S. PATENT DOCUMENTS

| | | | | |
|---|---|---|---|---|
| 7,060,876 | B2 | 6/2006 | Hiei et al. | |
| 8,217,227 | B2 | 7/2012 | Allen et al. | |
| 2002/0133852 | A1 | 9/2002 | Hauge et al. | |
| 2003/0005491 | A1 | 1/2003 | Hauge et al. | |
| 2003/0049612 | A1 | 3/2003 | Echt et al. | |
| 2003/0150017 | A1* | 8/2003 | Mesa | C07K 14/4354 800/279 |
| 2003/0167537 | A1 | 9/2003 | Jiang | |
| 2004/0087030 | A1 | 5/2004 | Armstrong et al. | |
| 2004/0098761 | A1 | 5/2004 | Trick et al. | |
| 2004/0115642 | A1 | 6/2004 | Fu | |
| 2004/0126845 | A1 | 7/2004 | Eenennaam et al. | |
| 2004/0216189 | A1 | 10/2004 | Houmard et al. | |
| 2004/0231016 | A1 | 11/2004 | Wang et al. | |
| 2004/0244075 | A1 | 12/2004 | Cai et al. | |
| 2005/0005321 | A1 | 1/2005 | Martinell et al. | |
| 2006/0021087 | A1 | 1/2006 | Baum et al. | |
| 2006/0200878 | A1 | 9/2006 | Lutfiyya et al. | |
| 2007/0079393 | A1 | 4/2007 | McCutchen et al. | |
| 2007/0300329 | A1 | 12/2007 | Allen et al. | |

FOREIGN PATENT DOCUMENTS

| | | | |
|---|---|---|---|
| WO | WO 95/06722 | A1 | 9/1995 |
| WO | WO 99/49029 | A1 | 9/1999 |
| WO | WO 99/53050 | A3 | 10/1999 |
| WO | WO 99/61631 | A1 | 12/1999 |
| WO | WO 02/057471 | A2 | 7/2002 |
| WO | WO 02/062129 | A2 | 8/2002 |
| WO | WO 03/077643 | A2 | 9/2003 |
| WO | WO 03/078629 | A1 | 9/2003 |
| WO | WO 2005/007829 | A2 | 1/2005 |
| WO | WO 2005/011816 | A2 | 2/2005 |
| WO | WO 2005/035769 | A2 | 4/2005 |
| WO | WO 2005/077116 | A2 | 8/2005 |
| WO | WO 2005/077117 | A2 | 8/2005 |
| WO | WO 2005/110068 | A2 | 11/2005 |
| WO | WO 2006/044322 | A2 | 4/2006 |
| WO | WO 2006/046148 | A2 | 5/2006 |
| WO | WO 2006/073727 | A2 | 7/2006 |
| WO | WO 2006/074400 | A2 | 7/2006 |
| WO | WO 2006/111512 | A1 | 10/2006 |
| WO | WO 2006/138638 | A1 | 12/2006 |
| WO | WO 2007/024207 | A1 | 3/2007 |
| WO | WO 2007/047016 | A2 | 4/2007 |
| WO | WO 2008/066206 | A1 | 6/2008 |

OTHER PUBLICATIONS

Ambros et al., "A uniform system for microRNA annotation," *RNA*, 9:277-279 (2003).

Aslanidis et al., "Ligation-independent cloning of PCR products (LIC-POR)," *Nucleic Acids Research,* 18(20):6069-6074 (1990).

Australian Examination Report, dated Jun. 5, 2012, in Australian Patent Application No. AU2007290367.

Australian Examination Report, dated May 2, 2013, in Australian Patent Application No. AU2007290367.

Australian Examination Reporter No. 1, dated Sep. 24, 2014, in Australian Patent Application No. 2013203734.

Bartel, "MicroRNAs: Genomics, Biogenesis, Mechanism, and Function," (2004) *Cell,* 116:281-297 (2004).

Becker et al., "Fertile transgenic wheat from microprojectile bombardment of scutellar tissue," *The Plant Journal,* 5(2):299-307 (1994).

Boutros et al., "Genome-Wide RNAi Analysis of Growth and Viability in *Drosophila* Cells," *Science,* 303:832-835 (2004).

Brodersen et al., "The diversity of RNA silencing pathways in plants," *Trends Genetics,* 22(5):268-280 (2006).

Butenko et al., Inflorescence Deficient in Abscission Controls Floral Organ Abscission in *Arabidopsis* and Identifies a Novel Family of Putative Ligands in Plants, *Plant Cell*, 15:2296-2307 (2003).

Bytebier et al., "T-DNA organization in tumor cultures and transgenic plants of the monocotyledon *Asparagus officinalis,*" *Proc. Natl. Acad. Sci. U.S.A.,* 84:5345-5349 (1987).

Chen et al., "Bioinformatic prediction and experimental validation of a microRNA-directed tandem trans-acting siRNA cascade in *Arabidopsis,*" *Proc. Natl. Acad. Sci. USA,* 104(9):3318-3323. (2007).

Chen et al., "Small RNAs in angiosperms: sequence characteristics,distribution and generation," *Bioinformatics,* 26(11):1391-1394 (2010).

Cheng et al., "Production of fertile transgenic peanut (*Arachis hypogaea* L.) plants using *Agrobacterium tumefaciens,*" *Plant Cell Reports,* 15:653-657 (1996).

Chinese Office Action Translation, dated Feb. 16, 2011, in Chinese Patent Application No. CN200780039293.2.

Chinese Office Action Translation, dated Mar. 1, 2012, in International Patent Application No. CN200780039293.2.

Chuang et al., "Specific and heritable genetic interference by double-stranded RNA in *Arabidopsis thaliana,*" *PNAS,* 97(9):4985-4990 (2000).

Clough et al., "Floral dip: a simplified method for Agrobacterium-mediated transformation of *Arabidopsis thaliana,*" *The Plant Journal,* 16(6):735-743 (1998).

Database EMBL [Online] Oct. 11, 2006 (Oct. 11, 2006) "*Oryza sativa* Japonica Group cDNA, clone: J075149B08, full insert sequence," XP002485853 retrieved from EBI accession No. EMBL:AK242131 Database accession No. AK242131.

Database EMBL [Online] Feb. 14, 2002 (Feb. 14, 2002), "*Oryza sativa* Japonica Group genomic DNA, chromosome 6, PAC clone:P0421H01," XP002485854 retrieved from EBI accession No. EMBL:AP004750 Database accession No. AP004750.

Database EMBL [Online] Feb. 3, 2006 (Feb. 3, 2006), "*Oryza sativa* Japonica Group cDNA, clone: J07B5056F19T3, 5'end of J075056F19." XP002485855 retrieved from EBI accession No. EMBL: C1682210 Database accession No. C1682210.

De Amicis et al., "Intercodon dincleotides affect codon choice in plant genes," *Nucleic Acid Research,* 28(17):3339-3346 (2000).

De Framond, "MINI-Ti: A New Vector Strategy for Plant Genetic Engineering," *Nature Biotechnology,* 1:262-269 (1983).

Di Giusto et al., "Construction, Stability, and Activity of Multivalent Circular Anticoagulant Aptamers," *J. Biol. Chem.,* 279(45):46483-46489 (2004).

Du et al., "A systematic analysis of the silencing effects of an active siRNA at all single-nucleotide mismatched target sites," *Nucleic Acids Research,* 33(5):1671-1677 (2005).

EPO Communication dated Dec. 14, 2011, in European Patent Application No. 07837683.7.

EPO Communication dated Jan. 21, 2013, in European Patent Application No. 07837683.7.

EPO Communication dated Jul. 23, 2009, in European Patent Application No. 07837683.7.

EPO Communication dated May 20, 2014, in European Patent Application No. 07837683.7.

EPO Communication dated Nov. 26, 2010, in European Patent Application No. 07837683.7.

Erdmann et al., "The non-coding RNAs as riboregulators," *Nucleic Acids Res.,*29(1):189-193 (2001).

Fu el al., "Quality assessment of maize assembled genomic islands (MAGIs) and large-scale experimental verification of predicted genes," (2005) *Proc. Natl. Acad. Sci. USA,* 102:12282-12287 (2005).

Fusaro et al., "RNA interference-inducing hairpin RNAs in plants act through the viral defence pathway," *EMBO* Rep 7: 1168-1175 (2006).

Genbank accession No. X70153, nucleotides 848-1259.

Gendel, "Sequence databases for assessing the potential allergenicity of proteins used in transgenic foods," *Advances in Food and Nutrition Research,* 42:63-92 (1998).

Gene silencing in plants, *The Plant Journal,* 27(6):581-590 (2001).

Gottesman, "Micros for microbes: non-coding regulatory RNAs in bacteria," *Trends Genet.,* 21(7):399-404 (2005).

Griffiths-Jones et al., "Rfam: annotating non-coding RNAs in complete genomes," *Nucleic Acids Res.,* 33:121-124 (2005).

Hartings et al., "The b-32 protein from maize endosperm: characterization of genomic sequences encoding two alternative central domains," *Plant Mol. Biol.,* 14:1031-1040 (1990).

(56) References Cited

OTHER PUBLICATIONS

Heisel et al., "Characterization of Unique Small RNA Populations from Rice Grain," *Plos One,* 3(8):e2871 (2008).
Helliwell et al., "High-throughput vectors for efficient gene silencing in plants," *Funct. Plant Biol.,* 29:1217-1225 (2002).
Hoekema et al., "A binary plant vector strategy based on separation of vir- and Tregion of the *Agrobacterium tumefaciens* Ti-plasmid," *Nature,* 303:179-180 (1983).
Howell et al., "Genome-Wide Analysis of the RNA-Dependent RNA Polymerase6/Dicer-Like4 Pathway in *Arabidopsis* Reveals Dependency on miRNA- and tasiRNA-Directed Targeting," *Plant Cell,* 19:926-942 (2007).
International Preliminary Report on Patentability, dated Mar. 23, 2012, in International Patent Application No. PCTUS2007019283.
International Search Report and Written Opinion, dated Jul. 15, 2008, in International Patent Application No. PCTUS2007019283.
International Search Report, dated Jul. 15, 2008, in International Patent Application No. PCT/US2007/019283.
Johnson et al., "Clusters and superclusters of phased small RNAs in the developing inflorescence of rice," *Genome Res.,* 19:1429-1440 (2009).
Jones-Rhoades et al., "MicroRNAs and Their Regulatory Roles in Plants," *Annu. Rev. Plant Biol.,* 57:19-53 (2006).
Kasschau et al., "P1/HC-Pro, a Viral Suppressor of RNA Silencing, Interferes with *Arabidopsis* Development and miRNA Function," *Dev. Cell,* 4:205-217 (2003).
Khvorova et al., "Functional siRNAs and miRNAs Exhibit Strand Bias," *Cell,* 115:209-216 (2003).
Kim, "MicroRNA Biogenesis: Coordinated Cropping and Dicing," *Nature Reviews Molecular Cell Biology,* 6:376-385 (2005).
Kurihara et al., "*Arabidopsis* micro-RNA biogenesis through Dicer-like 1 protein functions," *Proc. Natl. Acad. Sci. U. S. A.,* 101(34):12753-12758 (2004).
Lee et al., "MicroRNA maturation: stepwise processing and subcellular localization," *EMBO Journal,* 21(17):4663-4670 (2002).
Llave et al., "Cleavage of Scarecrow-like mRNA Targets Directed by a Class of *Arabidopsis* miRNA," *Science,* 297:2053-2056 (2002).
Lund et al., "Nuclear Export of MicroRNA Precursors," *Science,* 303:95-98 (2004).
Mallory et al., "MicroRNA control of Phabulosa in leaf development: importance of pairing to the microRNA 5' region," *EMBO Journal,* 23:3356-3364 (2004).
Margulies et al., "Genome sequencing in microfabricated high-density picolitre reactors," *Nature,* 437:376-380 (2005).
Marks et al., "Trichome Development in *Arabidopsis thaliana.* I. T-DNA Tagging of the Glabrous1 Gene," *Plant Cell,* 1:1043-1050 (1989).
Masoud et al., "Constitutive expression of an inducible β-1,3-glucanase in alfalfa reduces disease severity caused by the oomycete pathogen *Phytophthora megasperma* f. sp *medicaginis,* but does not reduce disease severity of chitincontaining fungi," *Transgenic Research,* 5:313-323 (1996).
Millar et al., "Plant and animal microRNAs: similarities and differences," *Funct. Integr Genomics,* 5:129-135 (2005).
Molnar et al., "miRNAs control gene expressio in the single-cell alga *Chlamydomonas reinhardtii," Nature,* 447:1126-1129 (2007).
Notification of Reexamination dated Jun. 30, 2014, in Chinese Patent Application No. 200780039293.3.
Office Action, dated Dec. 14, 2011 in International Patent Application No. EP07837683.7.
Office Action, dated Jul. 23, 2009 in International Patent Application No. EP07837683.7.
Radke et al., "Transformation and regeneration of *Brassica rapa* using Agrobacterium tumefaciens," *Plant Cell Reports,* 11:499-505 (1992).
Rajagopalan et al., "A diverse and evolutionarily fluid set of microRNAs in *Arabidopsis thaliana," Genes & Dev.,* 20:3407-3425 (2006).
Rashtchian et al., "Uracil DNA Glycosylase-Mediated Cloning of Polymerase Chain Reaction-Amplified DNA: Application to Genomic and cDNA Cloning," *Analytical Biochemistry,* 206:91-97 (1992).
Reinhart et al., "MicroRNAs in plants," *Genes & Dev.,* 16:161611626 (2002).
Reynolds et al., Rational siRNA design for RNA interference, *Nature Biotechnol.,* 22(3):326-330 (2004).
Schwab et al., "Highly Specific Gene Silencing by Artificial MicroRNAs in *Arabidopsis," Plant Cell,* 18:1121-1133 (2006).
Siomi et al., "Expanding RNA physiology: microRNAs in a unicellular organism," *Genes & Dev.,* 21:1153-1156 (2007).
Smith et al., "Total Silencing by intron-spliced hairpin RNAs," *Nature,* 407:319-320 (2000).
Sleeves et al., "Transgenic soybeans expressing siRNAs specific to a major sperm protein gene suppress *Heterodera glycines* reproduction," *Funct. Plant Biol.,* 33:991-999 (2006).
Sun et al., "A Highly Efficient Transformation Protocol for Micro-Tom, a Model Cultivar for Tomato Functional Genomics," *Plant Cell Physiol.,* 47(3):426-431 (2006).
Tomari et al., "Perspective: machines for RNAi," *Genes & Dev.,* 19:517-529 (2005).
Toriyama et al., "Transgenic Rice Plants After Direct Gene Transfer Into Protoplasts,"*Bio/Technology,* 6:1072-1074 (1988).
Varsha et al., Construct design for ef® cient, effective and highthroughput.
Vasil et al., "Herbicide Resistant Fertile Transgenic Wheat Plants Obtained by Microprojectile Bombardment of Regenerable Embryogenic Callus," *Bio/Technology,* 10:667-674 (1992).
Vaucheret, "MicroRNA-Dependent Trans-Acting siRNA Production," *Sci. STKE,* 2005, 300:pe43 (2005).
Wan et al., "Generation of Large Numbers of Independently Transformed Fertile Barley Plants," *Plant Physiol.,* 104:37-48 (1994).
Waterhouse et al., "Virus resistance and gene silencing in plants can be induced by simultaneous expression of sense and antisense RNA," *Proc. Natl. Acad. Sci. USA,* 95:13959-13964 (1998).
Wesley et al., "Construct design for efficient, effective and high-throughput gene silencing in plants," *Plant J.,* 27(6):581-590 (2001).
Written Opinion of the International Searching Authority, dated Jul. 15, 2008, in International Patent Application No. PCT/US2007/019283.
Xie et al., "Dicer-Like 4 functions in trans-acting small interfering RNA biogenesis and vegetative phase change in *Arbidopsis thaliana," PNAS* 102:12984-12989 (2005).
Yoshikawa et al., "A pathway for the biogenesis of trans-acting siRNAs in *Arabidopsis," Genes Dev.,* 19:2164-2175 (2005).
Zhang et al., "DEG: a database of essential genes," *Nucleic Acids Research,* 32:D271-D272 (2004).
Zhang et al., "Transgenic rice plants produced by electroporation-mediated plasmid uptake into protoplasts," *Plant Cell Rep.,* 7:379-384 (1988).
Zhao et al., "A complex system of small RNAs in the unicellular green alga *Chlamydomonas reinhardtii," Genes & Dev.,* 21: 1190-1203 (2007).
Zhu et al., "A diverse set of microRNAs and microRNA-like small RNAs in developing rice grains," Genome Res., 18:1456-1465 (2008).
European Search Report dated Dec. 12, 2017 in European Patent Application No. 171942816.
Patent Examination Report No. 1 dated Sep. 24, 2014 in Australian Patent Application No. 2013203734.
Patent Examination Report No. 2 dated Dec. 23, 2015 in Australian Patent Application No. 2013203734.
Patent Examination Report No. 3 dated Jun. 24, 2016 in Australian Patent Application No. 2013203734.
European Office Action dated Feb. 9, 2015 in European Patent Application No. 078376837.
European Office Action dated Aug. 29, 2016 in European Patent Application No. 078376837.
European Office Action dated Apr. 10, 2017 in European Patent Application No. 078376837.

(56) References Cited

OTHER PUBLICATIONS

Decision to Grant dated Sep. 7, 2017 is European Patent Application No. 078376837.

* cited by examiner

FIGURE 2 aaaatttctaccatctcactttgtaataataccataaatgctttgccatatgtaaaaccgttcgagtagcgacaacaccggttctataaaagttgttccctttccacgta
cttataagcttatctagtgtgcacgcattccctttccacgtatttccacgtatttccattaaccttatcttgtgtgcacgcataaggtacatgggtaataacatgttcttgga
agtggtccttacctacaccgc*tatataaa*gcgacgcctctcattgcgacaccaccAATCTTATTCTACATATTTCTATCTTATATAGAAC
AACTAGCATAGCTCTCGTTGCCCAGCCAGGTTGCCCAGCCAGGTTGCCTGGTGCACAATGAGAGCTGGCT
AGGGCGGACTCATTCTGCTGTTGGTGCCCAACGATGCTAGCTGCTACTCATACTAGTGAAGCCTGCCATGG
TTCTGAGAAATTTTTGGATACTCCGCTGCGTAGATATGCACTAAAAGCTTGTATGTTTCGCTGACTACATAC
TATGgtgagatcctaaagtattacctatttatttaccttttatagtttctatatattacttcagatgacgagatcatttagcacgcataaacaagtcacaaattattaag
taaaattctttcaagtttttgcagacctttgggtatctttctcactttttatgtctttttttaacctcaaaagtcacatgtacattcaactgcattcatgtccaaatctttctagaatg
attgcttggtctttgtttcgttactacggtgatttttcagcatgcatataagttcctcttcgttcttcgtttctcctttcaaggattgatctatctaggggagataggaatcaagc
aaattgttcaccgtcccatgcactatatgctagatcccattgtttttctttttaaataatgccatttcacgaggtaccattgctttagaaaaaaaatggtcagtaacgag
attttaatatctagcctgtcttttataagatataccaggtgtcttctataagatataccaggtaaatatagtaccatagaattttctaacggttcaaccagggacaatttgt
tttcacctagctgcgtacacacccattttatccacgcgcttcttaaataggttaaaaaatataaaacaaattggtagcatagattttctttaaagagacgtaaaatatat
tatgatgacaaatacctcttgtccaaccaggctcaaattattactctaaactgttttacaccaaaacttcagcctaaacagaaacatgcctggttatacatgccagg
agattgcttgttcggtttggagaggattgagggattccgcaccactaaaggtgtgtaataaatcccctccaatctcacttcttgaggatcaatcgaacatcacattaa
aagaaaaaacatgtttggtgcacgttcttaaataaaggcggagtacaaacgtctgtcgaacagcaccaatgcaaacaactgaatttaacagccatttcatgata
attatatatatatatatatatatataaaagatgtatctagctagactatatatatgtggtcatcctgtggactggagctgatcccctccacctccggctcgatgcccttga
acaaccgcgcgaacacgatgaacacgacgaggtccacggcggacagcacggcgagggtgatgaaggagcggtcgaggtggccgcggtcgagctcggc
caggatccaccccgccgtccctccgccggtccgccgccgcgaggcgacgccgctgatggcgctcaccatcaccatgctggcgtagttccccagcgagatgg
acgccatgcacagcgagctccccaggctcttcacccccctccggcgactgcacgttgaagaactccagctgccccacgtacacgaacacctccgacgcgccc
atcaccgcgtactgcggcgcctgccacagcacgctcatggcgcggccgccggcgccggatcggcggcggcggtggacctcgacgaccgccgcggcgacc
atgccgagcagcgcgatcacgaggcccgcgcccatgcgcttgagctcgccgacgccgcgcgggttcttggtcagcctcgccgccgcggcaccaggacgta
gtgggagaaggcgagcgtggcgagcacgccggcgacgtcgaacaccgacatggacgcggccggcgcgttgaacaggcccaggatgtcggtgtccatgg
ccgcgccttgctccacgaacaaggacgacatctgggtgaactccacggagtagacgatgctgcagatccagatgggcaccatgctcaccacgcacttggcct
cctccacctgcgtcaccgtgcacagtctccacgggttcttggcgttcccgtcgtggtagtcctcctcggtcgccgtcgccgccttgtcaagaaacctgagctggtcg
ctgtgggcgagcttgccgacgccacggatcgccgagccctcgccatcgacctcgtggaggtggtcgccgggcggcggcacgatgtgccgcttgcggtacgcg
gcgacgaacacctgggcgatgcgggtgagcgggttgccggcaggtcggacccggcggtagcgcggcgtgccgaggagaaagagcgcgagcgcgagcg
cggcggcggcggtggagacccagaagccggcgacccaccggcccctgtcctcgaagaacaccaggacggagttgtagaagagggagccgacgttgagc
gagaggtagaagaggcagaagaaggcctgcttgcgccgccgctcgccggggtcggcgtcgtcgaactggtcggcgccgaacgtcgccaccgacggctggt
acccgccgttcccgaacgccgccatgtagatggacaggtagaacaccgcgacgccacgccgggacggcgccgcgcactgcctgagcccgccgccgtcgc
cgcaccccggcggctccaccagcaagaaccacgacaacagcgacaggagcatcaacccctgcatgccaaaacacacaagaaattaaacttgtctcatgc
atcaactgctgacactcttaaccttataataactttaaacttataattcagttttgctattttcagtcgtctgaaatcaaaattgcacatatgctctgtttttacataattaag
attgtttaaaatgttgacacagtatttatgttgttatattttatactactgctgagtttatcctgatatctgactgcatatttttcagGATATCACCTGTTTGACAA
GAGAAGGATTACATACCACGATGAAGATGAATTGGAACATGATgcaagtgatgtagcgccccatataggagtcactcaggaa
agcacagaagagggagaagatgtagacggtgcccatccaca*tgctgacgctattggcggcctcgg*cgttcctggtggagcacctgcctgaggaacaccac
caggcccacggcgacgccaaaaaatgcaaagttggccaacacatagctcactgcatcgtcaagtagagctgcttaatcactgaggtaaaataaatattttaattt
cttttggatcaaaccactatatatgcccccattttgcattgcagtgttgttcaacactggttagtttatctctactatatatcttaaaagcacagtcatccttattcccattcta
tccataagaaacactagaaaaaactaaccaattgagagaaaaatatgggagaagagaaaaaaaaattaaaccacattcaccatatcacatccgtttgcaag
gcacggtcctatgactagtattgtataaaatgatagattgttctccacattatattggtataaatactggactattagtaaatcaaacactattaaccacgaaaaaaa
agagagagttgggatgagattgtggggattaaatttttaccaagaagtagtgccattgtcatctttcctcttgaagtcttcagttctgggcttccctggaaatgttgggtc
tgatcttcagtgtgcacaaatgactcattgtatatcatggaattgcatggagagcatgatcccacagattcaacatcttccattggcttttaaaaaaaagtagttgagg
aaaaaggtgtcacaactcacttaccactctactagaaagtaataaggatagactaaaaatttagagtttttattcttggtttgattaattcgccgacaaataataagt
acaaacagaacaaatgattctgaagtgttacctatcatattcaattataatattcaacgtaacaagtagcaatctaaaggacatcatcttggggaggtacttaattg
gtacttcctccattccaaaatgtttgacgccgttgactttttaaaatatgtttgaccgtttgtcttattcaaaaaatttaagtaattattaattcttttcctatcatttgatttattgtt
aaatatacttttatgtatatatatagttttatatatttcataaaagtttttgaataagacgaacggtcaaacatatttaaaaaagccaacggcgtcaaacatttaaggaa
ggagggagtataatataaaaagaatatgatgtttttaggttttgtcctcttcttgaagaggtatatgccttcttaccattttagaaatacctcgccataccggagatatca
aactaattgcataatttcacaaatcatatttataaatgtttttttattttatttttaaactttgctaggtatatacatttagttcgccttcttcagcgttgccatggacctggtgatG
TTCTTCCGGCGGGTGCCCCACCAAGAGAACGCCGTGGCCACCAACAACATCAGCATATGGATGGGCACC
ATCTTCATCTTTGCCCTCTTTAGTGCTTTCCGTAGTGATTCCTATACGGGGTGCTACTTCACTTGGATCATGT
TACAATTTATCTTCATCGTGATATATGCTCCTTCTGTTCTCACATAGGTGATATCTTAAAATGTATGAGGCAT
ATATACTTTCTACCTAATATTATAAAGTATATGCCTCTATATAGAATCAAATAAAGCAGAAAAGTCATTGTTA
TTACCAATCGTGTACTTTTGTTCTAAACATCTCAACTAGTTTAAAGTATTTGTCTCTCTTGAgcaatgggtttaaacct
ctccacggatgggagagaacctctactatttgattgttccaacttttgacacaatagaaacacagatgatactgaaggtatgaaaggtaaatagttagttaaggttc
caatcattcaaatgctggaaagtacatttacttctatttaaactattaaggggtaaaaaaaaacagatatacgctcttactctgatctcaaatgccatgatctctgca
gatcccacggtgtcgggaaccttcaatacgaatatatatataaaaaagaaaagatcagtaaggaaatgtttgatctgctagccttagttttcatattattaaattttag
aaaatacaagtaagattataaaattataagtttgctacaatatttatgtctgaacatagtataa

FIGURE 3 pMON94320 pMON100574 pMON100575 pMON100576

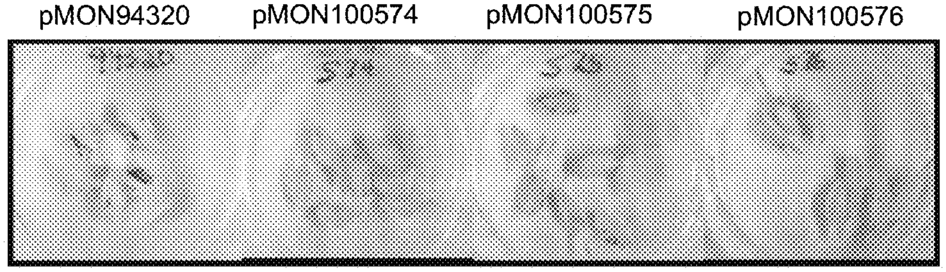

A

B pMON94320(control GUS)
ATCGTCGGCTACAGCCTCGGGAATT CTCTGCATGCGTTTGGACGTATGCTCATTCAG

C pMON100574(sense ID1379342)
CTACAGCCTC GGGAATTCTGCCCCACCAAGAGAACGCCGTCTGCATGCGTTT

D pMON100575 (antisense ID1379342)
CTACAGCCTC GGGAATTCCGGCGTTCTCTTGGTGGGGCATCTGCATGCGTTT

E pMON100576 (antisense ID1379342+ ID1275002)
CTACAGCCTCGGGAATT CTGCTGATGTTGTTGGTGGCCACGG CGTTCTCTTGGTGGGGCATCTGCATGCGTTT Developing Maize Endosperm (DAP)
*10 DAP are whole kernel*

*10*  21  27  33  NA  *10*  15  21  27  33  39

Developing Maize Embryo (DAP)
21  27  33  44  21  27  33  39  44

FIGURE 9
FIGURE 9A
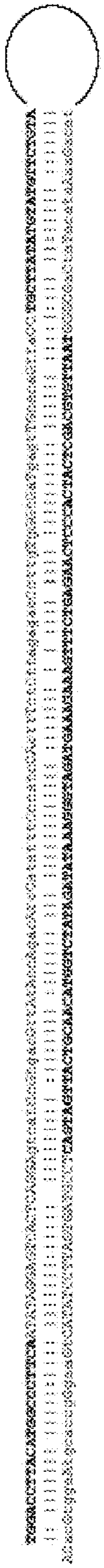
FIGURE 9B

SEQUENCE LISTING

```
<160> NUMBER OF SEQ ID NOS: 97

<210> SEQ ID NO 1
<211> LENGTH: 21
<212> TYPE: RNA
<213> ORGANISM: Oryza sativa

<400> SEQUENCE: 1

augcaaguga uguagcgccc c                                              21


<210> SEQ ID NO 2
<211> LENGTH: 21
<212> TYPE: RNA
<213> ORGANISM: Oryza sativa

<400> SEQUENCE: 2

auauaggagu cacucaggaa a                                              21


<210> SEQ ID NO 3
<211> LENGTH: 21
<212> TYPE: RNA
<213> ORGANISM: Oryza sativa

<400> SEQUENCE: 3

ucuuugcccu cuuuagugcu u                                              21
```

<210> SEQ ID NO 4
<211> LENGTH: 21
<212> TYPE: RNA
<213> ORGANISM: Oryza sativa

<400> SEQUENCE: 4
uauggauggg caccaucuuc a 21

<210> SEQ ID NO 5
<211> LENGTH: 21
<212> TYPE: RNA
<213> ORGANISM: Oryza sativa

<400> SEQUENCE: 5
uggccaccaa caacaucagc a 21

<210> SEQ ID NO 6
<211> LENGTH: 21
<212> TYPE: RNA
<213> ORGANISM: Oryza sativa

<400> SEQUENCE: 6
ugccccacca agagaacgcc g 21

<210> SEQ ID NO 7
<211> LENGTH: 21
<212> TYPE: RNA
<213> ORGANISM: Oryza sativa

<400> SEQUENCE: 7
ugccugagga acaccaccca g 21

<210> SEQ ID NO 8
<211> LENGTH: 5521
<212> TYPE: DNA
<213> ORGANISM: Oryza sativa

<400> SEQUENCE: 8
aaaatttcta ccatctcact tttgtaataa taccataaat gctttgccat atgtaaaacc 60
gttcgagtag cgacaacacc ggttctataa aagttgttcc ctttccacgt acttataagc 120
ttatctagtg tgcacgcatt ccctttccac gtatttccac gtatttccat taaccttatc 180
ttgtgtgcac gcataaggta catgggtaat aacatgttct tggaagtggt ccttacctac 240
accgctatat aaagcgacgc ctctcattgc gacaccacca atcttattct acatatttct 300
atcttatata gaacaactag catagctctc gttgcccagc caggttgccc agccaggttg 360
cctggtgcac aatgagagct ggctagggcg gactcattct gctgttggtg cccaacgatg 420
ctagctgcta ctcatactag tgaagcctgc catggttctg agaaattttt ggatactccg 480
ctgcgtagat atgcactaaa agcttgtatg tttcgctgac tacatactat ggtgagatcc 540
taaagtatta cctatttatt tacctttta tagtttctat atattacttc agatgacgag 600
atcatttagc acgcataaac aagtcacaaa ttattaagta aaattctttc aagtttttgc 660
agacctttgg gtatctttct cactttttat gtctttttta acctcaaaag tcacatgtac 720
attcaactgc attcatgtcc aaatctttct agaatgattg cttggtcttt gtttcgttac 780
tacggtgatt tttcagcatg catataagtt cctcttcgtt cttcgtttct cctttcaagg 840
attgatctat ctaggggaga taggaatcaa gcaaattgtt caccgtccca tgcactatat 900
gctagatccc attgtttttt ctttttaaat aatgccattt cacgaggtac cattgcttta 960

-continued

```
gaaaaaaaat ggtcagtaac gagattttaa tatctagcct gtcttttata agatatacca   1020
ggtgtcttct ataagatata ccaggtaaat atagtaccat agaattttct aacggttcaa   1080
ccagggacaa tttgttttca cctagctgcg tacacaccca ttttatccac gcgcttctta   1140
aataggttaa aaaatataaa acaaattggt agcatagatt ttctttaaag agacgtaaaa   1200
tatattatga tgacaaatac ctcttgtcca accaggctca aattattact ctaaactgtt   1260
ttacaccaaa acttcagcct aaacagaaac atgcctggtt atacatgcca ggagattgct   1320
tgttcggttt ggagaggatt gagggattcc gcaccactaa aggtgtgtaa taaatcccct   1380
ccaatctcac ttcttgagga tcaatcgaac atcacattaa aagaaaaaac atgtttggtg   1440
cacgttctta aataaaggcg gagtacaaac gtctgtcgaa cagcaccaat gcaaacaact   1500
gaatttaaca gccatttcat gataattata tatatatata tatatatata aaagatgtat   1560
ctagctagac tatatatatg tggtcatcct gtggactgga gctgatcccc tccacctccg   1620
gctcgatgcc cttgaacaac cgcgcgaaca cgatgaacac gacgaggtcc acggcggaca   1680
gcacggcgag ggtgatgaag gagcggtcga ggtggccgcg gtcgagctcg gccaggatcc   1740
accccgccgt ccctccgccg gtccgccgcc gcgaggcgac gccgctgatg gcgctcacca   1800
tcaccatgct ggcgtagttc cccagcgaga tggacgccat gcacagcgag ctccccaggc   1860
tcttcacccc ctccggcgac tgcacgttga agaactccag ctgccccacg tacacgaaca   1920
cctccgacgc gcccatcacc gcgtactgcg gcgcctgcca cagcacgctc atggcgcggc   1980
cgccggcgcc ggatcggcgg cggcggtgga cctcgacgac cgccgcggcg accatgccga   2040
gcagcgcgat cacgaggccc gcgcccatgc gcttgagctc gccgacgccg cgcgggttct   2100
tggtcagcct cgccgccgcg ggcaccagga cgtagtggga gaaggcgagc gtggcgagca   2160
cgccggcgac gtcgaacacc gacatggacg cggccggcgc gttgaacagg cccaggatgt   2220
cggtgtccat ggccgcgcct tgctccacga acaaggacga catctgggtg aactccacgg   2280
agtagacgat gctgcagatc cagatgggca ccatgctcac cacgcacttg gcctcctcca   2340
cctgcgtcac cgtgcacagt ctccacgggt tcttggcgtt cccgtcgtgg tagtcctcct   2400
cggtcgccgt cgccgccttg tcaagaaacc tgagctggtc gctgtgggcg agcttgccga   2460
cgccacggat cgccgagccc tcgccatcga cctcgtggag gtggtcgccg ggcggcggca   2520
cgatgtgccg cttgcggtac gcggcgacga acacctgggc gatgcgggtg agcgggttgc   2580
cggcaggtcg gacccggcgg tagcgcggcg tgccgaggag aaagagcgcg agcgcgagcg   2640
cggcggcggc ggtggagacc cagaagccgg cgacccaccg gcccctgtcc tcgaagaaca   2700
ccaggacgga gttgtagaag agggagccga cgttgagcga gaggtagaag aggcagaaga   2760
aggcctgctt gcgccgccgc tcgccggggt cggcgtcgtc gaactggtcg gcgccgaacg   2820
tcgccaccga cggctggtac ccgccgttcc cgaacgccgc catgtagatg gacaggtaga   2880
acaccgcgac gccacgccgg gacggcgccg cgcactgcct gagcccgccg ccgtcgccgc   2940
accccggcgg ctccaccagc aagaaccacg acaacagcga caggagcatc aacccctgca   3000
tgccaaaaca cacaagaaat taaacttgtc tcatgcatca actgctgaca ctcttaacct   3060
tataataact ttaaacttat aattcagttt tgctattttc agtcgtctga aatcaaaatt   3120
gcacatatgc tctgtttttt acataattaa gattgtttaa aatgttgaca cagtatttat   3180
gttgttatat tttatactac tgctgagttt atcctgatat ctgactgcat atttttcagg   3240
atatcacctg tttgacaaga gaaggattac ataccacgat gaagatgaat tggaacatga   3300
tgcaagtgat gtagcgcccc atataggagt cactcaggaa agcacagaag agggagaaga   3360
```

-continued tgtagacggt gcccatccac atgctgacgc tattggcggc ctcggcgttc tcctggtgga 3420
gcacctgcct gaggaacacc accaggccca cggcgacgcc aaaaaatgca aagttggcca 3480
acacatagct cactgcatcg tcaagtagag ctgcttaatc actgaggtaa aataaatatt 3540
ttaatttctt ttggatcaaa ccactatata tgccccccatt ttgcattgca gtgttgttca 3600
acactggtta gtttatctct actatatatc ttaaaagcac agtcatcctt attcccattc 3660
tatccataag aaacactaga aaaaactaac caattgagag aaaaatatgg gagaagagaa 3720
aaaaaaatta aaccacattc accatatcac atccgtttgc aaggcacggt cctatgacta 3780
gtattgtata aaatgataga ttgttctcca cattatattg gtataaatac tggactatta 3840
gtaaatcaaa cactattaac cacgaaaaaa aagagagagt tgggatgaga ttgtggggat 3900
taaattttta ccaagaagta gtgccattgt catctttcct cttgaagtct tcagttctgg 3960
gcttccctgg aaatgttggg tctgatcttc agtgtgcaca aatgactcat tgtatatcat 4020
ggaattgcat ggagagcatg atcccacaga ttcaacatct tccattggct tttaaaaaaa 4080
agtagttgag gaaaaaggtg tcacaactca cttaccactc tactagaaag taataaggat 4140
agactaaaaa ttttagagtt tttattcttg gtttgattaa ttcgccgaca aataataagt 4200
acaaacagaa caaatgattc tgaagtgtta cctatcatat tcaattataa tattcaacgt 4260
aacaagtagc aatctaaagg acatcatctt ggggaggtac ttaattggta cttcctccat 4320
tccaaaatgt ttgacgccgt tgacttttta aaatatgttt gaccgtttgt cttattcaaa 4380
aaatttaagt aattattaat tcttttccta tcatttgatt tattgttaaa tatactttta 4440
tgtatatata tagttttata tatttcataa aagtttttga ataagacgaa cggtcaaaca 4500
tatttaaaaa agccaacggc gtcaaacatt taaggaagga gggagtataa tataaaaaga 4560
atatgatgtt tttaggtttt gtcctcttct tgaagaggta tatgccttct taccatttta 4620
gaaatacctc gccataccgg agatatcaaa ctaattgcat aatttcacaa atcatattta 4680
taaatgtttt ttattttatt tttaaacttt gctaggtata tacatttagt tcgccttctt 4740
cagcgttgcc atggacctgg tgatgttctt ccggcgggtg ccccaccaag agaacgccgt 4800
ggccaccaac aacatcagca tatggatggg caccatcttc atctttgccc tctttagtgc 4860
tttccgtagt gattcctata cggggtgcta cttcacttgg atcatgttac aatttatctt 4920
catcgtgata tatgctcctt ctgttctcac ataggtgata tcttaaaatg tatgaggcat 4980
atatactttc tacctaatat tataaagtat atgcctctat atagaatcaa ataaagcaga 5040
aaagtcattg ttattaccaa tcgtgtactt ttgttctaaa catctcaact agtttaaagt 5100
atttgtctct cttgagcaat gggtttaaac ctctccacgg atgggagaga acctctacta 5160
tttgattgtt ccaacttttg acacaataga aacacagatg atactgaagg tatgaaaggt 5220
aaatagttag ttaaggttcc aatcattcaa atgctggaaa gtacatttac ttctatttta 5280
aactattaag ggtaaaaaaa aaacagatat acgctcttac tctgatctca aatgccatga 5340
tctctgcaga tcccacggtg tcgggaacct tcaatacgaa tatatatata aaaaagaaaa 5400
gatcagtaag gaaatgtttg atctgctagc cttagttttc atattattaa attttagaaa 5460
atacaagtaa gattataaaa ttataagttt gctacaatat ttatgtctga acatagtata 5520
a 5521

<210> SEQ ID NO 9
<211> LENGTH: 2454
<212> TYPE: DNA

<213> ORGANISM: Oryza sativa
<220> FEATURE:
<221> NAME/KEY: misc_feature
<222> LOCATION: (1)..(2454)
<223> OTHER INFORMATION: N is A, T, G, or C
<220> FEATURE:
<221> NAME/KEY: unsure
<222> LOCATION: (1)..(2454)
<223> OTHER INFORMATION: unsure at all n locations

<400> SEQUENCE: 9

```
aatcttattc tacatatttc tatcttatat agaacaacta gcatagctct cgttgcccag     60

ccaggttgcc cagccaggtt gcctggtgca caatgagagc tggctagggc ggactcattc    120

tgctgttggt gcccaacgat gctagctgct actcatacta gtgaagcctg ccatggttct    180

gagaaatttt tggatactcc gctgcgtaga tatgcactaa aagcttgtat gtttcgctga    240

ctacatacta tgctagacta tatatatgtg gtcatcctgt ggactggagc tgatcccctc    300

cacctccggc tcgatgccct tgaacaaccg cgcgaacacg atgaacacga cgaggtccac    360

ggcggacagc acggcgaggg tgatgaagga gcggtcgagg tggccgcggt cgagctcggc    420

caggatccac cccgccgtcc ctccgccggt ccgccgccgc gaggcgacgc cgctgatggc    480

gctcaccatc accatgctgg cgtagttccc cagcgagatg gacgccatgc acagcgagct    540

ccccaggctc ttcacccccct ccggcgactg cacgttgaag aactccagct gccccacgta    600

cacgaacacc tccgacgcgc ccatcaccgc gtactgcggc gcctgccaca gcacgctcat    660

ggcgcggccg ccggcgccgg atcggcggcg gcggtggacc tcgacgaccg ccgcggcgac    720

catgccgagc agcgcgatca cgaggcccgc gcccatgcgc ttgagctcgc cgacgccgcg    780

cgggttcttg gtcagcctcg ccgccgcggg caccaggacg tagtgggaga aggcgagcgt    840

ggcgagcacg ccggcgacgt cgaacaccga catggacgcg gccggcgcgt tgaacaggcc    900

caggatgtcg gtgtccatgg ccgcgccttg ctccacgaac aaggacgaca tctgggtgaa    960

ctccacggag tagacgatgc tgcagatcca gatgggcacc atgctcacca cgcacttggc   1020

ctcctccacc tgcgtcaccg tgcacagtct ccacgggttc ttggcgttcc cgtcgtggta   1080

gtcctcctcg gtcgccgtcg ccgccttgtc aagaaacctg agctggtcgc tgtgggcgag   1140

cttgccgacg ccacggatcg ccgagccctc gccatcgacc tcgtggaggt ggtcgccggg   1200

cggcggcacg atgtgccgct ggggttagtc ngggacgaac acctgggcga tgcgggtgag   1260

cgggttgccg gcaggtcgga cccggcggta gcgcggcgtg ccgaggagaa agagcgcgag   1320

cgcgagcgcg gcggcggcgg tggagaccca gaagccggcg acccaccggc ccctgtcctc   1380

gaagaacacc aggacggagt tgtagaagag ggagccgacg ttgagcgaga ggtagaagag   1440

gcagaagaag gcctgcttgc gccgccgctc gccggggtcg gcgtcgtcga actggtcggc   1500

gccgaacgtc gccaccgacg gctggtaccc gccgttcccg aacgccgcca tgtagatgga   1560

caggtagaac accgcgacgc cacgccggga cggcgccgcg cactgcctga gcccgccgcc   1620

gtcgccgcac cccggcggct ccaccaccca caaccacgac aacagcgaca ggagcatcaa   1680

ccccacgatg aagatgaatt ggaacatgat gcaagtgatg tagcgcccca tataggagtc   1740

actcaggaaa gcacagaaga gggagaagat gtagacggtg cccatccaca tgctgacgct   1800

attggcggcc tcggcgttct cctggtggag cacctgcctg aggaacacca ccaggcccac   1860

ggcgacgcca aaaaatgcaa agttggccaa cacatagctc acaagaagta gtgccattgt   1920

catctttcct cttgaagtct tcagttctgg gcttccctgg aaatgttggg tctgatcttc   1980

agtgtgcaca aatgactcat tgtatatcat ggaattgcat ggagagcatg atcccacaga   2040
```

```
ttcaacatct tccattggca ttttagaaat acctcgccat accggagata tcaaactggt   2100

gatgttcttc cggcgggtgc cccaccaaga gaacgccgtg gccaccaaca acatcagcat   2160

atggatgggc accatcttca tctttgccct ctttagtgct ttccgtagtg attcctatac   2220

ggggtgctac ttcacttgga tcatgttaca atttatcttc atcgtgatat atgctccttc   2280

tgttctcaca taggtgatat cttaaaatgt atgaggcata tatactttct acctaatatt   2340

ataaagtata tgcctctata tagaatcaaa taaagcagaa aagtcattgt tattaccaat   2400

cgtgtacttt tgttctaaac atctcaacta gtttaaagta tttgtctctc ttga         2454
```

```
<210> SEQ ID NO 10
<211> LENGTH: 684
<212> TYPE: DNA
<213> ORGANISM: Oryza sativa

<400> SEQUENCE: 10

aatcttattc tacatatttc tatcttatat agaacaacta gcatagctct cgttgcccag     60

ccaggttgcc cagccaggtt gcctggtgca caatgagagc tggctagggc ggactcattc    120

tgctgttggt gcccaacgat gctagctgct actcatacta gtgaagcctg ccatggttct    180

gagaaatttt tggatactcc gctgcgtaga tatgcactaa aagcttgtat gtttcgctga    240

ctacatacta tggatatcac ctgtttgaca agagaaggat tacataccac gatgaagatg    300

aattggaaca tgatgttctt ccggcgggtg ccccaccaag agaacgccgt ggccaccaac    360

aacatcagca tatggatggg caccatcttc atctttgccc tctttagtgc tttccgtagt    420

gattcctata cggggtgcta cttcacttgg atcatgttac aatttatctt catcgtgata    480

tatgctcctt ctgttctcac ataggtgata tcttaaaatg tatgaggcat atatactttc    540

tacctaatat tataaagtat atgcctctat atagatcaaa taaagcagaa aagtcattgt    600

tattaccaat cgtgtacttt tgttctaaac atctcaacta gtttaaagta tttgtctctc    660

ttgaacaaaa aaaaaaaaaa aaaa                                           684
```

```
<210> SEQ ID NO 11
<211> LENGTH: 564
<212> TYPE: DNA
<213> ORGANISM: Oryza sativa
<220> FEATURE:
<221> NAME/KEY: misc_feature
<222> LOCATION: (1)..(564)
<223> OTHER INFORMATION: N is A, T, G, or C
<220> FEATURE:
<221> NAME/KEY: unsure
<222> LOCATION: (1)..(564)
<223> OTHER INFORMATION: unsure at all n locations

<400> SEQUENCE: 11

aatcttattc tacatatttc tatcttatat agaacaacta gcatagctct cgttgcccag     60

ccaggttgcc cagccaggtt gcctggtgca caatgagagc tggctagggc ggactcattc    120

tgctgttggt gcccaacgat gctagctgct actcatacta gtgaagcctg ccatggttct    180

gagaaatttt tggatactcc gctgcgtaga tatgcactaa aagcttgtat gtttcgctga    240

ctacatacta tggatatcac ctgtttgaca agagaaggat tacataccac gatgaagatg    300

aattggaaca tgatgcaagt gatgtagcgc cccatatagg agtcactcag gaaagcacag    360

aagagggaga agatgtagac ggtgcccatc cacatgctga cgctattggc ggcctcggcg    420

ttctcctggt ggagcacctg cctgaggaac accaccaggc ccacggcgac gccaaaaaat    480
```

gcaaagntgg ccaacacata gctcactgca tcgncaagna gagctgcnta atcactgagg 540
gatatccatt tannntggnc ttct 564

<210> SEQ ID NO 12
<211> LENGTH: 57
<212> TYPE: DNA
<213> ORGANISM: artificial sequence
<220> FEATURE:
<223> OTHER INFORMATION: synthetic construct

<400> SEQUENCE: 12
atcgtcggct acagcctcgg gaattctctg catgcgtttg gacgtatgct cattcag 57

<210> SEQ ID NO 13
<211> LENGTH: 78
<212> TYPE: DNA
<213> ORGANISM: artificial sequence
<220> FEATURE:
<223> OTHER INFORMATION: synthetic construct

<400> SEQUENCE: 13
atcgtcggct acagcctcgg gaattctgcc ccaccaagag aacgccgtct gcatgcgttt 60
ggacgtatgc tcattcag 78

<210> SEQ ID NO 14
<211> LENGTH: 78
<212> TYPE: DNA
<213> ORGANISM: artificial sequence
<220> FEATURE:
<223> OTHER INFORMATION: synthetic construct

<400> SEQUENCE: 14
atcgtcggct acagcctcgg gaattccggc gttctcttgg tggggcatct gcatgcgttt 60
ggacgtatgc tcattcag 78

<210> SEQ ID NO 15
<211> LENGTH: 99
<212> TYPE: DNA
<213> ORGANISM: artificial sequence
<220> FEATURE:
<223> OTHER INFORMATION: synthetic construct

<400> SEQUENCE: 15
atcgtcggct acagcctcgg gaattctgct gatgttgttg gtggccacgg cgttctcttg 60
gtggggcatc tgcatgcgtt tggacgtatg ctcattcag 99

<210> SEQ ID NO 16
<211> LENGTH: 21
<212> TYPE: DNA
<213> ORGANISM: artificial sequence
<220> FEATURE:
<223> OTHER INFORMATION: synthetic construct

<400> SEQUENCE: 16
cggcgttctc ttggtggggc a 21

<210> SEQ ID NO 17
<211> LENGTH: 939
<212> TYPE: DNA
<213> ORGANISM: artificial sequence
<220> FEATURE:
<223> OTHER INFORMATION: synthetic construct

<400> SEQUENCE: 17

-continued aatcttattc tacatatttc tatcttatat agaacaacta gcatagctct cgttgcccag 60
ccaggttgcc cagccaggtt gcctggtgca caatgagagc tggctagggc ggactcattc 120
tgctgttggt gcccaacgat gctagctgct actcatacta gtgaagcctg ccatggttct 180
gagaaatttt tggatactcc gctgcgtaga tatgcactaa aagcttgtat gtttcgctga 240
ctacatacta tggatatcac ctgtttgaca agagaaggat tacataccac gatgaagatg 300
aattggaaca tgatgcaagt gatgtagcgc cccatatagg agtcactcag gaaagcacag 360
aagagggaga agatgtagac ggtgcccatc cacatgctga cgctattggc ggcctcggcg 420
ttctcctggt ggagcacctg cctgaggaac accaccaggc ccacggcgac gccaaaaaat 480
gcaaagttgg ccaacacata gctcactgca tcgtcaagta gagctgctta atcactgagg 540
gtatatacat ttagttcgcc ttcttcagcg ttgccatgga cctggtgatg ttcttccggc 600
gggtgcccca ccaagagaac gccgtggcca ccaacaacat cagcatatgg atgggcacca 660
tcttcatctt tgccctcttt agtgctttcc gtagtgattc ctatacgggg tgctacttca 720
cttggatcat gttacaattt atcttcatcg tgatatatgc tccttctgtt ctcacatagg 780
tgatatctta aaatgtatga ggcatatata ctttctacct aatattataa agtatatgcc 840
tctatataga tcaaataaag cagaaaagtc attgttatta ccaatcgtgt acttttgttc 900
taaacatctc aactagttta aagtatttgt ctctcttga 939

<210> SEQ ID NO 18
<211> LENGTH: 312
<212> TYPE: DNA
<213> ORGANISM: artificial sequence
<220> FEATURE:
<223> OTHER INFORMATION: synthetic construct

<400> SEQUENCE: 18
aatcttattc tacatatttc tatcttatat agaacaacta gcatagctct cgttgcccag 60
ccaggttgcc cagccaggtt gcctggtgca caatgagagc tggctagggc ggactcattc 120
tgctgttggt gcccaacgat gctagctgct actcatacta gtgaagcctg ccatggttct 180
gagaaatttt tggatactcc gctgcgtaga tatgcactaa aagcttgtat gtttcgctga 240
ctacatacta tggatatcac ctgtttgaca agagaaggat tacataccac gatgaagatg 300
aattggaaca tg 312

<210> SEQ ID NO 19
<211> LENGTH: 21
<212> TYPE: DNA
<213> ORGANISM: artificial sequence
<220> FEATURE:
<223> OTHER INFORMATION: synthetic construct

<400> SEQUENCE: 19
gcacagaaga gggagaagat g 21

<210> SEQ ID NO 20
<211> LENGTH: 21
<212> TYPE: DNA
<213> ORGANISM: artificial sequence
<220> FEATURE:
<223> OTHER INFORMATION: synthetic construct

<400> SEQUENCE: 20
tagacggtgc ccatccacat g 21

<210> SEQ ID NO 21
<211> LENGTH: 21
<212> TYPE: DNA
<213> ORGANISM: artificial sequence
<220> FEATURE:
<223> OTHER INFORMATION: synthetic construct

<400> SEQUENCE: 21
ctgacgctat tggcggcctc g 21

<210> SEQ ID NO 22
<211> LENGTH: 21
<212> TYPE: DNA
<213> ORGANISM: artificial sequence
<220> FEATURE:
<223> OTHER INFORMATION: synthetic construct

<400> SEQUENCE: 22
gcgttctcct ggtggagcac c 21

<210> SEQ ID NO 23
<211> LENGTH: 123
<212> TYPE: DNA
<213> ORGANISM: artificial sequence
<220> FEATURE:
<223> OTHER INFORMATION: synthetic construct

<400> SEQUENCE: 23
cccacggcga cgccaaaaaa tgcaaagttg gccaacacat agctcactgc atcgtcaagt 60
agagctgctt aatcactgag ggtatataca tttagttcgc cttcttcagc gttgccatgg 120
acc 123

<210> SEQ ID NO 24
<211> LENGTH: 21
<212> TYPE: DNA
<213> ORGANISM: artificial sequence
<220> FEATURE:
<223> OTHER INFORMATION: synthetic construct

<400> SEQUENCE: 24
tggtgatgtt cttccggcgg g 21

<210> SEQ ID NO 25
<211> LENGTH: 21
<212> TYPE: DNA
<213> ORGANISM: artificial sequence
<220> FEATURE:
<223> OTHER INFORMATION: synthetic construct

<400> SEQUENCE: 25
tccgtagtga ttcctatacg g 21

<210> SEQ ID NO 26
<211> LENGTH: 21
<212> TYPE: DNA
<213> ORGANISM: artificial sequence
<220> FEATURE:
<223> OTHER INFORMATION: synthetic construct

<400> SEQUENCE: 26
ggtgctactt cacttggatc a 21

<210> SEQ ID NO 27
<211> LENGTH: 210

-continued

<212> TYPE: DNA
<213> ORGANISM: artificial sequence
<220> FEATURE:
<223> OTHER INFORMATION: synthetic construct

<400> SEQUENCE: 27
tgttacaatt tatcttcatc gtgatatatg ctccttctgt tctcacatag gtgatatctt 60
aaaatgtatg aggcatatat actttctacc taatattata aagtatatgc ctctatatag 120
atcaaataaa gcagaaaagt cattgttatt accaatcgtg tacttttgtt ctaaacatct 180
caactagttt aaagtatttg tctctcttga 210

<210> SEQ ID NO 28
<211> LENGTH: 21
<212> TYPE: DNA
<213> ORGANISM: artificial sequence
<220> FEATURE:
<223> OTHER INFORMATION: synthetic construct

<400> SEQUENCE: 28
tgacatcaag tgatctatgc g 21

<210> SEQ ID NO 29
<211> LENGTH: 21
<212> TYPE: DNA
<213> ORGANISM: artificial sequence
<220> FEATURE:
<223> OTHER INFORMATION: synthetic construct

<400> SEQUENCE: 29
tacacctgca tctttggcac a 21

<210> SEQ ID NO 30
<211> LENGTH: 21
<212> TYPE: DNA
<213> ORGANISM: artificial sequence
<220> FEATURE:
<223> OTHER INFORMATION: synthetic construct

<400> SEQUENCE: 30
tctccttggc gagcggcgca t 21

<210> SEQ ID NO 31
<211> LENGTH: 21
<212> TYPE: DNA
<213> ORGANISM: artificial sequence
<220> FEATURE:
<223> OTHER INFORMATION: synthetic construct

<400> SEQUENCE: 31
ttgtggatgc agaaagcggt g 21

<210> SEQ ID NO 32
<211> LENGTH: 939
<212> TYPE: DNA
<213> ORGANISM: artificial sequence
<220> FEATURE:
<223> OTHER INFORMATION: synthetic construct

<400> SEQUENCE: 32
aatcttattc tacatatttc tatcttatat agaacaacta gcatagctct cgttgcccag 60
ccaggttgcc cagccaggtt gcctggtgca caatgagagc tggctagggc ggactcattc 120
tgctgttggt gcccaacgat gctagctgct actcatacta gtgaagcctg ccatggttct 180

```
gagaaatttt tggatactcc gctgcgtaga tatgcactaa aagcttgtat gtttcgctga    240
ctacatacta tggatatcac ctgtttgaca agagaaggat tacataccac gatgaagatg    300
aattggaaca tgatgcaagt gatgtagcgc cccatatagg agtcactcag gaaagcgcag    360
ctcgccaccg agatgcgccc aagatgcagg tgcatgctga cgctattggc ggcctcgcat    420
agatcccttg atatcacttt gtggatgcag aaagcggtgc ccacggcgac gccaaaaaat    480
gcaaagttgg ccaacacata gctcactgca tcgtcaagta gagctgctta atcactgagg    540
gtatatacat ttagttcgcc ttcttcagcg ttgccatgga caccgctctc tgcatcaaca    600
aagtgacatc aagtgatcta tgcgtggcca ccaacaacat cagcatacac ctgcatcttt    660
ggcacatctc cttggcgagc ggcgctttcc gtagtgattc ctatacgggg tgctacttca    720
cttggatcat gttacaattt atcttcatcg tgatatatgc tccttctgtt ctcacatagg    780
tgatatctta aaatgtatga ggcatatata ctttctacct aatattataa agtatatgcc    840
tctatataga tcaaataaag cagaaaagtc attgttatta ccaatcgtgt acttttgttc    900
taaacatctc aactagttta aagtatttgt ctctcttga                           939
```

<210> SEQ ID NO 33
<211> LENGTH: 2072
<212> TYPE: DNA
<213> ORGANISM: Oryza sativa

<400> SEQUENCE: 33

```
gattctcccc tgcgccgccg ccgccgccgc cgcctcaatc gggcgaagcc gccctcgccg     60
ccgtcgcggc ggcggcggcg agggcgagct cctgcgagag atcctccgcc gcctcatgcc    120
tcgcgcgcgc gctcccgctc ccgctctcgc ctgcagtatt tgttccattg ccgcgcacca    180
ctttccggtg ggcggcgggc aatgctaggg gttaagagac cttctctccc cgagatggag    240
gcgccgggcg gcgcggcggg ggacgcggag gaggaagttg atgcccggat ccgctgggtt    300
ccatggtggc tgctatggaa tggtggaatt gcttggatgg ccacgaaggg gatcgacgcc    360
aattgtttgg cgacctctac gatagaatcg cgtcgagtcg ggtgttcttt tcctgttatt    420
actagaagta gttgaatttc gtgattgaac acacaaggaa gcttgatatc gcgtcggggg    480
tgttctttcc tgttattact agatgtagtt gggtttcgtg attgaacacc taaggaaagg    540
aagcttgata aatggaagat agtccagcaa gttttgaaga tgatagaaaa tttgagcgcg    600
tcgtagtaac tgtcgtccac gatcacgtcc agtgttgttc atggcatggg ggatggagtc    660
aggatccttg aggcgtctgc tcctgttgca ctgcttcatg cctttcctgc cttctaggat    720
gcttaagatg gttgcgaagt caggtgcttg ggagttcatg aagcggtcat aatcaatttc    780
gctctctgta gtactttctc tggtgtcttc cccgttgctt ccttttggaa gaaaagcgtc    840
ctttagaatc tcttgagaga gtgcactttc tccctctcct gccatcagta gtgcctttat    900
tttcgcttgg tttccgcatc atcaggtggc acttatagaa attattttat ggaggaaaaa    960
gcattgtatg gcatgataga aatatcctta tggataaaac taggacactt gcaagtgttc   1020
aatgggagtc accttacctt ttttgcctac ctgtctgcat ttcatgaatg ggattccttc   1080
tcctgcgccg gtgctgtctt ctcaaatggg aaatggaggc aagcatctgc cctgttccat   1140
ggtggcagcc atggaatgat gggatttctt tgatggtcat aaaggagatc aaaaccaacg   1200
gttggcaatc tctgcaggga tgatgaacca ggcttgtaat atctgttgct gatttctttg   1260
gaagacataa cggcaagctt catggggcac gatggatttc agatggttgc ttcagccatg   1320
tctcaagatt cagttgatgg acctcaagtt tctgggtgca gtgccacgag tcttggtcag   1380
```

cccaagagta agcgcaggac tggtgacaag gcaagagggg agaagaaggc actcaaagtt 1440
aagattaacc ttgccagccc ggccaaaaaa attaagaaaa gtagcaaaaa gaagggcaaa 1500
aagggcactg ttgctggcag gatagggaga aaatgcactc tctcaagaga ttctaaaggg 1560
cgctttcttc caagagagag taagggggga gacatcggag gaaatgctac agagagtgaa 1620
gttgattatg accgcttcat gaactttcag gcacctgact tcgctaccat cttaagtatt 1680
ttgaaaggct ggaaaggcat gaagcaatgt aacaagatca ggcgcctcaa ggatcctgac 1740
ttcgtccctc tcatgaacgt catgagcaac actggatatg tgaccgagga tgatggtcac 1800
tatgatgtgc tgaaagtctt gatgcatgca gatggctggt ctgcatagtg attcaagctc 1860
tcaaatcaaa acattcaggc ctatggcctt gttgctagaa cagtggtttc ttctttcacc 1920
tttaaaactt gatggacttt gttccattta tcttagaaat tttgttgccc ttgagtccgg 1980
tggatatgta ctggagtatg ctatactggg tgatttaatg gtgataatgt taaatcttga 2040
tactagttca aaaaaaaaaa aaaaaaaaaa aa 2072

<210> SEQ ID NO 34
<211> LENGTH: 675
<212> TYPE: RNA
<213> ORGANISM: Oryza sativa

<400> SEQUENCE: 34
aguccagcaa guuuugaaga ugauagaaaa uuugagcgcg ucguaguaac ugucguccac 60
gaucacgucc aguguuguuc auggcauggg ggauggaguc aggauccuug aggcgucugc 120
uccuguugca cugcuucaug ccuuuccugc cuucuaggau gcuuaagaug guugcgaagu 180
caggugcuug ggaguucaug aagcggucau aaucaauuuc gcucucugua guacuuucuc 240
uggugucuuc cccguugcuu ccuuuuggaa gaaaagcguc cuuuagaauc ucuugagaga 300
gugcacuuuc ucccucuccu gccaucagua gugccuuuau uuucgcuugg uuuccggcaa 360
aaagggcacu guugcuggca ggauagggag aaaaugcacu cucucaagag auucuaaagg 420
gcgcuuucuu ccaagagaga guaagggggg agacaucgga ggaaaugcua cagagaguga 480
aguugauuau gaccgcuuca ugaacuuuca ggcaccugac uucgcuacca ucuuaaguau 540
uuugaaaggc uggaaaggca ugaagcaaug uaacagauca ggcgccucaa ggauccugac 600
uucgucccuc ucaugaacgu caugagcaac acuggauaug ugaccgagga ugauggucac 660
uaugaugugc ugaaa 675

<210> SEQ ID NO 35
<211> LENGTH: 21
<212> TYPE: RNA
<213> ORGANISM: Oryza sativa

<400> SEQUENCE: 35
ucacguccag uguuguucau g 21

<210> SEQ ID NO 36
<211> LENGTH: 21
<212> TYPE: RNA
<213> ORGANISM: Oryza sativa

<400> SEQUENCE: 36
gcauggggga uggagucagg a 21

<210> SEQ ID NO 37

<211> LENGTH: 21
<212> TYPE: RNA
<213> ORGANISM: Oryza sativa

<400> SEQUENCE: 37
uccuugaggc gucugcuccu g 21

<210> SEQ ID NO 38
<211> LENGTH: 21
<212> TYPE: RNA
<213> ORGANISM: Oryza sativa

<400> SEQUENCE: 38
uugcacugcu ucaugccuuu c 21

<210> SEQ ID NO 39
<211> LENGTH: 21
<212> TYPE: RNA
<213> ORGANISM: Oryza sativa

<400> SEQUENCE: 39
cugccuucua ggaugcuuaa g 21

<210> SEQ ID NO 40
<211> LENGTH: 21
<212> TYPE: RNA
<213> ORGANISM: Oryza sativa

<400> SEQUENCE: 40
augguugcga agucaggugc u 21

<210> SEQ ID NO 41
<211> LENGTH: 21
<212> TYPE: RNA
<213> ORGANISM: Oryza sativa

<400> SEQUENCE: 41
ugggaguuca ugaagcgguc a 21

<210> SEQ ID NO 42
<211> LENGTH: 21
<212> TYPE: RNA
<213> ORGANISM: Oryza sativa

<400> SEQUENCE: 42
uaaucaauuu cgcucucugu a 21

<210> SEQ ID NO 43
<211> LENGTH: 21
<212> TYPE: RNA
<213> ORGANISM: Oryza sativa

<400> SEQUENCE: 43
guacuuucuc uggugucuuc c 21

<210> SEQ ID NO 44
<211> LENGTH: 21
<212> TYPE: RNA
<213> ORGANISM: Oryza sativa

<400> SEQUENCE: 44
ccguugcuuc cuuuuggaag a 21

<210> SEQ ID NO 45
<211> LENGTH: 21
<212> TYPE: RNA
<213> ORGANISM: Oryza sativa

<400> SEQUENCE: 45
aaagcguccu uuagaaucuc u 21

<210> SEQ ID NO 46
<211> LENGTH: 21
<212> TYPE: RNA
<213> ORGANISM: Oryza sativa

<400> SEQUENCE: 46
ugagagagug cacuuucucc c 21

<210> SEQ ID NO 47
<211> LENGTH: 21
<212> TYPE: RNA
<213> ORGANISM: Oryza sativa

<400> SEQUENCE: 47
ucuccugcca ucaguagugc c 21

<210> SEQ ID NO 48
<211> LENGTH: 21
<212> TYPE: RNA
<213> ORGANISM: Oryza sativa

<400> SEQUENCE: 48
cacuguugcu ggcaggauag g 21

<210> SEQ ID NO 49
<211> LENGTH: 21
<212> TYPE: RNA
<213> ORGANISM: Oryza sativa

<400> SEQUENCE: 49
gagaaaaugc acucucucaa g 21

<210> SEQ ID NO 50
<211> LENGTH: 20
<212> TYPE: RNA
<213> ORGANISM: Oryza sativa

<400> SEQUENCE: 50
agauucuaaa gggcgcuuuc 20

<210> SEQ ID NO 51
<211> LENGTH: 21
<212> TYPE: RNA
<213> ORGANISM: Oryza sativa

<400> SEQUENCE: 51
uuccaagaga gaguaagggg g 21

<210> SEQ ID NO 52
<211> LENGTH: 21
<212> TYPE: RNA
<213> ORGANISM: Oryza sativa

<400> SEQUENCE: 52
gagacaucgg aggaaaugcu a 21

<210> SEQ ID NO 53
<211> LENGTH: 21
<212> TYPE: RNA
<213> ORGANISM: Oryza sativa

<400> SEQUENCE: 53
cagagaguga aguugauuau g 21

<210> SEQ ID NO 54
<211> LENGTH: 21
<212> TYPE: RNA
<213> ORGANISM: Oryza sativa

<400> SEQUENCE: 54
accgcuucau gaacuuucag g 21

<210> SEQ ID NO 55
<211> LENGTH: 21
<212> TYPE: RNA
<213> ORGANISM: Oryza sativa

<400> SEQUENCE: 55
caccugacuu cgcuaccauc u 21

<210> SEQ ID NO 56
<211> LENGTH: 21
<212> TYPE: RNA
<213> ORGANISM: Oryza sativa

<400> SEQUENCE: 56
uaaguauuuu gaaaggcugg a 21

<210> SEQ ID NO 57
<211> LENGTH: 21
<212> TYPE: RNA
<213> ORGANISM: Oryza sativa

<400> SEQUENCE: 57
aaggcaugaa gcaauguaac a 21

<210> SEQ ID NO 58
<211> LENGTH: 20
<212> TYPE: RNA
<213> ORGANISM: Oryza sativa

<400> SEQUENCE: 58
gaucaggcgc cucaaggauc 20

<210> SEQ ID NO 59
<211> LENGTH: 27
<212> TYPE: RNA
<213> ORGANISM: Oryza sativa

<400> SEQUENCE: 59
cugacuucgu cccucucaug aacguca 27

<210> SEQ ID NO 60
<211> LENGTH: 23
<212> TYPE: RNA
<213> ORGANISM: Oryza sativa

<400> SEQUENCE: 60
ugagcaacac uggauaugug acc 23

<210> SEQ ID NO 61
<211> LENGTH: 21
<212> TYPE: RNA
<213> ORGANISM: Zea mays

<400> SEQUENCE: 61
uccuugaggc gucugcuccu g 21

<210> SEQ ID NO 62
<211> LENGTH: 21
<212> TYPE: RNA
<213> ORGANISM: Zea mays

<400> SEQUENCE: 62
uugcacugcu ucaugccuuu c 21

<210> SEQ ID NO 63
<211> LENGTH: 21
<212> TYPE: RNA
<213> ORGANISM: Zea mays

<400> SEQUENCE: 63
ugggaguuca ugaagcgguc a 21

<210> SEQ ID NO 64
<211> LENGTH: 21
<212> TYPE: RNA
<213> ORGANISM: Zea mays

<400> SEQUENCE: 64
ugagagagug cacuuucucc c 21

<210> SEQ ID NO 65
<211> LENGTH: 21
<212> TYPE: RNA
<213> ORGANISM: Zea mays

<400> SEQUENCE: 65
caccugacuu cgcuaccauc u 21

<210> SEQ ID NO 66
<211> LENGTH: 62
<212> TYPE: RNA
<213> ORGANISM: Oryza sativa

<400> SEQUENCE: 66
aguccagcaa guuuugaaga ugauagaaaa uuugagcgcg ucguaguaac ugucguccac 60
ga 62

<210> SEQ ID NO 67
<211> LENGTH: 30
<212> TYPE: RNA
<213> ORGANISM: Oryza sativa

<400> SEQUENCE: 67
gaggaugaug gucacuauga ugugcugaaa 30

<210> SEQ ID NO 68
<211> LENGTH: 31
<212> TYPE: RNA
<213> ORGANISM: Oryza sativa

<400> SEQUENCE: 68
uuuauuuucg cuugguuucc ggcaaaaagg g 31

<210> SEQ ID NO 69
<211> LENGTH: 898
<212> TYPE: DNA
<213> ORGANISM: Oryza sativa

<400> SEQUENCE: 69
aatcttattc tacatatttc tatcttatat agaacaacta gcatagctct cgttgcccag 60
ccaggttgcc cagccaggtt gcctggtgca caatgagagc tggctagggc ggactcattc 120
tgctgttggt gcccaacgat gctagctgct actcatacta gtgaagcctg ccatggttct 180
gagaaatttt tggatactcc gctgcgtaga tatgcactaa aagcttgtat gtttcgctga 240
ctacatacta tggatatcac ctgtttgaca agagaaggat tacataccac gatgaagatg 300
aattggaaca tgatgcaagt gatgtagcgc cccatatagg agtcactcag gaaagcacag 360
aagagggaga agatgtagac ggtgcccatc cacatgctga cgctattggc ggcctcggcg 420
ttctcctggt ggagcacctg cctgaggaac accaccaggc ccacggcgac gccaaaaaat 480
gcaaagttgg ccaacacata gctcactgca tcgtcaagta gagctgctta atcactgagg 540
tatatacatt tagttcgcct tcttcagcgt tgccatggac ctggtgatgt tcttccggcg 600
ggtgccccac caagagaacg ccgtggccac caacaacatc agcatatgga tgggcaccat 660
cttcatcttt gccctcttta gtgctttccg tagtgattcc tatacggggt gctacttcac 720
ttggatcatg ttacaattta tcttcatcgt gatatatgct ccttctgttc tcacataggt 780
gatatcttaa aatgtatgag gcatatatac tttctaccta atattataaa gtatatgcct 840
ctatatagat caaataaagc agaaaagtca ttgttattac aaaaaaaaaa aaaaaaaa 898

<210> SEQ ID NO 70
<211> LENGTH: 892
<212> TYPE: DNA
<213> ORGANISM: artificial sequence
<220> FEATURE:
<223> OTHER INFORMATION: synthetic construct

<400> SEQUENCE: 70
ggtaccaatc ttattctaca tatttctatc ttatatagaa caactagcat agctctcgtt 60
gcccagccag gttgcccagc caggttgcct ggtgcacaat gagagctggc tagggcggac 120
tcattctgct gttggtgccc aacgatgcta gctgctactc atactagtga agcctgccat 180
ggttctgaga aatttttgga tactccgctg cgtagatatg cactaaaagc ttgtatgttt 240
cgctgactac atactatgga tatcacctgt ttgacaagag aaggattaca taccacgatg 300
aagatgaatt ggaacatgat gcaagtgatg tagcgcccca tataggagtc actcaggact 360
ccacggtcat tgtgtatcat gtagacggtg cccatccaca tgctgacgct attggcggcc 420
ttggtccttc atagagaccc aacctaacag tgaacgtact gtcgccccac ggcgacgcca 480
aaaaatgcaa agttggccaa cacatagctc actgcatcgt caagtagagc tgcttaatca 540
ctgaggtata tacatttagt tcgccttctt cagcgttgcc atggagcgac agaacgttca 600
cggttaggtt gtgtctcttt gaaggaccat ggccaccaac aacatcagca tatggatggg 660
caccatcttc atgatgaaca atgacggtgg agtccgtagt gattcctata cggggtgcta 720
cttcacttgg atcatgttac aatttatctt catcgtgata tatgctcctt ctgttctcac 780
ataggtgata tcttaaaatg tatgaggcat atatactttc tacctaatat tataaagtat 840

-continued atgcctctat atagatcaaa taaagcagaa aagtcattgt tattacgtta ac 892

<210> SEQ ID NO 71
<211> LENGTH: 21
<212> TYPE: DNA
<213> ORGANISM: artificial sequence
<220> FEATURE:
<223> OTHER INFORMATION: synthetic construct

<400> SEQUENCE: 71
tggtacaacg tcattgatga c 21

<210> SEQ ID NO 72
<211> LENGTH: 21
<212> TYPE: DNA
<213> ORGANISM: artificial sequence
<220> FEATURE:
<223> OTHER INFORMATION: synthetic construct

<400> SEQUENCE: 72
tggaccttac atggcccttc a 21

<210> SEQ ID NO 73
<211> LENGTH: 21
<212> TYPE: DNA
<213> ORGANISM: artificial sequence
<220> FEATURE:
<223> OTHER INFORMATION: synthetic construct

<400> SEQUENCE: 73
taattgtgca gctcatcacc c 21

<210> SEQ ID NO 74
<211> LENGTH: 21
<212> TYPE: DNA
<213> ORGANISM: artificial sequence
<220> FEATURE:
<223> OTHER INFORMATION: synthetic construct

<400> SEQUENCE: 74
tagatgggaa atatagatat c 21

<210> SEQ ID NO 75
<211> LENGTH: 21
<212> TYPE: DNA
<213> ORGANISM: artificial sequence
<220> FEATURE:
<223> OTHER INFORMATION: synthetic construct

<400> SEQUENCE: 75
tgcttatatg tatgttctgt a 21

<210> SEQ ID NO 76
<211> LENGTH: 21
<212> TYPE: DNA
<213> ORGANISM: artificial sequence
<220> FEATURE:
<223> OTHER INFORMATION: synthetic construct

<400> SEQUENCE: 76
tcaagagtct ttgaaagaaa g 21

<210> SEQ ID NO 77
<211> LENGTH: 880
<212> TYPE: DNA

<213> ORGANISM: artificial sequence
<220> FEATURE:
<223> OTHER INFORMATION: synthetic construct

<400> SEQUENCE: 77
aatcttattc tacatatttc tatcttatat agaacaacta gcatagctct cgttgcccag 60
ccaggttgcc cagccaggtt gcctggtgca caatgagagc tggctagggc ggactcattc 120
tgctgttggt gcccaacgat gctagctgct actcatacta gtgaagcctg ccatggttct 180
gagaaatttt tggatactcc gctgcgtaga tatgcactaa aagcttgtat gtttcgctga 240
ctacatacta tggatatcac ctgtttgaca agagaaggat tacataccac gatgaagatg 300
aattggaaca tgtggacctt acatggccct tcaatatagg agtcactcag gagtcatccg 360
tgacgttata ccagacatcc atatttccca tccactttct cttagagacc cttgtgggtg 420
atgagttgca cagttacctg cttatatgta tgttctgtac ccacggcgac gccaaaaaat 480
gcaaagttgg ccaacacata gctcactgca tcgtcaagta gagctgctta atcactgagg 540
tatatacatt tagttcgcct tcttcagcgt tgccatggat acagaaaata catatcagcg 600
ggtaattgtg cagctcatca ccctcaagag tctttgaaag aaagtagatg ggaaatatag 660
atatctggta caacgtcatt gatgactccg tagtgattcc tatactgaag ggccacgtaa 720
ggtgcacatg ttacaattta tcttcatcgt gatatatgct ccttctgttc tcacataggt 780
gatatcttaa aatgtatgag gcatatatac tttctaccta atattataaa gtatatgcct 840
ctatatagat caaataaagc agaaaagtca ttgttattac 880

<210> SEQ ID NO 78
<211> LENGTH: 21
<212> TYPE: RNA
<213> ORGANISM: Oryza sativa

<400> SEQUENCE: 78
gugagaaagu gcccucucuc a 21

<210> SEQ ID NO 79
<211> LENGTH: 2040
<212> TYPE: DNA
<213> ORGANISM: Oryza sativa

<400> SEQUENCE: 79
ccacgcgtcc gccaaaagtg aactgtgaac cggacgatcc aggcatccag ctaaccgctt 60
ccccctcgtc gcgctcgcgc cgcgccgcgc ctcgcctcca ccagctacgc cgtcacgcga 120
gctcacggcc cgggggcctc ggaagcacaa ccaccacgcg tccacgccga agccacgagg 180
agagcctgtc tctcctccgg ggattctatc gccggctggt ctcagcggcg ccacttggag 240
caggcggcac ccgctccgta ctgctgctga tttggtgagc gcgggcagcc gcgggatggg 300
agatctggtg gcgtgatggt gagcccgggc agtaaccggg gcggcctgtc gcgcgtatcg 360
acgcggggcg gcgtcgccgg gccggggagc ccgcgcgcct ctcctgccgc gaccgctttc 420
gcggcgctac ggcgcaggtg gcggtgggcg cccccgggct cgtcgacgct ggagcgcgcg 480
gcccgcgcgt tcctgctggc ctccgcagcg ctcgtgctct cctgcgcgct ctacctctac 540
gtgctgcgct acgtcggccg gggaggtcgc gccttcgccg ccgcgggctt cgtcggggac 600
gccgtcctgg gcctcggcgg cgagccgtgc gacgtgttcg acggcgcctg ggtgcccgac 660
gacaccggcc tccgcccgct ctacaatagc tccgggtgcc cgttcgctga gcgcgggttt 720
gactgcctcg ccaacgggcg gaacgacact gggtacctca agtggcggtg gaagccgcgc 780

-continued

```
cggtgcggcg tgccgcggtt tgcggcccgc accgcgctgg agcggctgcg cgggaagcgg    840

gtggtgttcg tgggggattc catgagccgc tcgcagtggg agtccttcat atgcatgctc    900

atggccggcg tggatgaccc caggacggtc ttcgaggtga acgggaacga gatcaccaag    960

acgatacgcc acctggcggt caggttcgcg tctcacggcc tcaccgtgga attcttccgg   1020

tccgtgttcc tcgtgcagga gcatcctgcc ccgcggcatg cccccaagag ggtcaaatcc   1080

actttgaggc ttgacaggat ggataatttc agccggaaat gggtcaattc ggacgtactg   1140

attttcaaca ctgggcattg gtggacaccg accaaattgt ttgatacggg ttgctatttt   1200

caggctggac gttctcttaa attaggtaca tccattgatg ctggtttcag gatggcactg   1260

gagacctggg cctcatgggt acaaaaaaga gttgatttaa accgaacaca tgtattcttt   1320

cgcacatatg agccatcgca ttggggggat acaagccaaa aggtgtgtga ggtaacagag   1380

cagccttcat cagaggccaa aggaaatgat aagagtgaat ttggggctat acttgctgat   1440

gttgtaacca acatgaaagt tcctatcaca gtactaaatg taactttaat gggatcgttt   1500

cgaagtgatg cacatgttgg cacttggagt tatcctccca ctatacttga ttgcagccac   1560

tggtgtcttc ctggagtccc tgatgcttgg aacgaactcg tgttttcgta ccttttgaca   1620

aatggttggc gaaacatggc gggctgaatt ttttggcagc acaatctacc cgcacctatt   1680

gcattgtgat atttgacatt accaggtata ctagagaatt aacatacgtc cgggacaagg   1740

cagctgcagc tgctaggtgg ttcactggac ttctacattc ttttcttctt tttgattttt   1800

gactcgtata cacggtgaag catgctacat gcaactagag ttgtatgtag ttggtaaggg   1860

attagaaggc cttggcattc gttctatttg ctcaatttac taacggttca ttttattatg   1920

ttgttaaaaa tcgagtttgt attgtaacct gtatgtacaa acatttactt gatacattgt   1980

gagaaagtgc cctctctcaa ttggattgat aaaaaaaaaa aaaaaaaaaa aaaaaaaaaa   2040
```

<210> SEQ ID NO 80
<211> LENGTH: 21
<212> TYPE: RNA
<213> ORGANISM: Oryza sativa

<400> SEQUENCE: 80

```
gggcgaaggu gaacucucuc a                                                21
```

<210> SEQ ID NO 81
<211> LENGTH: 2523
<212> TYPE: DNA
<213> ORGANISM: Oryza sativa

<400> SEQUENCE: 81

```
cggacgcgtg gggcgtgcgt ggtctccttc ctctcgtggc gacgaccgag cggccgtcgc     60

tgcttacgtg cccagtcctg ttcgtccctt cgccggcgac ggccacgacc tggttatagg    120

caaagtttgt cctgaactgt tcatcatggt ggaaggctgg gtattctctg ctttgttagt    180

ggtgtttcta gcgttcacaa caccttgcga gtcattctac ttgccaggta gttatatgca    240

cacatatcag caaggtgaag taataagggc gaaggtgaac tctctcactt ccattgagac    300

agaactaccc ttcagttact acagccttcc atactgtcgt cccagagatg ggttaagaa     360

gagtgctgaa aacttaggcg agcttctgat gggtgatcaa atagataatt ctccgtaccg    420

tttccgtgta aatgtcaacg aatctctgta tctgtgtact acaaccccac ttgacgaggc    480

taatgtgaag ctcctcaagc agcgtagcca tgatctatac caggtgaaca tgattcttga    540
```

-continued

```
caatcttcct gtgaggaggt tcacagagca gaatggaata accatccagt ggacaggcta    600
tccagttggt tatattccag aaggcacttc tgatgtctac atcatcaatc acctgaaatt    660
taaggtcttg gtccataagt atgaaggagg cgaagtaaag gtagttggga ctggggaagg    720
aatggaagtg atctcagaga ctgacaaaga tgccaattct ggatatgaga ttgtgggatt    780
tgaagttgtc ccatgcagcg tgaagcgtga tcctgaatcc atattgaagc ttaatatgta    840
tgataaagtc gatcctgtga actgccctgt ggagttggaa aaatctcaat tggttaggga    900
gaaagagaag attactttta cttatgaggt tgaatttgta aacagtgata tcaggtggcc    960
atcacggtgg gatgcatacc tgaagatgga gggttcgaag attcactggt tttcaattat   1020
gaactctttg atggtaattc tatttttggc tggcattgta tttgtcatat tcttgcgtac   1080
agtgaggagg gacttgactc ggtatgagga gttggataag gaggcccaag ctcagatgaa   1140
tgaggagctc tctggttgga agcttgttgt tggagatgtc ttcagagaac caacctcacc   1200
gaagctgctc tgtgtcatga ttggcgatgg ggttcagatt ttgggtatgg caattgttac   1260
cattttcttt gccgcatttg gcttcatgtc tcctgcatcg agaggaatgt tgttgacagg   1320
gatgatagtc ttttatatgt tacttggaat tgtgtctggg tatgctgctg tcaggctctg   1380
gaggacttta aaaggaacgt ccgagggatg gaggtctgtc tcctggtcaa ctgcttgttt   1440
cttccctggc attgtcttca ttgtcctcac tgtgttaaac ttcatgctgt ggacaagaaa   1500
tagtactgga gcccttccca tctcactttt ctttggcctt ttgtccttgt ggttctgtgt   1560
ctccgtgcca cttacccttt taggtggttt ctttggcaca agggctgagc caatagaatt   1620
ccctgttcga accaatcaga taccaagaga aatccctacg aagaagtact cattgctctt   1680
catacttggt gctggaactc taccttttgg aacactcttc atcgagctct tcttcattct   1740
ttctagtatt tggcttggaa ggttctatta cgtgtttggc ttcctccttg tcgtgcttct   1800
tttgctgatt gtggtgtgtg ctgaggtatc agttgttctt acctacatgc atctctgcgc   1860
ggaggactgg aggtggtggt ggaaagcttt ctttgcttct ggaacagtgg ccctttatgt   1920
gttcctttac tctatcaact acttggtgtt tgatctcaga agcttgagtg ggccagtttc   1980
tgctattctc tacattggat actctttcgt tgtctccctt gccattatgc tagcgactgg   2040
taccgttggc ttcctgacgt cgttctcttt tgtccactac cttttctcat cagtcaagat   2100
tgattgaaga tccagggttg tctttacaca aaatcacctg tgagctcaaa tgatatgacc   2160
attgcatctt gaaggccttt cacagagcag tgctgtttgt aatgtagctt attaccgaga   2220
gtctgagact gctgtacctt gtaatgaata gtatatttca gcagatgtgt tttgaagttt   2280
gtcacacttt gctacagcat tttgttgacc tgccaatact gtaggaaaag tcttgcgttt   2340
attatcccat ggtgccattt tgttgtctgt ttctttctgc aagattggct tgcagctgga   2400
gaactatacg ttcttatggt ataatctaca tgtgcaaaat gtttcccatc caaaaaaaaa   2460
aaaaaaatca gttcagaagt caccttcttt cgtgaatgtt ttgattccct gaggctactt   2520
tat                                                                 2523
```

<210> SEQ ID NO 82
<211> LENGTH: 21
<212> TYPE: RNA
<213> ORGANISM: Oryza sativa

<400> SEQUENCE: 82

```
gccagaaggu gcacugucuc a                                               21
```

<210> SEQ ID NO 83
<211> LENGTH: 530
<212> TYPE: DNA
<213> ORGANISM: Oryza sativa

<400> SEQUENCE: 83
gcagatgata gacacgacta aagattacat tcaagcgctg agcattgtgc cgacaagaga 60
gttggccttg cagacgtctc agattttcat cgaagtttca aagcacttga aagcccgcgt 120
gatggtgacc accggaggca cgaatttgaa ggacgacata atgcgtatat acgaaaacgt 180
tcacgttatc attgcgactc ccggtcgcat actcgatctg atggagaaga aggttgccaa 240
gatgaacaac tgtcaaatgc ttgttctcga cgaagccgac aaacttctgt ctcgggattt 300
ccaggggctc ctcgatcgag tcatctcgtt cttgccgcaa gaaagacaaa tccttctcta 360
ttcagctacg ttcccgatga ccgttgaaga attcatgcgc cgtcacctca agaacgccta 420
cgagatcaac cttatggagg agctcacact caagggagtg acacagtact acgctttcgt 480
acaggaacgc cagaaggtgc actgtctcaa cacgcttttc tcgaaacttc 530

<210> SEQ ID NO 84
<211> LENGTH: 20
<212> TYPE: RNA
<213> ORGANISM: Oryza sativa

<400> SEQUENCE: 84
ggaaggccua agcagugcaa 20

<210> SEQ ID NO 85
<211> LENGTH: 2229
<212> TYPE: DNA
<213> ORGANISM: Oryza sativa

<400> SEQUENCE: 85
atggcttcaa gggcggtcat cagaagaagg aagtatcttt tggatcatgt taacgcacct 60
accctctcat tgtccccctt ctctaccttc caacatggaa gatctggttc tgaggatgaa 120
tcaagaatcg gacagcgatt tcttgagcaa agctctgggg attccaaatg ggagcaaggg 180
cagtatggtg tgaaattgat aaagggagat ctactagccc ttggtaatgg gcttctgcgg 240
cgcccagccc atgggatttc tctacctgct tatggaattg gaaggaagga atttgggttg 300
cctatgggtg ctagacattt gctgcagtca gtccgcacag cctcaactgc aacagctggg 360
caacctaagt tggatattga agatgaacag agtgaggatc agaaacagaa caaaaggaaa 420
aaggaggcat ccccagaaga atgtgatcag gctgtggaag gcctaagcag tgcaaaagct 480
aaagccaaag ctaagcaggt acaagaatct gtaaaggctg gccaatcaat tgtacgaaaa 540
ttctgggcga ggcttctggg tattggtcct gctctccgag ctgttgcttc gatgagcaga 600
gctgattggg ctgcaaagct gaagcactgg aaggatgaat ttgtgtcaac gctgcagcat 660
tactggttag ggacaaagct actctgggca gatgtgagga tttcgtcaag attactggtg 720
aaacttgctg gtggaaagaa cctttcaaga agagagagac aacaactgac ccgtacaaca 780
gcagatatct tcaggctggt accttttgct gtgttcatca ttgttccatt catggagttc 840
ttacttccag tgttcctcaa gttatttcca aatatgcttc cctcaacttt ccaagacaag 900
atgaaagaag aggaagcgtt gaaaaggaaa ctgaaagcaa gaatggagta tgccaagttt 960
ttgcaagata ctgcaaaaga aatggcaaag gaagttcaaa catcacgtag tggagaaata 1020
aaacaaacag ccgaagatct tgatgaattt ttgaacaagg ttaggagagg tgaacatgtc 1080

-continued

```
tcaaatgatg aaatcttgaa cttcgcgaag ctgtttaatg atgagctgac tttggataac   1140
atgagcagac cacgcttggt aaacatgtgc aaatatatgg gtattcgacc tttcggtact   1200
gaccactact tgaggttcat gcttcgcaaa aaactgcaag acattaagaa tgacgataag   1260
atgattcaag ctgagggtgt tgagtctctc tctgaagagg aacttcggca agcctgtcgt   1320
gaacgtggtc acctaggttt gctgtcaaca gaagaaatgc gccaacagct ccgagattgg   1380
ttggatctct cacttaatca tgctgtgcca tcctctcttc tcatactttc aagagctttt   1440
accgtatctg ggaaaatgaa gcctgaggag gctgttgtag caaccttatc ttctctacca   1500
gatgaagttg tggatacagt tgggaccgta ttgccatctg aagattcggt ttctgagagg   1560
aggagaaaac tggaattcct tgagatgcag gaagaactta tcaaggagga agagaagaag   1620
aaagagaaag aagaaaaagc gaaacaagag aaagaagaaa aggccaaact caaagaacca   1680
aaggctgctg aagaagattt ggctttgaag gaaatgactg gtcctactgc tagggaagaa   1740
gaagaactga gagaagcaaa acagcacgat aaggaaaagc tctgtaattt tagtcgagca   1800
ctggctgtac tggcatccgc atcgtctgtt agcaaggagc gtcaagagtt cctcagcctt   1860
gtcaacaaag agattgaact gtataactct atgcttgaaa aggagggtac agaaggtgaa   1920
gaggaagcta agaaagctta catggctgct agagaagagt cggacaaggc tgctgaggtt   1980
gatgaagaag aaaaggtctc atcggcgctg attgagaagg ttgatgctat gctccagaaa   2040
ttagaaaagg agattgatga cgtggatgca caaattggaa accgatggca aattcttgat   2100
agggatcttg atggcaaggt gactcctgag gaggtagcgt cagcagcagc ttatctgaag   2160
gatacaatag gaaaggaagg cgtccaagag cttgtcagca acctctctaa agacaaaggt   2220
cctccctga                                                           2229
```

<210> SEQ ID NO 86
<211> LENGTH: 22
<212> TYPE: RNA
<213> ORGANISM: Oryza sativa

<400> SEQUENCE: 86

```
gaaauucaug gaagcagugc ag                                              22
```

<210> SEQ ID NO 87
<211> LENGTH: 1521
<212> TYPE: DNA
<213> ORGANISM: Oryza sativa

<400> SEQUENCE: 87

```
atggccgcct cctcttcctt cctcgccgcc ggccgccgcc tgatccgcct cggctgcggc     60
aggctcctcc ccgccggcca cgcgcgatcc catggctcca cccctgccct cattcgagcc    120
gccgccgccg cctcctcccc cgcctctcct cgcggccaca gcggggggag gaagccggcg    180
cggcccccga gcctgcagtc cacgctgtgg ccgctgggcc acccgggcac gctcctggtg    240
ccggagatcg agcggtgggc ggccaagcca ggcaaccgcc tccgccacgt cgagctcgag    300
cgcatcgtca aggagctccg caagcgacgc cgccaccgcc aggccctcga ggtctctgaa    360
tggatgaatg ccaagggaca tgtaaaattt ctgccaaagg atcacgctgt tcacctggat    420
ttgattggtg aaattcatgg aagcagtgca gccgagactt acttcaacaa cctgccagat    480
aaagataaga cagaaaaacc ctatggtgca cttcttaact gctacacacg ggaactcctg    540
gttgaaaaat cgttggctca ttttcagaag atgaaagagt tgggttttgt gttttccaca    600
ctcccctaca acaacatcat gggtctgtat acgaacctag ggcagcatga aaaggttcct    660
```

tcagtaattg cagagatgaa aagcaatggt atcgttcctg acaatttcag ctacagaata 720
tgcattaact cttatggcac aagggctgat tttttcggga tggaaaacac ccttgaagag 780
atggagtgtg aacctaaaat cgttgttgat tggaacacgt atgctgtcgt ggcaagcaac 840
tacattaagg gcaacataag ggagaaagca ttctctgcct taaagaaagc agaagcaaaa 900
ataaatataa aagattcaga ttcctataac cacctgattt ccttgtatgg acatctgggg 960
gacaaatcag aggtcaatag gctgtgggcg ctccaaatgt cgaactgcaa taggcatatt 1020
aataaggatt acactacaat gcttgcagtg ctcgtgaaac ttaatgagat tgaagaagct 1080
gaagtgttgc tgaaagagtg ggagtcgagc ggaaatgcat ttgacttcca agttccaaat 1140
gtcctgctca ctggataccg ccagaaggac ttgctggaca aggctgaggc acttctggat 1200
gatttcttga agaagggaaa gatgcctcct tcaaccagct gggcaattgt ggcagctggc 1260
tatgcggaga aaggtgatgc tgcgaaagca tatgagctga caaagaatgc cctatgtgta 1320
tatgctccaa atactggttg gatccctagg cctgggatga ttgagatgat acttaagtat 1380
cttggagatg aaggtgatgt cgaggaggtt gaaattttcg ttgatctgct gaaagttgct 1440
gtgccactga actcagatat gactgacgct ttgtcaaggg ctcgaatgag agaagaaaag 1500
aaggttaaag atgcagtgta a 1521

<210> SEQ ID NO 88
<211> LENGTH: 20
<212> TYPE: RNA
<213> ORGANISM: Oryza sativa

<400> SEQUENCE: 88
ggaaggccug aagcaugcaa 20

<210> SEQ ID NO 89
<211> LENGTH: 1980
<212> TYPE: DNA
<213> ORGANISM: Oryza sativa

<400> SEQUENCE: 89
cgtgcctttt ccgtcgtccc attcgccagg ggggaacggc aaagggcatc gtcgcaaaca 60
atcaagttcc acaaactcgc atctcatctg cttcgactcc accgaggact cccttctttc 120
ctcccactcc catctgctct cctcgccgcc acctgcgccg tcagagcacg gagcagtccg 180
cgaccacgct ttcgctgccg ctctccgaca ggcgacggag ccgcagctcc agtcgcagtc 240
ggctcccctg aattcgggct cgccaaatac cctccaatcg tctgcgtccg tcgtccggga 300
cttccggtgc aactgaatcc ggcaccacct gtgcggcctg tcatggcact tggaagagga 360
gggaggaagg actcaagagg ttaaggtacg gtatttatag atttggctga agaaactggt 420
tgttgctatt atgaagacta agacgagtag gagcttacag aagtctggga gaggtaacca 480
tgtccaagga gaagggccaa actgggttct tgttgctggc ggggttttgc ttagcacgct 540
ttcagtcaag gttgtgtgca aactaaagca gttgttagac gggaagcagc aaaataatac 600
tttcgaagct aaaggaaggc ctgaagcatg caagctgcat tcagatctct accggctcag 660
tgaccaaact ggctgctact actgtatgtc agggcttgca aatggtggag tggaagtcaa 720
gcaagcacca gcaagtcctg tacccaaatc agttgaatcc tcacttccac ttgtcaagat 780
acccacacca gaatcaagca aagagaacag cggtgttatg tggatatcct cacctgatcg 840
gctgaaagat cctcgaaggc catttcagta ctctaacagt tctggctctc cctgtgtttc 900

```
agaatcagga tctgacattt atggcaaaag agaggtcata cagaagctaa gacagcacct    960

caagaaacgt gatgagatga tcatggagat gcaaactcag attgctgatc ttaagaactc   1020

tcttaacatt caggtgacac agtccagcaa tctgcagtct caattggatg ctgccaatcg   1080

tgatctgttt gaatctgaac gagagattca gcatctaagg aagattattg cagatcattg   1140

tgtcacagaa gcactctctc atgataaacc tttgcaagct gcgcattggc agccagatgc   1200

cgcaaatggg cattctaatg gctatggtga tggttgtgtt gatgatgctg acctgcattg   1260

tattagcatc gagaagagga aggtagaagt agagagggtg gagatgctca agaaagaggt   1320

ggttgaactg aaggaagtca ttgagggaaa ggactttgtg cttcagagct acaaggaaca   1380

gaaggtggaa ctcttctcaa agatcaggga gttgcaggaa aagctctcag cacaagtgcc   1440

aatcatcttg taggatctat ctgtgatact ttttagaaga ttgaatctaa gcataatgtt   1500

gccatgtccc atgagcagca gagggggtcc cgcttcagtg aagattgcag aaggtcttgg   1560

catttggcaa tcgtcacgca tgccaaacac catgctagga tctttgtgga atgcttctct   1620

tttcctttga ggggagcttt gcataatgtt aggttgattt gtttctttct tggttgtcat   1680

aatgttaggt tggtttgctt tcttccttct tcaatatcta gcccttggtt gctcaaagtt   1740

tacaaaggga ttcttttttt cagttgctag gcctcaggta actcaattga acttcatact   1800

caagttgctg tacaggttct cagatttcag gagacacaga agtctgtact gtgcctctgc   1860

ctcctgtttc atgctttttt tttgttaagt gatctttgga atgttaggtc catgacattt   1920

ctactatgag atttgaagac tatggcattg cccttttttg tgaaaaaaaa aaaaaaaaaa   1980
```

<210> SEQ ID NO 90
<211> LENGTH: 21
<212> TYPE: RNA
<213> ORGANISM: Oryza sativa

<400> SEQUENCE: 90

```
uggcugcuac auggacuccc g                                                21
```

<210> SEQ ID NO 91
<211> LENGTH: 1125
<212> TYPE: DNA
<213> ORGANISM: Oryza sativa

<400> SEQUENCE: 91

```
atggccggag acacgacgaa gcccacggag tcagccatcg tcgggagcac ggtgaccggg     60

caccacctgc tccacatcga cggctactcc cacaccaagg accgcctccc caatggctgc    120

tacatggact cccgcccttt caccgtggga ggccatctat ggcgcatcgg atactacccc    180

aacggcgacg tcgccgacgc ctccgcgtac atggccgtct acccttccat cgacgagaac    240

gtcatcgtcg ccgtcaaggc ttttgccaag ttcagcttgt tcttcaacgg cgagcccacg    300

ccgccggcgt ttgtgcatac cacagagcca ttcgtgttca gcaggaaggg gatcgggtat    360

ggttttagca agtatgccga gagggagttg atggagggct cgatcgtgga cgacaagttc    420

accatcaggt gcgacgtcgg cgtctccacg gagctccgcg cggaggacag gccgccgtcg    480

gacttcgcgg cggtggtgcc gccgtccgac ctgcaccggc acctcggcga ccttctggac    540

tccaagcacg gcgccgacgt cacgttccag gtcggcggcg aggcgttccg cgcgcaccgg    600

tacgtcctcg cggcgcggtc gccggtcttc agggcggagc tgttcggcgc catgagggag    660

gccaccgccg cggccgccgc gtcgtcgtcg gactcggagg cgatccgcgt ggacgacatg    720

gaggcgccgg tgttctccgc tctgctccgc ttcgtgtaca ccgacgcgtt gccggcgccc    780
```

ggcggagcgg acgacggaca agcggcagga ggaggatcgt attcggagga ggccgccatg 840
gctcagcacc tgctcgtcgc ggcggacagg tacgacctga agaggctgaa gctgctctac 900
gaagacaagc tacgcaggca catcgaagcc gcctccgccg cctccatgct cgcgttggtt 960
gagcagcacc attgccgagg cctcaaggag gcgtgcttgg tgttcctcag ctcgccggcc 1020
aaccttcacg ccgccatggg aagcgatgga tttgagcatt tatccaggag ctgcccccggt 1080 gtgatcaagg agctaatatc caaacttgtt ccacgttgtg attag 1125

<210> SEQ ID NO 92
<211> LENGTH: 21
<212> TYPE: RNA
<213> ORGANISM: Oryza sativa

<400> SEQUENCE: 92
aggccuuuuc augaacuccc a 21

<210> SEQ ID NO 93
<211> LENGTH: 578
<212> TYPE: DNA
<213> ORGANISM: Oryza sativa

<400> SEQUENCE: 93
tggcgcggac tcatggggaa cggtgacgcg cctcctgtct tgttttcctt tcatggcgcc 60
gaccctcgcc gacgggtgat cgacgtcgcc cctattcatc tgcttgatgg tcccgcccca 120
tacgccgatg ctcacgcacc tcctccttct atctccttac agacgcgggg acgctcgccc 180
acggcggcgg cgggagctga gtcttctgtc agcacgctcc tcgaggtgcg cggactcacc 240
gaatacgtga aggagactgg gcagctgaat cctagccggc gatcacctta ccatccgcga 300
gggcgagatt catgctatta tggggaagaa cggctgcggc aagagcaacc ctcacaaaag 360
gtctcactgg gcagtctcat tatgaggtga cgggtggcac cattctcgtg gaggggggg 420 acctggttga catggagcca tatgacagac ctctagcagg ccttttcatg aactcccaag 480
cacctatgtg agattcctga atcaacaatt tcgattttgt gctatggctg cgaatgctcg 540
ctaagaaagg aatggtctac cagcattggg ggcccttg 578

<210> SEQ ID NO 94
<211> LENGTH: 21
<212> TYPE: RNA
<213> ORGANISM: Oryza sativa

<400> SEQUENCE: 94
ggcgcucgcc uucgcaacca u 21

<210> SEQ ID NO 95
<211> LENGTH: 1188
<212> TYPE: DNA
<213> ORGANISM: Oryza sativa

<400> SEQUENCE: 95
atgaggcaca agcagaagac ccctccctgc acagtgcaca cgatactagc tagcccgatg 60
gccccaacct ccagcgttca ccgcgaaggc ggcagcgccg ccatggacat ggccgagctc 120
atccccacgc tgccgctgga gacggggagc ccgccgttcc cgctccggca atacggcggc 180
tactggctgc cggagtgggt cctccctggg ctcgaggccg tgcacacgcg cttcgagccg 240
aggccatccg acgtcttcct cgccagcttc cccaagtccg gcaccacctg gctcaaggcg 300

-continued

```
ctcgccttcg caaccatcaa ccggaccacc tacccgccgt ccggcgacgc ccacccgctc    360

cgccatcgcg gcccgcacga ctgcgtcaag ttcttcgagt ccaccttcgc catctccggc    420

gagggcggcg gcggagacgt ggacgtgttc gccgccctcc cgtcgccgcg cgcggttgct    480

cgcccgggga cgtgttcgcc gccctcccgt cgccgcgcgc ggttgctcgc cactcacatc    540

ccctactccc tcctgccgga gcgcatcacg tcggcggcgg cggacgacgg cgactccggt    600

tgccggatcg tgtacgtctg ccgggacccc aaggacgcgt tcgtctccat gtggctgttc    660

accatgagca acatggtgaa gggtgtcaca acgaccacgg acgaacacca cccggcggcg    720

gcggcggcgg cgccatcgat cgagcaggtg ttcgacctgt tctgcgacgg gcggagcatc    780

gctgggccgc agtggcacca cgtccgcgag tactgggagg agagccggag gcggccggag    840

aaggtcctct tcctccggta cgaggagatg ctgcgcgagc cggcgcgcaa cgtggagagg    900

ctcgccgagt tcctgcggtg cccgttcacc gccggcgagg tggcggccgg ggtggtggac    960

gccatcgtcg acctatgcag catcgaccga ctcaggaacg tgcaggcgaa caagaccggg   1020

gtgaccgacc tggcggtgaa gaaggagagc ttcttccgga gaggggtggc cggcgactgg   1080

agcaaccaca tgtcgccgga gatggcgtcg cggctggaca gggtcgtcga ggacgcgctg   1140

cgaggctccg ggttcacctt tgccgccgct gccggcgact ccgaatga                1188
```

<210> SEQ ID NO 96
<211> LENGTH: 21
<212> TYPE: RNA
<213> ORGANISM: Oryza sativa

<400> SEQUENCE: 96

```
ggcccaugac uuugcaacca c                                               21
```

<210> SEQ ID NO 97
<211> LENGTH: 1197
<212> TYPE: DNA
<213> ORGANISM: Oryza sativa

<400> SEQUENCE: 97

```
atggccgcgg ccgtcgtcct cctccgccgc ctgcgcggcg tcacggcggc gccccggcgc     60

gcggcggcgg cgctgcccct gaccacgagc gtccggggtg tctccgattc gacggagccg    120

ctcaccatcg agacctcggt cccctacaag tcccacatcg tggacccgcc cccgcgcgag    180

gtggccacca cggcgcgcga gctcgccacc ttcttccgcg acatgtccgc catgcgccgc    240

gcggagatcg cggcggactc gctgtacaag gcgaagctga tccgcggctt ctgccacctc    300

tacgacggac aggaggccgt cgcggtgggc atggaggcgg ccaccacccg cgccgacgcc    360

atcatcacgg cctaccgcga ccactgcgcc tacctcgccc gcggcggcga cctcgccgcc    420

ctcttcgccg agctcatggg ccgccgcggc gggtgctcca gggggaaagg cgggtcgatg    480

cacctgtaca agaaggacgc caacttctat ggcggccatg gcatcgtggg cgcgcaggtg    540

ccgctcggat gcggcctcgc gttcgcgcag aggtacagga aggaggccgc cgtcacgttc    600

gacctctacg gcgacggcgc cgccaaccag ggcagctgt tcgaggcgct caacatggcg     660

gcgctctgga agctgcccgt cgtgctcgtc tgcgagaaca accactatgg gatggggacg    720

gcggaatgga gggcatcgaa aagccccgca tactacaaac gcggcgacta tgtgccagga    780

ttgaaggtcg atggtatgga tgttcttgca gtcaaacaag cttgtaaatt tgccaagcaa    840

catgctcttg aaaatggacc gattattctt gagatggaca cctacagata ccacggacac    900

tctatgtcag atccagggag cacttaccgc accagagatg aaattgcagg cataagacag    960
```

-continued

```
gagcgcgatc caattgaaag ggttaggaag ctactactgg cccatgactt tgcaaccaca   1020

caagaactca aggacatgga gaaagaaata aggaagcaag tcgacactgc catcgcgaaa   1080

gcaaaggaaa gtccaatgcc cgatccatct gagctcttta caaatgtata tgttaatgac   1140

tgcggtttgg agtcatttgg tgtggacagg aaggtggtga gaactgtact tccctag      1197
```

PHASED SMALL RNAS

CROSS-REFERENCE TO RELATED APPLICATIONS AND INCORPORATION OF SEQUENCE LISTINGS

This application is a continuation of U.S. patent application Ser. No. 13/775,477 filed Feb. 25, 2013, which is a continuation of U.S. patent application Ser. No. 11/897,611 filed Aug. 31, 2007 (U.S. Pat. No. 8,404,928) which claims the benefit of priority to U.S. Provisional Patent Application No. 60/841,608 filed on Aug. 31, 2006, which is incorporated by reference in its entirety herein. A computer readable form of a sequence listing is filed with this application be electronic submission and is incorporated into this application by reference in its entirety. The sequence listing is contained in the file named P34147US03_SEQ.txt, which is 57,331 bytes in size (measured in operating system MS windows) and was created on Feb. 23, 2016.

FIELD OF THE INVENTION

This invention discloses recombinant DNA constructs and phased small RNAs useful in regulating expression of one or more genes of interest. Also disclosed by this invention are non-natural transgenic plant cells, plants, and seeds containing a recombinant DNA construct of this invention.

BACKGROUND OF THE INVENTION

Methods of gene suppression include use of anti-sense, co-suppression, and RNA interference. Anti-sense gene suppression in plants is described by Shewmaker et al. in U.S. Pat. Nos. 5,107,065, 5,453,566, and 5,759,829. Gene suppression in bacteria using DNA which is complementary to mRNA encoding the gene to be suppressed is disclosed by Inouye et al. in U.S. Pat. Nos. 5,190,931, 5,208,149, and 5,272,065. RNA interference or RNA-mediated gene suppression has been described by, e.g., Redenbaugh et al. in "Safety Assessment of Genetically Engineered Fruits and Vegetables", CRC Press, 1992; Chuang et al. (2000) *PNAS,* 97:4985-4990; and Wesley et al. (2001) *Plant* 1, 27:581-590.

Several cellular pathways involved in RNA-mediated gene suppression have been described, each distinguished by a characteristic pathway and specific components. See, for example, the reviews by Brodersen and Voinnet (2006), *Trends Genetics,* 22:268-280, and Tomari and Zamore (2005) *Genes & Dev.,* 19:517-529. The siRNA pathway involves the non-phased cleavage of a double-stranded RNA to small interfering RNAs ("siRNAs"). The microRNA pathway involves microRNAs ("miRNAs"), non-protein coding RNAs generally of between about 19 to about 25 nucleotides (commonly about 20-24 nucleotides in plants) that guide cleavage in trans of target transcripts, negatively regulating the expression of genes involved in various regulation and development pathways; see Ambros et al. (2003) *RNA,* 9:277-279. Plant miRNAs have been defined by a set of characteristics including a paired stem-loop precursor that is processed by DCL1 to a single specific ~21-nucleotide miRNA, expression of a single pair of miRNA and miRNA* species from the double-stranded RNA precursor with two-nucleotide 3' overhangs, and silencing of specific targets in trans. See Bartel (2004) *Cell,* 116:281-297; Kim (2005) *Nature Rev. Mol. Cell Biol.,* 6:376-385; Jones-Rhoades et al. (2006) *Annu. Rev. Plant Biol.,* 57:19-53; Ambros et al. (2003) *RNA,* 9:277-279. In the trans-acting siRNA ("ta-siRNA") pathway, miRNAs serve to guide in-phase processing of siRNA primary transcripts in a process that requires an RNA-dependent RNA polymerase for production of a double-stranded RNA precursor; trans-acting siRNAs are defined by lack of secondary structure, a miRNA target site that initiates production of double-stranded RNA, requirements of DCL4 and an RNA-dependent RNA polymerase (RDR6), and production of multiple perfectly phased ~21-nt small RNAs with perfectly matched duplexes with 2-nucleotide 3' overhangs (see Allen et al. (2005) *Cell,* 121:207-221).

This invention discloses a novel pathway for RNA-mediated gene suppression, based on an endogenous locus termed a "phased small RNA locus", which transcribes to an RNA transcript forming a single foldback structure that is cleaved in phase in vivo into multiple small double-stranded RNAs (termed "phased small RNAs") capable of suppressing a target gene. In contrast to siRNAs, a phased small RNA transcript is cleaved in phase. In contrast to miRNAs, a phased small RNA transcript is cleaved by DCL4 or a DCL4-like orthologous ribonuclease (not DCL1) to multiple abundant small RNAs capable of silencing a target gene. In contrast to the ta-siRNA pathway, the phased small RNA locus transcribes to an RNA transcript that forms hybridized RNA independently of an RNA-dependent RNA polymerase and without a miRNA target site that initiates production of double-stranded RNA. Novel recombinant DNA constructs that are designed based on a phased small RNA locus are useful for suppression of one or multiple target genes, without the use of miRNAs, ta-siRNAs, or expression vectors designed to form a hairpin structure for processing to siRNAs. Furthermore, the recognition sites corresponding to a phased small RNA are useful for suppression of a target sequence in a cell or tissue where the appropriate phased small RNA is expressed endogenously or as a transgene.

SUMMARY OF THE INVENTION

In one aspect, this invention provides a recombinant DNA construct encoding a transcript that folds into hybridized RNA that is cleaved in phase in vivo into multiple small double-stranded RNAs ("phased small RNAs") for gene suppression, preferably wherein the hybridized RNA is produced independently of an RNA-dependent RNA polymerase and is cleaved in phase in vivo by DCL4 or a DCL4-like ribonuclease (such as a DCL4 orthologue from any monocot or dicot plant).

Another aspect of this invention provides a recombinant DNA construct including DNA that transcribes to: (a) a first series of contiguous RNA segments, and (b) a second series of contiguous RNA segments, wherein the first series of contiguous RNA segments hybridize in vivo to the second series of RNA segments to form hybridized RNA that is cleaved in phase in vivo into multiple small double-stranded RNAs ("phased small RNAs") for gene suppression.

In a further aspect, this invention provides a recombinant DNA construct including a promoter operably linked to DNA that transcribes to RNA including: (a) at least one exogenous recognition site recognizable by a phased small RNA expressed in a specific cell of a multicellular eukaryote, and (b) target RNA to be suppressed in the specific cell, wherein the target RNA is to be expressed in cells of the multicellular eukaryote other than the specific cell.

Other aspects of this invention are methods of use of the recombinant DNA constructs of this invention for providing protection to plants from pests or pathogens, as well as non-natural transgenic plant cells, plants, and seeds containing in their genome a recombinant DNA construct of this invention. Other specific embodiments of the invention are disclosed in the following detailed description.

BRIEF DESCRIPTION OF THE DRAWINGS

FIG. 2 depicts a non-limiting example of a genomic DNA sequence (SEQ ID NO. 9) including the cDNA sequence, intronic sequence, and foldback arms which transcribe to hybridized RNA of this invention, as described in Example 1.

FIG. 3 depicts results of gene silencing in maize embryos (panel A) using a recombinant DNA construct including DNA that transcribes to RNA containing a recognition site corresponding to at least one phased small RNA of this invention, as described in Example 2. pMON94320 sequence in panel B corresponds to SEQ ID NO:12, including an insertion site (in bold) located between the GUS coding sequence and the Hsp 17 terminator. pMON100574 sequence in panel C includes the partial sequence of SEQ ID NO:13, which contains SEQ ID NO:6 incorporated in the sense orientation (underlined) at the insertion site of SEQ ID NO:12. pMON100575 sequence in panel D includes the partial sequence of SEQ ID NO:14, which contains SEQ ID NO:6 incorporated in the anti-sense orientation (underlined) at the insertion site of SEQ ID NO:12. pMON100576 sequence in panel E includes the partial sequence of SEQ ID NO. 15, which contains SEQ ID NO:5 and SEQ ID NO:6, both incorporated in the anti-sense orientation (underlined) at the insertion site of SEQ ID NO:12.

FIG. 8A depicts the transcript corresponding to a precursor cloned from the Os06g21900 phased sRNA locus. This precursor contained the phased small RNAs distributed between two regions along the transcript. FIG. 8B depicts the two exons (Exons 2 and 3, indicated by the shaded regions) contained within this locus and that form a long, imperfect foldback structure containing eight 21-nucleotide phased small RNAs, separated by an ~1.2 kB intron. FIG. 8C depicts results of Southern blot analysis confirming that expression of the phased small RNA from the Os06g21900 phased sRNA locus is found in rice grain but not rice seedlings or in other plant species tested. FIG. 8D depicts results of Southern blot analysis of transformed *Arabidopsis thaliana* Columbia (Col-0) ecotype and mutants dcl1-7 and dcl4-1; the blot was analyzed with probes corresponding to phased small RNAs "P7" (SEQ ID NO. 6), and "P5" (SEQ ID NO. 4), a canonical miRNA (miR173) and a trans-acting siRNA (ta-siR255). These results demonstrate that the Os06g21900 phased small RNA locus was efficiently processed in a dicot plant and required DCL4, not DCL1, to be cleaved in phase.

FIG. 9 depicts the hybridized RNA structures predicted from transcripts of a naturally occurring phased small RNA locus and a synthetic phased small RNA locus, as described in Example 7. FIG. 9A depicts the foldback structure of the transcript of the endogenous Os06g21900 phased small RNA locus (SEQ ID NO. 69); FIG. 9B depicts the foldback structure of the synthetic phased small RNA precursor encoded by SEQ ID NO. 77.

DETAILED DESCRIPTION OF THE INVENTION

Unless defined otherwise, all technical and scientific terms used have the same meaning as commonly understood by one of ordinary skill in the art to which this invention belongs. Generally, the nomenclature used and the manufacture or laboratory procedures described below are well known and commonly employed in the art. Conventional methods are used for these procedures, such as those provided in the art and various general references. Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art. Where a term is provided in the singular, the inventors also contemplate aspects of the invention described by the plural of that term. The nomenclature used and the laboratory procedures described below are those well known and commonly employed in the art. Where there are discrepancies in terms and definitions used in references that are incorporated by reference, the terms used in this application shall have the definitions given. Other technical terms used have their ordinary meaning in the art that they are used, as exemplified by a variety of technical dictionaries. The inventors do not intend to be limited to a mechanism or mode of action. Reference thereto is provided for illustrative purposes only.

Figure 1:
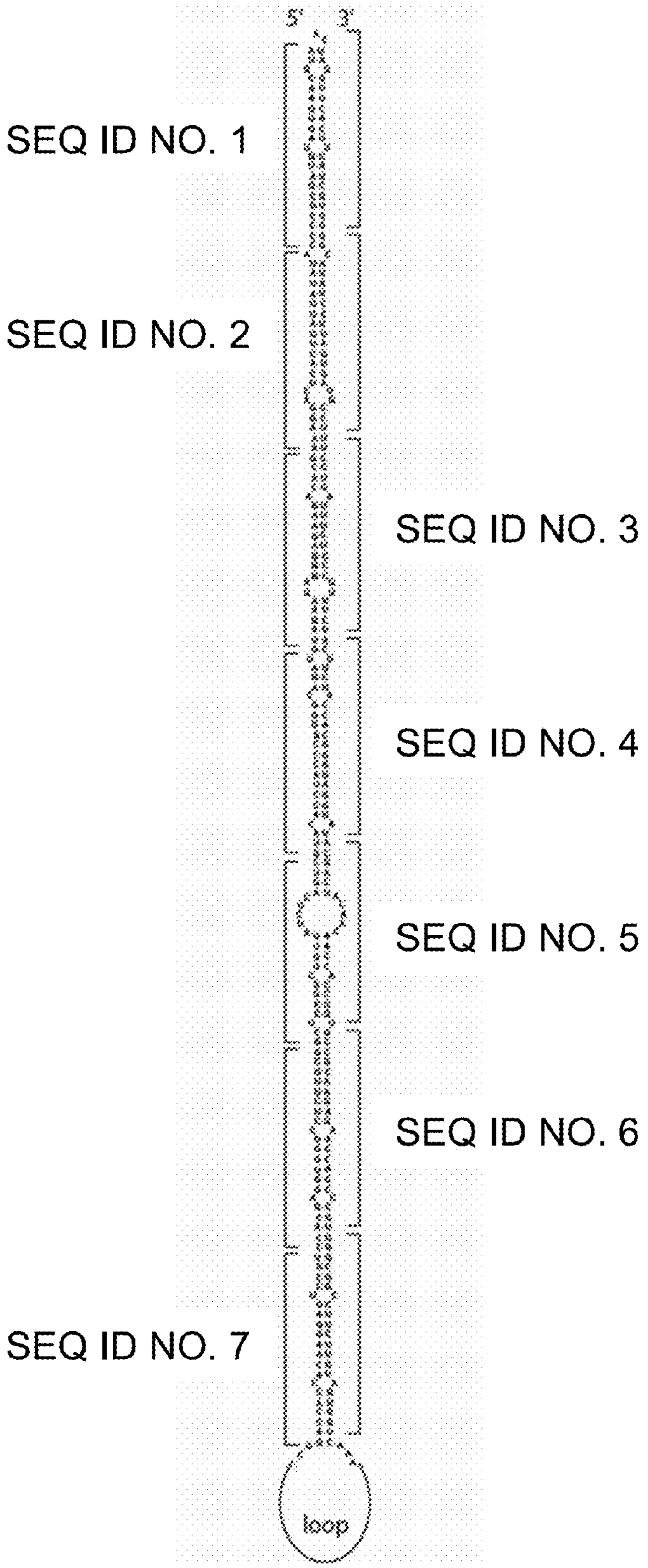
FIG. 1 depicts a non-limiting hybridized RNA that is cleaved in phase in vivo into multiple small double-stranded RNAs ("phased small RNAs") of this invention, as described in Example 1.
Figure 5:
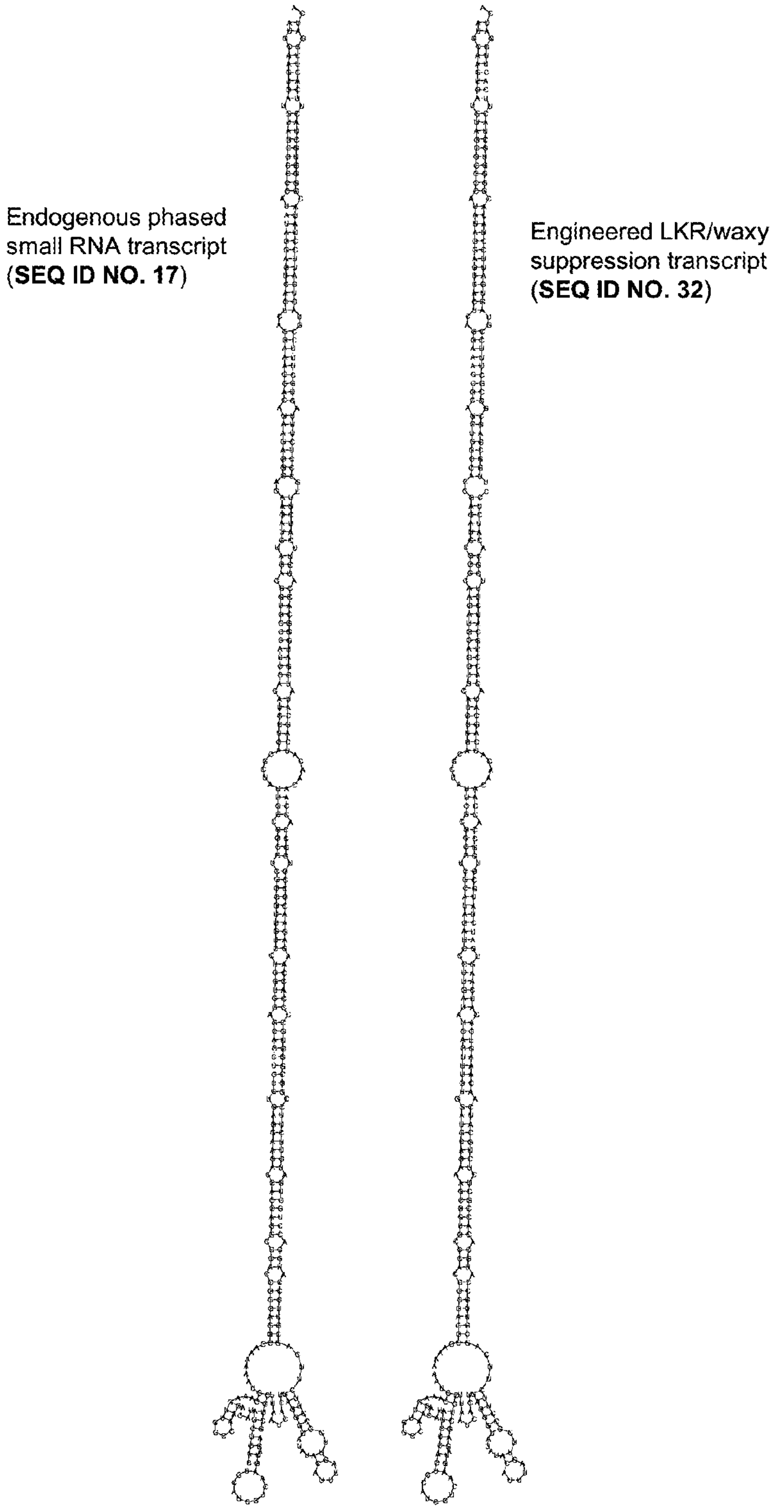
FIG. 5 depicts the predicted secondary structure of a phased small RNA template sequence (SEQ ID NO. 17) based on an endogenous phased small RNA locus, and of an engineered gene suppression construct (SEQ ID NO. 32) that is designed to suppress multiple target genes, as described in Example 3.
Figure 6:
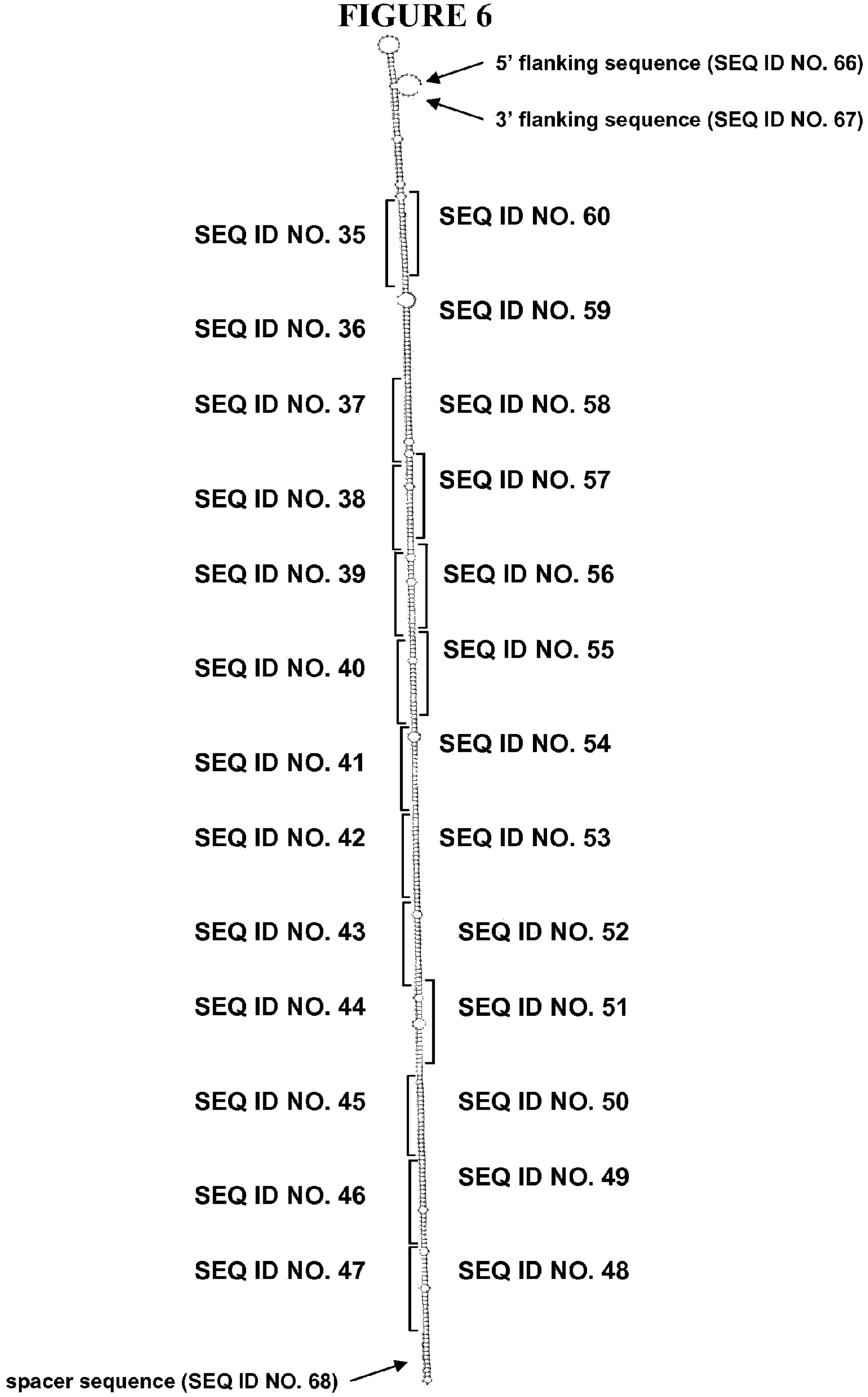
FIG. 6 depicts the RNA transcript (SEQ ID NO. 34) containing hybridized RNA in a single foldback structure predicted from an endogenous phased small RNA locus (LOC_Os12g42380.1|11982.m08017) having the sequence of SEQ ID NO. 33, as described in Example 4. This locus was identified from rice mature grain and seedling, and contained the phased small RNAs listed in Table 4. The transcript (SEQ ID NO. 34) includes 5' flanking sequence (SEQ ID NO. 66) and 3' flanking sequence (SEQ ID NO. 67), and a spacer sequence (SEQ ID NO. 68), located between the 5' and 3' arms of the foldback structure. The 5' and 3' termini of the transcript are indicated at the top of the figure; at the bottom of the figure, the transcript is shown to have a compact turn or loop of only 3 nucleotides.
Figure 8:
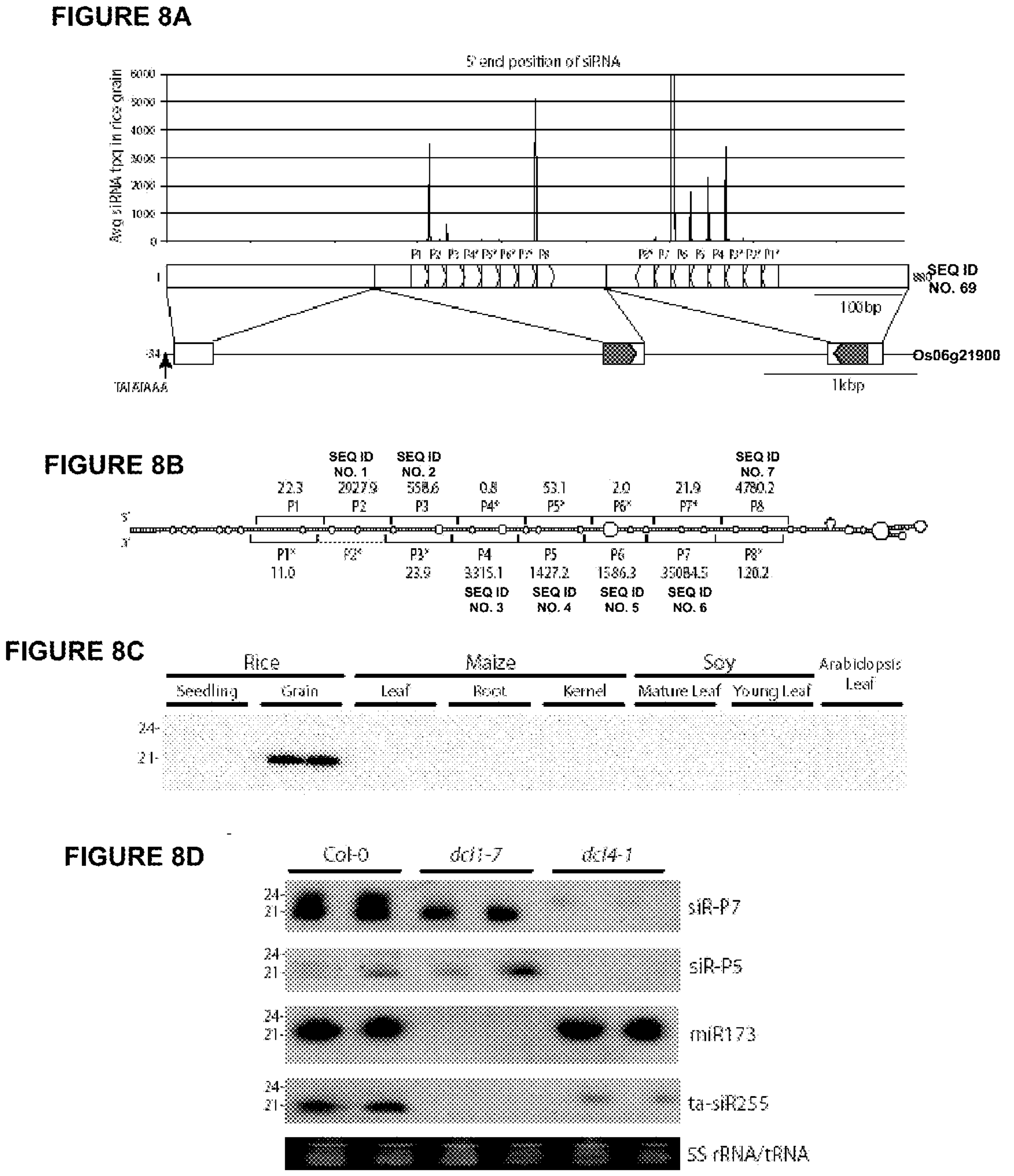
FIG. 8 depicts results of studies further characterizing the Os06g21900 phased small RNA locus, as described in Example 5.

Recombinant DNA Construct Encoding a Transcript that Folds into Hybridized RNA that is Cleaved in Phase In Vivo This invention provides a recombinant DNA construct encoding a transcript that folds into hybridized RNA that is cleaved in phase in vivo into multiple small double-stranded RNAs for gene suppression. By "hybridized RNA" is meant RNA that has undergone Watson-Crick base-pairing between strands of RNA that are substantially complementary, thus forming RNA that is substantially, but preferably not completely, base-paired or annealed between strands;

this is in contrast to conventional siRNA production from two perfectly or near-perfectly base-paired strands that form fully double-stranded RNA. In one preferred embodiment, "hybridized RNA" includes two single strands of RNA that are part of a single molecule, where the two single strands are substantially complementary and arranged anti-parallel to each other, thus allowing the two single strands to base-pair to each other; formation of the hybridized RNA occurs by intramolecular base-pairing. In an alternative embodiment, "hybridized RNA" includes two single strands of RNA that each are part of a separate molecule; formation of the hybridized RNA occurs by intermolecular base-pairing. In a particularly preferred embodiment, the recombinant DNA encodes an RNA transcript that forms a fold-back structure including two anti-parallel single-stranded arms, wherein one arm is substantially but not perfectly complementary with the other arm, and base-pairing between the two arms of the foldback structure results in substantially but not perfectly double-stranded RNA that includes mismatches; preferably the mismatches are distributed along the length of the hybridized RNA (such as at least one mismatch within a given segment of 21 contiguous nucleotides), such as is depicted in FIG. 1, FIG. 6, and FIG. 8B. Thus, in one preferred embodiment of this invention, the hybridized RNA includes a structure derived from a transcript of a naturally occurring phased small RNA locus, such as a structure selected from the structures depicted in FIG. 1, FIG. 5, FIG. 6, and FIG. 8B.

The hybridized RNA is produced independently of an RNA-dependent RNA polymerase; this is in contrast to trans-siRNA production wherein double-stranded RNA is formed through the action of an RNA-dependent RNA polymerase that synthesizes a complementary strand using the original RNA transcript as a template. Preferably, the nucleotides that form the hybridized RNA are nucleotides of the original RNA transcript (the "plus" strand) transcribed from the recombinant DNA construct, and not nucleotides on a second RNA molecule such as one (the "minus" strand) formed by the action of an RNA-dependent RNA polymerase on the original RNA transcript.

By "cleaved in phase" in vivo is meant that the hybridized RNA is enzymatically processed or "cut" in vivo into shorter segments wherein the site of cleavage is not randomly distributed along the hybridized RNA. The hybridized RNA is processed in vivo by a ribonuclease into multiple, shorter, substantially (but preferably not perfectly) double-stranded segments, that is to say, multiple small substantially double-stranded RNAs, which are arranged in a contiguous fashion, such as is depicted in FIG. 1, FIG. 6, and FIG. 8B; this is in contrast to canonical microRNAs, wherein there is substantial accumulation of only a single mature microRNA from the precursor transcript. The ribonucleotide cleaves the hybridized RNA non-randomly, resulting in a frequency distribution of the multiple small double-stranded RNAs that is phased; this is in contrast to conventional siRNA production wherein the site of cleavage does not result in a phased frequency distribution of siRNAs. Preferably the phasing of this frequency distribution is about 21 nucleotides, such as is depicted in FIG. 7. Thus, the multiple small double-stranded RNAs produced from a recombinant construct of this invention are termed "phased small RNAs". The term "phased small RNAs" is also applied to a single strand of the pair of strands that forms a given small double-stranded RNA produced from a recombinant construct of this invention; in a preferred embodiment, one strand of the pair accumulates to a greater level than the other.

In a preferred embodiment, the hybridized RNA is cleaved in phase in vivo by a ribonuclease other than a DCL1 ribonuclease. In a most preferred embodiment, the hybridized RNA is cleaved in phase in vivo by DCL4 or a DCL4-like ribonuclease (such as a DCL4 orthologue from any monocot or dicot plant, such as, but not limited to, plants of commercial or agricultural interest, such as crop plants (especially crop plants used for human food or animal feed), wood-, fiber-, pulp-, or cellulose-producing trees and plants, vegetable plants, fruit plants, and ornamental plants, such as those listed below under the heading "Making and Using Transgenic Plant Cells and Transgenic Plants") into multiple small double-stranded RNAs ("phased small RNAs") for gene suppression.

In a preferred embodiment hybridized RNA is cleaved in phase in vivo to at least three small double-stranded RNAs ("phased small RNA"). Various embodiments encompassed by this invention include recombinant DNA constructs that give rise to 3, 4, 5, 6, 7, 8, 9, 10, 11, 12, 13, or even more phased small RNAs, respectively.

Each phased small RNA is contiguous to the next; non-limiting examples of this arrangement are depicted in FIG. 1, FIG. 6, and FIG. 8B. Each phased small RNA includes two anti-parallel RNA segments, each of which contains from about 20 to about 27 nucleotides (e.g., 20, 21, 22, 23, 24, 25, 26, or 27 nucleotides). The base-pairing between the two anti-parallel RNA segments is sufficient for them to form a substantially double-stranded RNA. In a preferred embodiment, each small double-stranded RNA or phased small RNA includes at least one mismatch. A mismatch generally includes one or more non-base-paired nucleotides (on either or on both segments), forming a "bump" or "bulge" or "loop" within the otherwise base-paired double-stranded RNA. In a preferred embodiment, each phased small RNA includes one or more unpaired bases forming an overhang at one or at both ends; most preferably the overhang is a 2-nucleotide overhang such as is depicted in FIG. 1, FIG. 6, and FIG. 8B.

Each phased small RNA preferably is capable of suppressing a target gene. In one embodiment, the gene suppression by the phased small RNAs is of one target gene; for example, each phased small RNA suppresses the same segment of a single target gene or different segments of a single target gene. In another embodiment, the gene suppression by the phased small RNAs is of multiple target genes. While the inventors do not limit themselves to any single mechanism of action, it is most preferred that one of the two anti-parallel strands that makes up each phased small RNA is substantially complementary, or near perfectly complementary, or even perfectly complementary, to a target gene or sequence, as described below under the heading "Target Genes", which also provides a detailed discussion of suitable target genes.

In a preferred embodiment of this invention, the recombinant DNA construct includes a nucleotide sequence derived from a phased small RNA template sequence selected from the group consisting of SEQ ID NO. 8, SEQ ID NO. 9, SEQ ID NO. 17, SEQ ID NO. 33, the DNA sequence encoding SEQ ID NO. 34, and SEQ ID NO. 69, wherein at least one segment of 21 contiguous nucleotides in the phased small RNA template sequence is modified to suppress a target gene (that is, modified to suppress a gene other than the native target of the native phased small RNA). In a preferred embodiment of this invention, the recombinant DNA construct includes a nucleotide sequence derived from a phased small RNA template sequence selected from the group consisting of SEQ ID NO. 8, SEQ ID NO. 9, SEQ ID NO. 17, SEQ ID NO. 33, the DNA sequence encoding SEQ ID NO. 34, and SEQ ID NO. 69, wherein multiple segments of about 20 to about 28 (e.g., 20, 21, 22, 23, 24, 25, 26, 27, or 28) contiguous nucleotides are modified such that the transcript is cleaved in phase in vivo to multiple synthetic phased small RNAs that suppress a target gene.

In another preferred embodiment of this invention, the recombinant DNA construct includes at least one nucleotide sequence selected from the group consisting of SEQ ID NO. 18, SEQ ID NO. 23, SEQ ID NO. 27, the DNA sequence encoding SEQ ID NO. 66, the DNA sequence encoding SEQ ID NO. 67, and the DNA sequence encoding SEQ ID NO. 68.

A Recombinant DNA Construct Transcribing to a First and Second Series of Contiguous RNA Segments that Form Hybridized RNA that is Cleaved in Phase In Vivo Another aspect of this invention provides a recombinant DNA construct including DNA that transcribes to: (a) a first series of contiguous RNA segments, and (b) a second series of contiguous RNA segments, wherein the first series of contiguous RNA segments hybridize in vivo to the second series of RNA segments to form hybridized RNA that is cleaved in phase in vivo into multiple small double-stranded RNAs ("phased small RNAs") for gene suppression. This recombinant DNA construct can include a naturally occurring phased small RNA locus, such as is described in this disclosure, or can include a non-naturally occurring, synthetic sequence. Most preferably, the hybridized RNA is cleaved in phase by DCL4 or a DCL4-like ribonuclease (such as a DCL4 orthologue from any monocot or dicot plant, such those listed below under the heading "Making and Using Transgenic Plant Cells and Transgenic Plants").

In preferred embodiments of the recombinant DNA construct, each of the RNA segments consists of between 20 to 27 nucleotides. In a particularly preferred embodiment, the first and second series include RNA segments of 21 nucleotides. Each pair of small RNAs that make up a given small double-stranded RNA ("phased small RNA") can be of the same length, or can be of different lengths, such as illustrated in FIG. 8B and Table 4. In a preferred embodiment, the pair of small RNAs that make up a given small double-stranded RNA ("phased small RNA") is a pair of 21-nucleotide small RNAs. In one embodiment, the contiguous RNA segments are all of the same size. In a preferred embodiment, the RNA segments all consist of 21 nucleotides. In another embodiment, the RNA segments vary in size; preferably they are sized such that when the first series and second series of contiguous RNA segments hybridize, the individual segments are aligned in a manner permitting cleavage in phase to the intended small double-stranded RNAs. In a preferred embodiment, the first and second series of contiguous RNA segments contain an equal number of RNA segments which are arranged such that when the first series and second series of contiguous RNA segments hybridize and form an RNA duplex (hybridized RNA), a RNA segment of a given size in the first series is hybridized to a corresponding RNA segment in the second series of equivalent size.

In a preferred embodiment of the recombinant DNA construct, strands of the hybridized RNA are located on a single molecule and the construct further includes DNA that transcribes to a spacer that links the first and second series of contiguous RNA segments. The spacer generally includes DNA that does not correspond to the target gene (although in some embodiments can include sense or anti-sense sequence of the target gene). The spacer includes at least about 4 nucleotides; in various embodiments, the spacer contains at least about 4, at least about 10, at least about 20, at least about 30, at least about 40, at least about 50, at least about 60, at least about 80, at least about 100, at least about 120, or at least about 150 nucleotides. In one embodiment, the spacer is a contiguous nucleotide sequence derived from the spacer of a transcript of a naturally occurring phased small RNA locus. Non-limiting examples of spacers are provided by SEQ ID NO. 23 and SEQ ID NO. 68 as well as spacers having at least 90% sequence identity with either of SEQ ID NO. 23 and SEQ ID NO. 68.

In one embodiment, the spacer is designed to transcribed to single-stranded RNA or to at least partially double-stranded RNA (such as in a "kissing stem-loop" arrangement), or to an RNA that assumes a secondary structure or three-dimensional configuration (e.g., a large loop of antisense sequence of the target gene or an aptamer) that confers on the transcript an additional desired characteristic, such as increased stability, increased half-life in vivo, or cell or tissue specificity. In one example, the spacer is transcribed to a stabilizing loop that links the first and second series of contiguous RNA segments (see, for example, Di Giusto and King (2004) 1 *Biol. Chem.*, 279:46483-46489). In another example, the spacer transcribes to RNA including an RNA aptamer (e.g., an aptamer that binds to a cell-specific ligand) that allows cell- or tissue-specific targetting of the phased small RNAs.

In many embodiments, the recombinant DNA construct further includes DNA encoding 5' flanking sequence (e.g., SEQ ID NO. 18 and SEQ ID NO. 66) and/or 3' flanking sequence (e.g., SEQ ID NO. 27 and SEQ ID NO. 67) that are adjacent to the portion of the transcript that is the hybridized RNA. In other embodiments of the recombinant DNA construct, the strands of the hybridized RNA are located on separate molecules. Preferred embodiments of the invention include a recombinant DNA construct including at least one nucleotide sequence derived from a transcript of a naturally occurring phased small RNA locus selected from the group consisting of 5' flanking sequence, 3' flanking sequence, and spacer sequence. Non-limiting embodiments include a recombinant DNA construct including at least one nucleotide sequence selected from the group consisting of SEQ ID NO. 18, SEQ ID NO. 23, SEQ ID NO. 27, the DNA sequence encoding SEQ ID NO. 66, the DNA sequence encoding SEQ ID NO. 67, and the DNA sequence encoding SEQ ID NO. 68. Additional embodiments of the invention include a recombinant DNA construct including at least one nucleotide sequence having at least 90% sequence identity with any of SEQ ID NO. 18, SEQ ID NO. 23, SEQ ID NO. 27, the DNA sequence encoding SEQ ID NO. 66, the DNA sequence encoding SEQ ID NO. 67, and the DNA sequence encoding SEQ ID NO. 68.

Recombinant DNA constructs of this invention are designed to suppress one or more target genes as described below under the heading "Target Genes". The construct is designed so that each RNA segment of the first series hybridizes to an RNA segment of the second series; the transcript transcribed from the construct is cleaved in phase in vivo, resulting in multiple small double-stranded RNAs ("phased small RNAs") which correspond to the paired hybridized RNA segments. Preferably, each of the phased small RNAs contains at least one mismatch. A mismatch generally includes one or more non-base-paired nucleotides (on either or on both segments), forming a "bump" or "bulge" or "loop" within the otherwise base-paired double-stranded RNA. In a preferred embodiment, each phased small RNA includes one or more unpaired bases forming an overhang at one or at both ends; most preferably the overhang is a 2-nucleotide overhang such as is depicted in FIG.

1, FIG. 6, and FIG. 8B. In a preferred embodiment, at least one of the phased small RNAs is designed to suppress one or more target genes; that is, one of the two anti-parallel strands that makes up the phased small RNA is substantially complementary to a target gene.

The first and second series of contiguous RNA segments are designed so that when the first series and second series of contiguous RNA segments hybridize and form an RNA duplex (hybridized RNA), the small double-stranded RNAs resulting from cleavage in-phase of the hybridized RNA silence the target gene or genes. Most preferably, the secondary structure of the transcript is maintained so as to be substantially similar to that of a naturally occurring phased small RNA locus (e.g., as depicted in FIG. 1, FIG. 6, and FIG. 8B).

A general method for designing RNA segments corresponding to phased small RNAs for silencing a target gene, useful in making a recombinant DNA construct of this invention, includes the steps:

(a) Selecting a unique target sequence of at least 18 nucleotides specific to the target gene, e. g. by using sequence alignment tools such as BLAST (see, for example, Altschul et al. (1990) *J. Mol. Biol.,* 215:403-410; Altschul et al. (1997) *Nucleic Acids Res.,* 25:3389-3402), for example, of both maize cDNA and genomic DNA databases, to identify target transcript orthologues and any potential matches to unrelated genes, thereby avoiding unintentional silencing of non-target sequences.

(b) Analyzing the target gene for undesirable sequences (e.g., matches to sequences from non-target species, especially animals), and score each potential 19-mer segment for GC content, Reynolds score (see Reynolds et al. (2004) *Nature Biotechnol.,* 22:326-330), and functional asymmetry characterized by a negative difference in free energy ("ΔΔG") (see Khvorova et al. (2003) *Cell,* 115:209-216). Preferably 19-mers are selected that have all or most of the following characteristics: (1) a Reynolds score >4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the engineered phased siRNA precursor transcript. Preferably multiple (3 or more) 19-mers are selected for testing.

(c) Determining the reverse complement of the selected 19-mers to use in making a synthetic 21-mer phased small RNAs\; the additional nucleotide at position 20 is preferably matched to the selected target sequence, and the nucleotide at position 21 is preferably chosen to be unpaired to prevent spreading of silencing on the target transcript;

(d) Testing the synthetic phased small RNAs, for example, in an *Agrobacterium*-mediated transient *Nicotiana benthamiana* assay for siRNA expression and target repression.

and (e) Cloning the most effective phased small RNAs into a construct for stable transformation of maize (see the sections under the headings "Making and Using Recombinant DNA Constructs" and "Making and Using Transgenic Plant Cells and Transgenic Plants").

The recombinant DNA construct is made by commonly used techniques, such as those described under the heading "Making and Using Recombinant DNA Constructs" and illustrated in the working Examples. The recombinant DNA construct is particularly useful for making transgenic plant cells, transgenic plants, and transgenic seeds as discussed below under "Transgenic Plant Cells and Transgenic Plants".

A Recombinant DNA Construct Including an Exogenous Phased Small RNA Recognition Site Another aspect of this invention includes a recombinant DNA construct including a promoter operably linked to DNA that transcribes to RNA including: (a) at least one exogenous recognition site recognizable by a phased small RNA expressed in a specific cell of a multicellular eukaryote, and (b) target RNA to be suppressed in the specific cell, wherein the target RNA is to be expressed in cells of the multicellular eukaryote other than the specific cell. The exogenous recognition site includes an RNA sequence that is substantially complementary, or near perfectly complementary, or even perfectly complementary, to a phased small RNA; the exogenous recognition site hybridizes to the phased small RNA, leading to suppression or silencing of the target RNA. The phased small RNA can be transcribed from a native or endogenous phased small RNA locus, or from a synthetic phased small RNA locus that is transgenically expressed. In various embodiments of the recombinant DNA construct, the at least one exogenous recognition site is located within at least one of: (a) the 5' untranslated region of the target RNA; (b) the 3' untranslated region of the target RNA; and (c) the target RNA.

In non-limiting embodiments, the exogenous recognition site is recognized by and silenced by a phased small RNA having a nucleotide sequence selected from the group consisting of SEQ ID NOS. 1, 2, 3, 4, 5, 6, 7, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, and 65. In preferred embodiments, the exogenous recognition site is recognized by and silenced by a phased small RNA having a nucleotide sequence selected from the group consisting of SEQ ID NOS. 1, 2, 3, 4, 5, 6, 7, 35, 37, 38, 39, 40, 41, 42, 43, 45, 46, 49, 51, 52, 53, 54, 55, 56, 60, 61, 62, 63, 64, and 65. In a particularly preferred embodiment, the exogenous recognition site is recognized by and silenced by a phased small RNA having a nucleotide sequence selected from the group consisting of SEQ ID NOS. 1, 2, 3, 4, 5, 6, 7, 37, 38, 40, 41, 46, 61, 62, 63, 64, and 65.

Non-Natural Transgenic Plant Cells and Transgenic Plants

A further aspect of this invention provides a non-natural transgenic plant cell having in its genome any of the recombinant DNA constructs of this invention. Thus, the inventors claim a non-natural transgenic plant cell having in its genome a recombinant DNA construct encoding a transcript that folds into hybridized RNA that is cleaved in phase in vivo into multiple small double-stranded RNAs for gene suppression. The inventors also claim a non-natural transgenic plant cell having in its genome a recombinant DNA construct including DNA that transcribes to: (a) a first series of contiguous RNA segments, and (b) a second series of contiguous RNA segments, wherein the first series of contiguous RNA segments hybridize in vivo to the second series of RNA segments to form hybridized RNA that is cleaved in phase in vivo into multiple small double-stranded RNAs ("phased small RNAs") for gene suppression. The inventors further claim a non-natural transgenic plant cell having in its genome a recombinant DNA construct including a promoter operably linked to DNA that transcribes to RNA including: (a) at least one exogenous recognition site recognizable by a phased small RNA expressed in a specific cell of a multicellular eukaryote, and (b) target RNA to be suppressed in the specific cell, wherein the target RNA is to be expressed in cells of the multicellular eukaryote other than the specific cell.

Also provided are a non-natural transgenic plant containing the non-natural transgenic plant cell of this invention, a non-natural transgenic plant grown from the non-natural transgenic plant cell of this invention, and non-natural transgenic seed produced by the non-natural transgenic plants. The non-natural transgenic plant of this invention includes plants of any developmental stage, and includes a non-natural transgenic regenerated plant prepared from the non-natural transgenic plant cells disclosed herein, or a non-natural transgenic progeny plant (which can be an inbred or hybrid progeny plant) of the regenerated plant, or non-natural transgenic seed of such a non-natural transgenic plant. Also provided and claimed is a non-natural transgenic seed having in its genome a recombinant DNA construct of this invention. The non-natural transgenic plant cells, non-natural transgenic plants, and non-natural transgenic seeds of this invention are made by methods well-known in the art, as described below under the heading "Making and Using Transgenic Plant Cells and Transgenic Plants".

The non-natural transgenic plant cell can include an isolated plant cell (e.g., individual plant cells or cells grown in or on an artificial culture medium), or can include a plant cell in undifferentiated tissue (e.g., callus or any aggregation of plant cells). The non-natural transgenic plant cell can include a plant cell in at least one differentiated tissue selected from the group consisting of leaf (e.g., petiole and blade), root, stem (e.g., tuber, rhizome, stolon, bulb, and corm) stalk (e.g., xylem, phloem), wood, seed, fruit (e.g., nut, grain, fleshy fruits), and flower (e.g., stamen, filament, anther, pollen, carpel, pistil, ovary, ovules).

The non-natural transgenic plant cell or non-natural transgenic plant of the invention can be any suitable plant cell or plant of interest. Both transiently transformed and stably transformed plant cells are encompassed by this invention. Stably transformed transgenic plants are particularly preferred. In many preferred embodiments, the non-natural transgenic plant is a fertile transgenic plant from which seed can be harvested, and the invention further claims non-natural transgenic seed of such transgenic plants, wherein the seed preferably also contains the recombinant construct of this invention.

In some embodiments of this invention, the non-natural plant is a non-natural transgenic plant, and all cells (with the possible exception of haploid cells) and tissues of the plant contain the recombinant DNA construct of this invention. In other embodiments, the non-natural plant is not completely transgenic, but includes both non-natural transgenic cells or tissues and non-transgenic cells or tissues (for example, transgenic tissue grafted onto non-transgenic tissue). In a non-limiting embodiment, the plant includes a non-transgenic scion and a transgenic rootstock including the transgenic plant cell, wherein the non-transgenic scion and transgenic rootstock are grafted together. Such embodiments are particularly useful where the plant is one that is commonly vegetatively grown as a scion grafted onto a rootstock (wherein scion and rootstock can be of the same species or variety or of different species or variety); non-limiting examples include grapes (e.g., wine grapes and table grapes), apples, pears, quince, avocados, citrus, stone fruits (e. g., peaches, plums, nectarines, apricots, cherries), kiwifruit, roses, and other plants of agricultural or ornamental importance.

Also encompassed by this invention are non-natural plants that are not transgenic in the sense of having had recombinant DNA introduced into their genome, but are non-natural plants having a genome that has been artificially modified by means other than recombinant DNA technology. Such artificial modifications of the native genomic sequence include insertions, deletions, substitutions, frame shifts, transpositions, duplications, and inversions. Artificial modification of a native genomic sequence is achieved by any means, including mutagenesis by chemicals (such as methane sulfonate, methyl methane sulfonate, diethylsulfate), nitrosoguanidine, and other alkylating agents, base analogues such as 5-bromo-deoxyuridine, interchelating agents such as ethidium bromide, crosslinking agents such as platinum, and oxidating agents such as nitrous acid or reactive oxygen species) or mutagenesis by physical treatments (such as exposure to ultraviolet light, radioactive isotopes, or ionizing radiation). Such mutagenesis can be random or non-random (e.g., site-directed mutagenesis). Mutagenesis can be carried out with intact plants, plant tissues, or plant cells. One non-limiting example of mutagenesis is treatment of maize pollen with an alkylating agent. Mutagenesis is generally carried out on a population, following screening of that population to allow selection of individuals having the desired property. These non-natural plants are useful in ways similar to those described below for transgenic plants; for example, they can be grown for production of seed or other harvestable parts, or used to grow progeny generations (including hybrid generations).

Target Genes

Phased small RNAs of this invention and the recombinant DNA constructs encoding such can be designed to suppress any target gene or genes. The target gene can be translatable (coding) sequence, or can be non-coding sequence (such as non-coding regulatory sequence), or both, and can include at least one gene selected from the group consisting of a eukaryotic target gene, a non-eukaryotic target gene, a microRNA precursor DNA sequence, and a microRNA promoter. The target gene can be native or endogenous to the cell (e.g., a cell of a plant or animal) in which the recombinant DNA construct is transcribed, or can be native to a pest or pathogen of the plant or animal in which the recombinant DNA construct is transcribed. The target gene can be an exogenous gene, such as a transgene in a plant. A target gene can be a native gene targetted for suppression, with or without concurrent expression of an exogenous transgene, for example, by including a gene expression element in the recombinant DNA construct from which the phased small RNAs are transcribed, or in a separate recombinant DNA construct. For example, it can be desirable to replace a native gene with an exogenous transgene homologue.

The target gene can include a single gene or part of a single gene that is targetted for suppression, or can include, for example, multiple consecutive segments of a target gene, multiple non-consecutive segments of a target gene, multiple alleles of a target gene, or multiple target genes from one or more species. A target gene can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans.

In one embodiment, the target gene is exogenous to the plant in which the recombinant DNA construct is to be transcribed, but endogenous to a pest or pathogen (e.g., viruses, bacteria, fungi, oomycetes, and invertebrates such as insects, nematodes, and molluscs) of the plant. The target gene can include multiple target genes, or multiple segments of one or more genes. In one preferred embodiment, the target gene or genes is a gene or genes of an invertebrate pest or pathogen of the plant. These embodiments are particularly useful in providing transgenic plants having resistance to one or more plant pests or pathogens, for example, resistance to a nematode such as soybean cyst nematode or root knot nematode, or to a pest insect, or to at least one pathogenic virus, bacterium, or fungus.

The target gene can be translatable (coding) sequence, or can be non-coding sequence (such as non-coding regulatory sequence), or both. Non-limiting examples of a target gene include non-translatable (non-coding) sequence, such as, but not limited to, 5' untranslated regions, promoters, enhancers, or other non-coding transcriptional regions, 3' untranslated regions, terminators, and introns. Target genes include genes encoding microRNAs, small interfering RNAs, RNA components of ribosomes or ribozymes, small nucleolar RNAs, and other non-coding RNAs (see, for example, non-coding RNA sequences provided publicly at rfam.wustl.edu; Erdmann et al. (2001) *Nucleic Acids Res.,* 29:189-193; Gottesman (2005) *Trends Genet.,* 21:399-404; Griffiths-Jones et al. (2005) *Nucleic Acids Res.,* 33:121-124). One specific example of a target gene includes a microRNA recognition site (that is, the site on an RNA strand to which a mature miRNA binds and induces cleavage). Another specific example of a target gene includes a microRNA precursor sequence native to a pest or pathogen of the transgenic plant, that is, the primary transcript encoding a microRNA, or the RNA intermediates processed from this primary transcript (e.g., a nuclear-limited pri-miRNA or a pre-miRNA which can be exported from the nucleus into the cytoplasm). See, for example, Lee et al. (2002) *EMBO Journal,* 21:4663-4670; Reinhart et al. (2002) *Genes & Dev.,* 16:161611626; Lund et al. (2004) *Science,* 303:95-98; and Millar and Waterhouse (2005) *Funct. Integr Genomics,* 5:129-135. Target genes can also include translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin).

In many preferred embodiments, the target gene is an essential gene of a plant pest or pathogen. Essential genes include genes that are required for development of the pest or pathogen to a fertile reproductive adult. Essential genes include genes that, when silenced or suppressed, result in the death of the organism (as an adult or at any developmental stage, including gametes) or in the organism's inability to successfully reproduce (e.g., sterility in a male or female parent or lethality to the zygote, embryo, or larva). A description of nematode essential genes is found, e.g., in Kemphues, K. "Essential Genes" (Dec. 24, 2005), WormBook, ed. The *C. elegans* Research Community, WormBook, doi/10.1895/wormbook.1.57.1, available on line at wormbook.org. Non-limiting examples of nematode essential genes include major sperm protein, RNA polymerase II, and chitin synthase (see, e.g., U.S. Patent Application Publication US20040098761 A1); additional soybean cyst nematode essential genes are provided in U.S. patent application Ser. No. 11/360,355 (now U.S. Pat. No. 8,088,976, issued Jan. 3, 2012), filed 23 Feb. 2006, incorporated by reference herein. A description of insect genes is publicly available at the *Drosophila* genome database (available on line at flybase.bio.indiana.edu/). The majority of predicted *Drosophila* genes have been analyzed for function by a cell culture-based RNA interference screen, resulting in 438 essential genes being identified; see Boutros et al. (2004) *Science,* 303:832-835, and supporting material available on line at sciencemag.org/cgi/content/full/303/5659/832/DC1. A description of bacterial and fungal essential genes is provided in the Database of Essential Genes ("DEG", available on line at tubic.tju.edu.cn/deg/); see Zhang et al. (2004) *Nucleic Acids Res.,* 32:D271-D272.

Plant pest invertebrates include, but are not limited to, pest nematodes, pest molluscs (slugs and snails), and pest insects. Plant pathogens of interest include fungi, oomycetes, bacteria (e.g., the bacteria that cause leaf spotting, fireblight, crown gall, and bacterial wilt), mollicutes, and viruses (e.g., the viruses that cause mosaics, vein banding, flecking, spotting, or abnormal growth). See also G. N. Agrios, "Plant Pathology" (Fourth Edition), Academic Press, San Diego, 1997, 635 pp., for descriptions of fungi, bacteria, mollicutes (including mycoplasmas and spiroplasmas), viruses, nematodes, parasitic higher plants, and flagellate protozoans, all of which are plant pests or pathogens of interest. See also the continually updated compilation of plant pests and pathogens and the diseases caused by such on the American Phytopathological Society's "Common Names of Plant Diseases", compiled by the Committee on Standardization of Common Names for Plant Diseases of The American Phytopathological Society, 1978-2005, available online at apsnet.org/online/common/top.asp.

Non-limiting examples of fungal plant pathogens of particular interest include, e. g., the fungi that cause powdery mildew, rust, leaf spot and blight, damping-off, root rot, crown rot, cotton boll rot, stem canker, twig canker, vascular wilt, smut, or mold, including, but not limited to, *Fusarium* spp., *Phakospora* spp., *Rhizoctonia* spp., *Aspergillus* spp., *Gibberella* spp., *Pyricularia* spp., and *Alternaria* spp. Specific examples of fungal plant pathogens include *Phakospora pachirhizi* (Asian soy rust), *Puccinia sorghi* (corn common rust), *Puccinia polysora* (corn Southern rust), *Fusarium oxysporum* and other *Fusarium* spp., *Alternaria* spp., *Penicillium* spp., *Rhizoctonia solani, Exserohilum turcicum* (Northern corn leaf blight), *Bipolaris maydis* (Southern corn leaf blight), *Ustilago maydis* (corn smut), *Fusarium graminearum* (*Gibberella zeae*), *Fusarium verticilliodes* (*Gibberella moniliformis*), *F. proliferatum* (*G. fujikuroi* var. *intermedia*), *F. subglutinans* (*G. subglutinans*), *Diplodia maydis, Sporisorium holci-sorghi, Colletotrichum graminicola, Setosphaeria turcica, Aureobasidium zeae, Sclerotinia sclerotiorum,* and the numerous fungal species provided in Tables 4 and 5 of U.S. Pat. No. 6,194,636, which is incorporated in its entirety by reference herein. Non-limiting examples of plant pathogens include pathogens previously classified as fungi but more recently classified as oomycetes. Specific examples of oomycete plant pathogens of particular interest include members of the genus *Pythium* (e.g., *Pythium aphanidermatum*) and *Phytophthora* (e.g., *Phytophthora infestans, Phytophthora sojae*) and organisms that cause downy mildew (e.g., *Peronospora farinosa*).

Non-limiting examples of bacterial pathogens include the mycoplasmas that cause yellows disease and spiroplasmas such as *Spiroplasma kunkelii*, which causes corn stunt, eubacteria such as *Pseudomonas avenae, Pseudomonas andropogonis*, Envinia *stewartii, Pseudomonas syringae* pv. *syringae, Xylella fastidiosa*, and the numerous bacterial species listed in Table 3 of U.S. Pat. No. 6,194,636, which is incorporated in its entirety by reference herein.

Non-limiting examples of viral plant pathogens of particular interest include maize dwarf mosaic virus (MDMV), sugarcane mosaic virus (SCMV, formerly MDMV strain B), wheat streak mosaic virus (WSMV), maize chlorotic dwarf virus (MCDV), barley yellow dwarf virus (BYDV), banana bunchy top virus (BBTV), and the numerous viruses listed in Example 7 below and in Table 2 of U.S. Pat. No. 6,194,636, which is incorporated in its entirety by reference herein.

Non-limiting examples of invertebrate pests include cyst nematodes *Heterodera* spp. especially soybean cyst nematode *Heterodera glycines*, root knot nematodes *Meloidogyne* spp., lance nematodes *Hoplolaimus* spp., stunt nematodes *Tylenchorhynchus* spp., spiral nematodes *Helicotylenchus* spp., lesion nematodes *Pratylenchus* spp., ring nematodes *Criconema* spp., foliar nematodes *Aphelenchus* spp. or *Aphelenchoides* spp., corn rootworms, *Lygus* spp., aphids and similar sap-sucking insects such as *phylloxera* (*Daktulosphaira vitifoliae*), corn borers, cutworms, armyworms, leafhoppers, Japanese beetles, grasshoppers, and other pest coleopterans, dipterans, and lepidopterans. Specific examples of invertebrate pests include pests capable of infesting the root systems of crop plants, e.g., northern corn rootworm (*Diabrotica barberi*), southern corn rootworm (*Diabrotica undecimpunctata*), Western corn rootworm (*Diabrotica virgifera*), corn root aphid (*Anuraphis maidiradicis*), black cutworm (*Agrotis ipsilon*), glassy cutworm (*Crymodes devastator*), dingy cutworm (*Feltia ducens*), claybacked cutworm (*Agrotis gladiaria*), wireworm (*Melanotus* spp., *Aeolus mellillus*), wheat wireworm (*Aeolus mancus*), sand wireworm (*Horistonotus uhlerii*), maize billbug (*Sphenophorus maidis*), timothy billbug (*Sphenophorus zeae*), bluegrass billbug (*Sphenophorus parvulus*), southern corn billbug (*Sphenophorus callosus*), white grubs (*Phyllophaga* spp.), seedcorn maggot (*Delia platura*), grape colaspis (*Colaspis brunnea*), seedcorn beetle (*Stenolophus lecontei*), and slender seedcorn beetle (*Clivinia impressifrons*), as well as the parasitic nematodes listed in Table 6 of U.S. Pat. No. 6,194,636, which is incorporated in its entirety by reference herein.

Invertebrate pests of particular interest, especially in but not limited to southern hemisphere regions (including South and Central America) include aphids, corn rootworms, *spodoptera*, noctuideae, potato beetle, *Lygus* spp., any hemipteran, homopteran, or heteropteran, any lepidopteran, any coleopteran, nematodes, cutworms, earworms, armyworms, borers, leaf rollers, and others. Arthropod pests specifically encompassed by this invention include various cutworm species including cutworm (*Agrotis repleta*), black cutworm (*Agrotis ipsilon*), cutworm (*Anicla ignicans*), granulate cutworm (*Feltia subterranea*), "gusano áspero" (*Agrotis malefida*); Mediterranean flour moth (*Anagasta kuehniella*), square-necked grain beetle (*Cathartus quadricollis*), flea beetle (*Chaetocnema* spp), rice moth (*Corcyra cephalonica*), corn rootworm or "vaquita de San Antonio" (*Diabotica speciosa*), sugarcane borer (*Diatraea saccharalis*), lesser cornstalk borer (*Elasmopalpus lignosellus*), brown stink bug (*Euschistus* spp.), corn earworm (*Helicoverpa zea*), flat grain beetle (*Laemophloeus minutus*), grass looper moth (*Mods latipes*), sawtoothed grain beetle (*Oryzaephilus surinamensis*), meal moth (*Pyralis farinalis*), Indian meal moth (*Plodia interpunctella*), corn leaf aphid (*Rhopalosiphum maidis*), brown burrowing bug or "chinche subterránea" (*Scaptocoris castanea*), greenbug (*Schizaphis graminum*), grain weevil (*Sitophilus zeamais*), Angoumois grain moth (*Sitotroga cerealella*), fall armyworm (*Spodoptera frugiperda*), cadelle beetle (*Tenebroides mauritanicus*), two-spotted spider mite (*Tetranychus urticae*), red flour beetle (*Triboleum castaneum*), cotton leafworm (*Alabama argillacea*), boll weevil (*Anthonomus grandis*), cotton aphid (*Aphis gossypii*), sweet potato whitefly (*Bemisia tabaci*), various *thrips* species (*Frankliniella* spp.), cotton earworm (*Helicoverpa zea*), "oruga bolillera" (e.g., *Helicoverpa geletopoeon*), tobacco budworm (*Heliothis virescens*), stinkbug (*Nezara viridula*), pink bollworm (*Pectinophora gossypiella*), beet armyworm (*Spodoptera exigua*), spider mites (*Tetranychus* spp.), onion *thrips* (*Thrips tabaci*), greenhouse whitefly (*Trialeurodes vaporarium*), velvetbean caterpillar (*Anticarsia gemmatalis*), spotted maize beetle or "astilo moteado" (*Astylus atromaculatus*), "oruga de la alfalfa" (*Colias lesbia*), "chinche marron" or "chinche de los cuernos" (*Dichelops furcatus*), "alquiche chico" (*Edessa miditabunda*), blister beetles (*Epicauta* spp.), "barrenador del brote" (*Epinotia aporema*), "oruga verde del yuyo colorado" (*Loxostege bifidalis*), rootknot nematodes (*Meloidogyne* spp.), "oruga cuarteadora" (*Mods repanda*), southern green stink bug (*Nezara viridula*), "chinche de la alfalfa" (*Piezodorus guildinii*), green cloverworm (*Plathypena scabra*), soybean looper (*Pseudoplusia includens*), looper moth "isoca medidora del girasol" (*Rachiplusia nu*), yellow woolybear (*Spilosoma virginica*), yellowstriped armyworm (*Spodoptera ornithogalli*), various root weevils (family Curculionidae), various wireworms (family Elateridae), and various white grubs (family Scarabaeidae). Nematode pests specifically encompassed by this invention include nematode pests of maize (*Belonolaimus* spp., *Trichodorus* spp., *Longidorus* spp., *Dolichodorus* spp., *Anguina* spp., *Pratylenchus* spp., *Meloidogyne* spp., *Heterodera* spp.), soybean (*Heterodera glycines, Meloidogyne* spp., *Belonolaimus* spp.), bananas (*Radopholus similis, Meloidogyne* spp., *Helicotylenchus* spp.), sugarcane (*Heterodera sacchari, Pratylenchus* spp., *Meloidogyne* spp.), oranges (*Tylenchulus* spp., *Radopholus* spp., *Belonolaimus* spp., *Pratylenchus* spp., *Xlphinema* spp.), coffee (*Meloidogyne* spp., *Pratylenchus* spp.), coconut palm (*Bursaphelenchus* spp.), tomatoes (*Meloidogyne* spp., *Belonolaimus* spp., *Nacobbus* spp.), grapes (*Meloidogyne* spp., *Xiphinema* spp., *Tylenchulus* spp., *Criconemella* spp.), lemon and lime (*Tylenchulus* spp., *Radopholus* spp., *Belonolaimus* spp., *Pratylenchus* spp., *Xlphinema* spp.), cacao (*Meloidogyne* spp., *Rotylenchulus reniformis*), pineapple (*Meloidogyne* spp., *Pratylenchus* spp., *Rotylenchulus reniformis*), *papaya* (*Meloidogyne* spp., *Rotylenchulus reniformis*), grapefruit (*Tylenchulus* spp., *Radopholus* spp. *Belonolaimus* spp., *Pratylenchus* spp., *Xlphinema* spp., and broad beans (*Meloidogyne* spp.).

Target genes from pests can include invertebrate genes for major sperm protein, alpha tubulin, beta tubulin, vacuolar ATPase, glyceraldehyde-3-phosphate dehydrogenase, RNA polymerase II, chitin synthase, cytochromes, miRNAs, miRNA precursor molecules, miRNA promoters, as well as other genes such as those disclosed in U.S. Patent Application Publication 2006/0021087 A1, PCT Patent Application PCT/US05/11816, and in Table II of U.S. Patent Application Publication 2004/0098761 A1, which are incorporated by reference herein. Target genes from pathogens can include genes for viral translation initiation factors, viral replicases, miRNAs, miRNA precursor molecules, fungal tubulin, fungal vacuolar ATPase, fungal chitin synthase, fungal MAP kinases, fungal Pac1 Tyr/Thr phosphatase, enzymes involved in nutrient transport (e.g., amino acid transporters or sugar transporters), enzymes involved in fungal cell wall biosynthesis, cutinases, melanin biosynthetic enzymes, polygalacturonases, pectinases, pectin lyases, cellulases, proteases, genes that interact with plant avirulence genes, and other genes involved in invasion and replication of the pathogen in the infected plant. Thus, a target gene need not be endogenous to the plant in which the recombinant DNA construct is transcribed. A recombinant DNA construct encoding phased small RNAs of the invention can be transcribed in a plant and used to suppress a gene of a pathogen or pest that may infest the plant.

Specific, non-limiting examples of suitable target genes also include amino acid catabolic genes (such as, but not limited to, the maize LKR/SDH gene encoding lysine-ketoglutarate reductase (LKR) and saccharopine dehydrogenase (SDH), and its homologues), maize zein genes, genes involved in fatty acid synthesis (e.g., plant microsomal fatty acid desaturases and plant acyl-ACP thioesterases, such as, but not limited to, those disclosed in U.S. Pat. Nos. 6,426,448, 6,372,965, and 6,872,872), genes involved in multi-step biosynthesis pathways, where it may be of interest to regulate the level of one or more intermediates, such as genes encoding enzymes for polyhydroxyalkanoate biosynthesis (see, for example, U.S. Pat. No. 5,750,848); and genes encoding cell-cycle control proteins, such as proteins with cyclin-dependent kinase (CDK) inhibitor-like activity (see, for example, genes disclosed in International Patent Application Publication Number WO 05007829A2). Target genes can include genes encoding undesirable proteins (e.g., allergens or toxins) or the enzymes for the biosynthesis of undesirable compounds (e.g., undesirable flavor or odor components). Thus, one embodiment of the invention is a transgenic plant or tissue of such a plant that is improved by the suppression of allergenic proteins or toxins, e.g., a peanut, soybean, or wheat kernel with decreased allergenicity. Target genes can include genes involved in fruit ripening, such as polygalacturonase. Target genes can include genes where expression is preferably limited to a particular cell or tissue or developmental stage, or where expression is preferably transient, that is to say, where constitutive or general suppression, or suppression that spreads through many tissues, is not necessarily desired. Thus, other examples of suitable target genes include genes encoding proteins that, when expressed in transgenic plants, make the transgenic plants resistant to pests or pathogens (see, for example, genes for cholesterol oxidase as disclosed in U.S. Pat. No. 5,763,245); genes where expression is pest- or pathogen-induced; and genes which can induce or restore fertility (see, for example, the barstar/barnase genes described in U.S. Pat. No. 6,759,575); all the publications and patents cited in this paragraph are incorporated by reference in their entirety herein.

The phased small RNAs can be designed to be more specifically suppress the target gene, by designing the phased small RNAs to include regions substantially non-identical to a non-target gene sequence. Non-target genes can include any gene not intended to be silenced or suppressed, either in a plant containing the recombinant DNA construct encoding the phased small RNAs or in organisms that may come into contact with the phased small RNAs. A non-target gene sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans).

In one embodiment, the target gene is a gene endogenous to a given species, such as a given plant (such as, but not limited to, agriculturally or commercially important plants, including monocots and dicots), and the non-target gene can be, e.g., a gene of a non-target species, such as another plant species or a gene of a virus, fungus, bacterium, invertebrate, or vertebrate, even a human. One non-limiting example is where the phased small RNAs are designed to suppress a target gene that is a gene endogenous to a single species (e.g., Western corn rootworm, *Diabrotica virgifera virgifera* LeConte) but to not suppress a non-target gene such as genes from related, even closely related, species (e.g., Northern corn rootworm, *Diabrotica barberi* Smith and Lawrence, or Southern corn rootworm, *Diabrotica undecimpunctata*).

In other embodiments (e.g., where it is desirable to suppress a target gene across multiple species), it may be desirable to design the phased small RNAs to suppress a target gene sequence common to the multiple species in which the target gene is to be silenced. Thus, a recombinant DNA construct encoding phased small RNAs can be designed to be specific for one taxon (for example, specific to a genus, family, or even a larger taxon such as a phylum, e.g., viruses or arthropoda) but not for other taxa (e.g., plants or vertebrates or mammals). In one non-limiting example of this embodiment, a recombinant DNA construct encoding phased small RNAs can be selected so as to target pathogenic fungi (e.g., a *Fusarium* spp.) but not target any gene sequence from beneficial fungi.

In another non-limiting example of this embodiment, phased small RNAs for gene silencing in corn rootworm can be selected to be specific to all members of the genus *Diabrotica*. In a further example of this embodiment, such *Diabrotica*-targetted phased small RNAs can be selected so as to not target any gene sequence from beneficial coleopterans (for example, predatory coccinellid beetles, commonly known as ladybugs or ladybirds) or other beneficial insect species.

The required degree of specificity of an RNA for silencing a target gene depends on various factors. Factors can include the size of the phased small RNAs that are expected to be produced by the action of a ribonuclease (preferably DCL4 or a DCL4 orthologue) on the hybridized RNA, and the relative importance of decreasing the phased small RNAs' potential to suppress non-target genes. In a non-limiting example, where the phased small RNAs are expected to be 21 base pairs in size, one particularly preferred embodiment includes RNA for silencing a target gene that encodes regions substantially non-identical to a non-target gene sequence, such as regions within which every contiguous fragment including at least 21 nucleotides matches fewer than 21 (e.g., fewer than 21, or fewer than 20, or fewer than 19, or fewer than 18, or fewer than 17) out of 21 contiguous nucleotides of a non-target gene sequence. In another embodiment, regions substantially non-identical to a non-target gene sequence include regions within which every contiguous fragment including at least 19 nucleotides matches fewer than 19 (e.g., fewer than 19, or fewer than 18, or fewer than 17, or fewer than 16) out of 19 contiguous nucleotides of a non-target gene sequence.

In some embodiments, it may be desirable to design phased small RNAs for silencing a target gene to include regions predicted to not generate undesirable polypeptides, for example, by screening the recombinant DNA construct encoding the phased small RNAs or each component phased small RNA for sequences that may encode known undesirable polypeptides or close homologues of these. Undesirable polypeptides include, but are not limited to, polypeptides homologous to known allergenic polypeptides and polypeptides homologous to known polypeptide toxins. Publicly available sequences encoding such undesirable potentially allergenic peptides are available, for example, the Food Allergy Research and Resource Program (FARRP) allergen database (available at allergenonline.com) or the Biotechnology Information for Food Safety Databases (available at iit.edu/~sgendel/fa.htm) (see also, for example, Gendel (1998) *Adv. Food Nutr. Res.,* 42:63-92). Undesirable sequences can also include, for example, those polypeptide sequences annotated as known toxins or as potential or known allergens and contained in publicly available databases such as GenBank, EMBL, SwissProt, and others, which are searchable by the Entrez system (ncbi.nih.gov/Entrez). Non-limiting examples of undesirable, potentially allergenic peptide sequences include glycinin from soybean, oleosin and agglutinin from peanut, glutenins from wheat, casein, lactalbumin, and lactoglobulin from bovine milk, and tropomyosin from various shellfish (allergenonline.com). Non-limiting examples of undesirable, potentially toxic peptides include tetanus toxin tetA from *Clostridium tetani*, diarrheal toxins from *Staphylococcus aureus*, and venoms such as conotoxins from *Conus* spp. and neurotoxins from arthropods and reptiles (ncbi.nih.gov/Entrez).

In one non-limiting example, the recombinant DNA construct encoding the phased small RNAs or each component phased small RNA is screened to eliminate those transcribable sequences encoding polypeptides with perfect homology to a known allergen or toxin over 8 contiguous amino acids, or with at least 35% identity over at least 80 amino acids; such screens can be performed on any and all possible reading frames in both directions, on potential open reading frames that begin with AUG (ATG in the corresponding DNA), or on all possible reading frames, regardless of whether they start with an AUG (or ATG) or not. When a "hit" or match is made, that is, when a sequence that encodes a potential polypeptide with perfect homology to a known allergen or toxin over 8 contiguous amino acids (or at least about 35% identity over at least about 80 amino acids), is identified, the nucleic acid sequences corresponding to the hit can be avoided, eliminated, or modified when selecting sequences to be used in an RNA for silencing a target gene. In one embodiment the recombinant DNA construct encoding the phased small RNAs or each component phased small RNA is designed so no potential open reading frames that begin with AUG (ATG in the corresponding DNA) is included.

Avoiding, elimination of, or modification of, an undesired sequence can be achieved by any of a number of methods known to those skilled in the art. In some cases, the result can be novel sequences that are believed to not exist naturally. For example, avoiding certain sequences can be accomplished by joining together "clean" sequences into novel chimeric sequences to be used in the recombinant DNA construct encoding the phased small RNAs.

Figure 4:
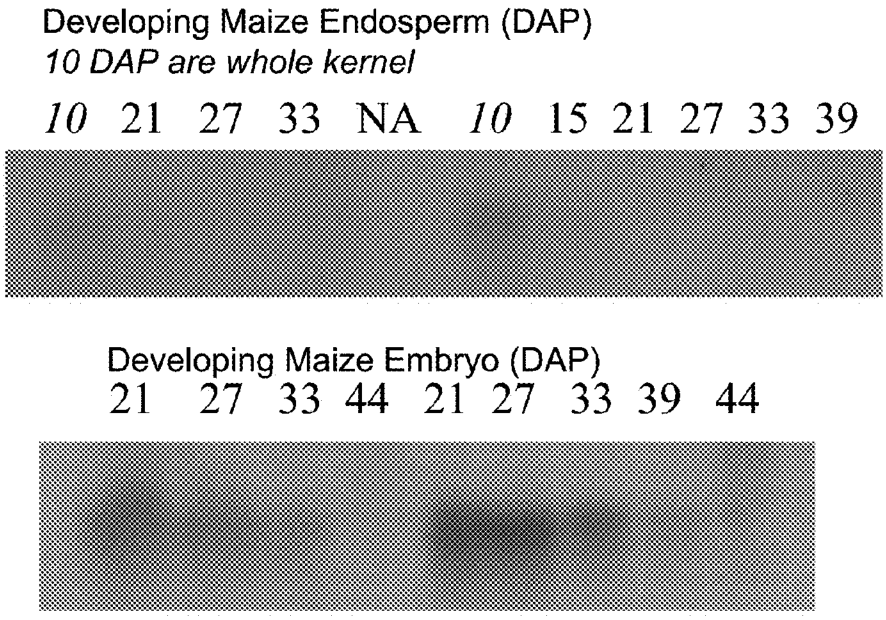
FIG. 4 depicts the results of northern blot analysis of tissue from developing maize kernels using a single oligonucleotide probe with sequence complementary to an endogenous phased small RNA, as described in Example 2.

Applicants recognize that in some dsRNA-mediated gene silencing, it is possible for imperfectly matching dsRNA sequences to be effective at gene silencing. For example, it has been shown that mismatches near the center of a miRNA complementary site has stronger effects on the miRNA's gene silencing than do more distally located mismatches. See, for example, FIG. 4 in Mallory et al. (2004) *EMBO* 1, 23:3356-3364. In another example, it has been reported that, both the position of a mismatched base pair and the identity of the nucleotides forming the mismatch influence the ability of a given siRNA to silence a target gene, and that adenine-cytosine mismatches, in addition to the G:U wobble base pair, were well tolerated (see Du et al. (2005) *Nucleic Acids Res.,* 33:1671-1677). Thus, each phased small RNA need not always have 100% sequence complementarity with the intended target gene, but generally would preferably have substantial complementarity with the intended target gene, such as about 95%, about 90%, about 85%, or about 80% complementarity with the intended target gene. One strand of the hybridized RNA (or each component phased small RNA or RNA segment) is preferably designed to have substantial complementarity to the intended target (e.g., a target messenger RNA or target non-coding RNA), such as about 95%, about 90%, about 85%, or about 80% complementarity to the intended target. In a non-limiting example, in the case of a component phased small RNA consisting of two 21-nucleotide strands, one of the two 21-nucleotide strands is substantially but not perfectly complementary to 21 contiguous nucleotides of a target RNA; preferably the nucleotide at position 21 is unpaired with the corresponding position in the target RNA to prevent transitivity.

One skilled in the art would be capable of judging the importance given to screening for regions predicted to be more highly specific to the target gene or predicted to not generate undesirable polypeptides, relative to the importance given to other criteria, such as, but not limited to, the percent sequence identity with the intended target gene or the predicted gene silencing efficiency of a given sequence. For example, it may be desirable for the phased small RNAs to be active across several species, and therefore one skilled in the art can determine that it is more important to include in the recombinant DNA construct encoding the phased small RNAs regions specific to the several species of interest, but less important to screen for regions predicted to have higher gene silencing efficiency or for regions predicted to generate undesirable polypeptides.

Combinations of Phased Small RNAs with Pesticidal Compositions

Phased small RNAs of this invention and the recombinant DNA constructs encoding such phased small RNAs are useful in controlling pests and pathogens of plants, and thus this invention further claims methods of controlling pests and pathogens of plant wherein a phased small RNA of this invention is provided to at least one cell of the plant to be protected from the pest or pathogen. The phased small RNA is generally provided by in vivo transcription of a recombinant DNA construct of this invention in a cell of the plant.

Methods of controlling pests and pathogens of plant with a phased small RNA of this invention can be used in combination with other methods or compositions for controlling pests and pathogens of plants. Thus, this invention also provides combinations of methods and combinations of compositions for controlling pests and pathogens of plants. In a preferred embodiment, the methods to be combined operate by different mechanisms to provide protection to the plant from the pest or pathogen. For example, invertebrate pests can be controlled by providing an alternative gene suppression element (such as an engineered microRNA or an engineered siRNA produced by a conventional double-stranded RNA transcript transgenically expressed in the plant) designed to silence a gene of the invertebrate pest; see, for example, the various recombinant DNA constructs and methods for gene suppression disclosed in U.S. Patent Application Publication 2006/0200878, which are incorporated herein by reference.

One non-limiting example is a method for controlling insect pests of plants, including providing at least one phased small RNA designed to silence an insect pest gene and an insecticidal agent (e.g., a *Bacillus thuringiensis* or "Bt" insecticidal protein) to which the insect pest is susceptible. When Bt proteins are provided in the diet of insect pests (e.g., via topical application to the plant or by transgenic expression in the plant) a mode of action for controlling the insect pest is exhibited that is dramatically different from the mode of action of the methods and compositions using phased small RNAs. In preferred embodiments, the combination results in synergies that were not known previously in the art for controlling insect infestation. Transgenic plants that produce one or more phased small RNA molecules that inhibit some essential biological function in a target pest along with one or more Bt insecticidal proteins that are toxic to the target pest provide surprising synergies. One synergy is the reduction in the level of expression required for either the phased small RNA(s) or the Bt insecticidal protein(s). When combined together, a lower effective dose of each pest control agent is required.

Another non-limiting example is a method for controlling viral pests of plants, including providing at least one phased small RNA designed to silence an viral pathogen gene and a composition to induce viral coat protein-mediated resistance to the plant (e.g., by transgenic expression of the viral coat protein in a plant cell). In preferred embodiments, the combination results in a synergy between the two protective components, so that a lower effective dose of each pathogen control agent is achieved.

Making and Using Recombinant DNA Constructs

The recombinant DNA constructs of this invention are made by any method suitable to the intended application, taking into account, for example, the type of expression desired and convenience of use in the plant in which the construct is to be transcribed. General methods for making and using DNA constructs and vectors are well known in the art and described in detail in, for example, handbooks and laboratory manuals including Sambrook and Russell, "Molecular Cloning: A Laboratory Manual" (third edition), Cold Spring Harbor Laboratory Press, N Y, 2001. An example of useful technology for building DNA constructs and vectors for transformation is disclosed in U.S. Patent Application Publication 2004/0115642 A1, incorporated herein by reference. DNA constructs can also be built using the GATEWAY™ cloning technology (available from Invitrogen Life Technologies, Carlsbad, Calif.), which uses the site-specific recombinase LR cloning reaction of the Integrase/att system from bacteriophage lambda vector construction, instead of restriction endonucleases and ligases. The LR cloning reaction is disclosed in U.S. Pat. Nos. 5,888,732 and 6,277,608, and in U.S. Patent Application Publications 2001/283529, 2001/282319 and 2002/0007051, all of which are incorporated herein by reference. The GATEWAY™ Cloning Technology Instruction Manual, which is also supplied by Invitrogen, provides concise directions for routine cloning of any desired DNA into a vector comprising operable plant expression elements. Another alternative vector fabrication method employs ligation-independent cloning as disclosed by Aslandis et al. (1990) *Nucleic Acids Res.,* 18:6069-6074 and Rashtchian et al. (1992) *Biochem.,* 206:91-97, where a DNA fragment with single-stranded 5' and 3' ends is annealed to complementary 5' and 3' single-stranded ends of at least one other DNA fragment to produce a desired vector which can then be ligated and amplified in vivo.

In certain embodiments, the DNA sequence of the recombinant DNA construct includes sequence that has been codon-optimized for the plant in which the recombinant DNA construct is to be expressed. For example, a recombinant DNA construct to be expressed in a plant can have all or parts of its sequence (e.g., the first gene suppression element or the gene expression element) codon-optimized for expression in a plant by methods known in the art. See, e.g., U.S. Pat. No. 5,500,365, incorporated by reference, for a description of codon-optimization for plants; see also De Amicis and Marchetti (2000) *Nucleic Acid Res.,* 28:3339-3346.

Making and Using Transgenic Plant Cells and Transgenic Plants

Where a recombinant DNA construct of this invention is used to produce a non-natural transgenic plant cell, non-natural transgenic plant, or non-natural transgenic seed of this invention, transformation can include any of the well-known and demonstrated methods and compositions. Suitable methods for plant transformation include virtually any method by which DNA can be introduced into a cell, such as by direct delivery of DNA (e.g., by PEG-mediated transformation of protoplasts, by electroporation, by agitation with silicon carbide fibers, and by acceleration of DNA coated particles), by *Agrobacterium*-mediated transformation, by viral or other vectors, etc. One preferred method of plant transformation is microprojectile bombardment, for example, as illustrated in U.S. Pat. No. 5,015,580 (soy), 5,550,318 (maize), 5,538,880 (maize), 6,153,812 (wheat), 6,160,208 (maize), 6,288,312 (rice) and 6,399,861 (maize), and 6,403,865 (maize), all of which are incorporated by reference.

Another preferred method of plant transformation is *Agrobacterium*-mediated transformation. In one preferred embodiment, the non-natural transgenic plant cell of this invention is obtained by transformation by means of *Agrobacterium* containing a binary Ti plasmid system, wherein the *Agrobacterium* carries a first Ti plasmid and a second, chimeric plasmid containing at least one T-DNA border of a wild-type Ti plasmid, a promoter functional in the transformed plant cell and operably linked to a gene suppression construct of the invention. See, for example, the binary system described in U.S. Pat. No. 5,159,135, incorporated by reference. Also see De Framond (1983) *Biotechnology,* 1:262-269; and Hoekema et al., (1983) *Nature,* 303:179. In such a binary system, the smaller plasmid, containing the T-DNA border or borders, can be conveniently constructed and manipulated in a suitable alternative host, such as *E. coli*, and then transferred into *Agrobacterium.*

Detailed procedures for *Agrobacterium*-mediated transformation of plants, especially crop plants, include, for example, procedures disclosed in U.S. Pat. Nos. 5,004,863, 5,159,135, 5,518,908, 5,846,797, and 6,624,344 (cotton); U.S. Pat. Nos. 5,416,011, 5,569,834, 5,824,877, 5,914,451 6,384,301, and 7,002,058 (soy); U.S. Pat. Nos. 5,591,616 5,981,840, and 7,060,876 (maize); U.S. Pat. Nos. 5,463,174 and 5,750,871 (brassicas, including rapeseed and canola), and in U.S. Patent Application Publications 2004/0244075 (maize), 2004/0087030 (cotton) and 2005/0005321 (soy), all of which are incorporated by reference. Additional procedures for *Agrobacterium*-mediated transformation are disclosed in WO9506722 (maize). Similar methods have been reported for many plant species, both dicots and monocots, including, among others, peanut (Cheng et al. (1996) *Plant Cell Rep.,* 15: 653); asparagus (Bytebier et al. (1987) *Proc. Natl. Acad. Sci. U.S.A.,* 84:5345); barley (Wan and Lemaux (1994) *Plant Physiol.,* 104:37); rice (Toriyama et al. (1988) *Bio/Technology,* 6:10; Zhang et al. (1988) *Plant Cell Rep.,* 7:379; wheat (Vasil et al. (1992) *Bio/Technology,* 10:667; Becker et al. (1994) *Plant J.,* 5:299), alfalfa (Masoud et al. (1996) *Transgen. Res.,* 5:313); brassicas (Radke et al. (1992) *Plant Cell Rep.,* 11:499-505); and tomato (Sun et al. (2006) *Plant Cell Physiol.,* 47:426-431). See also a description of vectors, transformation methods, and production of transformed *Arabidopsis thaliana* plants where transcription factors are constitutively expressed by a CaMV35S promoter, in U.S. Patent Application Publication 2003/0167537 A1, incorporated by reference. Non-natural transgenic plant cells and transgenic plants can also be obtained by transformation with other vectors, such as, but not limited to, viral vectors (e.g., tobacco etch potyvirus (TEV), barley stripe mosaic virus (BSMV), and the viruses referenced in Edwardson and Christie, "The Potyvirus Group: Monograph No. 16, 1991, Agric. Exp. Station, Univ. of Florida), plasmids, cosmids, YACs (yeast artificial chromosomes), BACs (bacterial artificial chromosomes) or any other suitable cloning vector, when used with an appropriate transformation protocol, e.g., bacterial infection (e.g., with *Agrobacterium* as described above), binary bacterial artificial chromosome constructs, direct delivery of DNA (e.g., via PEG-mediated transformation, desiccation/inhibition-mediated DNA uptake, electroporation, agitation with silicon carbide fibers, and microproj ectile bombardment). It would be clear to one of ordinary skill in the art that various transformation methodologies can be used and modified for production of stable transgenic plants from any number of plant species of interest.

Transformation methods to provide non-natural transgenic plant cells and non-natural transgenic plants containing stably integrated recombinant DNA are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos or parts of embryos, and gametic cells such as microspores, pollen, sperm, and egg cells. Any cell from which a fertile plant can be regenerated is contemplated as a useful recipient cell for practice of the invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making transgenic plants of this invention (e.g., various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189, which are incorporated by reference.

In general transformation practice, DNA is introduced into only a small percentage of target cells in any one transformation experiment. Marker genes are generally used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is integrated and expressed at sufficient levels to permit cell survival. Cells can be tested further to confirm stable integration of the recombinant DNA. Commonly used selective marker genes include those conferring resistance to antibiotics such as kanamycin or paromomycin (nptII), hygromycin B (aph IV) and gentamycin (aac3 and aacC4) or resistance to herbicides such as glufosinate (bar or pat), glyphosate (EPSPS), and dicamba. Examples of useful selective marker genes and selection agents are illustrated in U.S. Pat. Nos. 5,550,318, 5,633,435, 5,780,708, and 6,118,047, all of which are incorporated by reference. A particularly preferred herbicide resistance gene is a glyphosate acetyl transferase, disclosed as SEQ ID NO. 68 in U.S. Patent Application Publication 2007/0079393 A1, which is specifically incorporated by reference. Screenable markers or reporters, such as markers that provide an ability to visually identify transformants can also be employed. Non-limiting examples of useful screenable markers include, for example, a gene expressing a protein that produces a detectable color by acting on a chromogenic substrate (e.g., beta-glucuronidase (GUS) (uidA) or luciferase (luc)) or that itself is detectable, such as green fluorescent protein (GFP) (gi) or an immunogenic molecule. Those of skill in the art will recognize that many other useful markers or reporters are available for use.

Detecting or measuring transcription of the recombinant DNA construct in the non-natural transgenic plant cell of the invention can be achieved by any suitable method, including protein detection methods (e.g., western blots, ELISAs, and other immunochemical methods), measurements of enzymatic activity, or nucleic acid detection methods (e.g., Southern blots, northern blots, PCR, RT-PCR, fluorescent in situ hybridization). Such methods are well known to those of ordinary skill in the art as evidenced by the numerous handbooks available; see, for example, Joseph Sambrook and David W. Russell, "Molecular Cloning: A Laboratory Manual" (third edition), Cold Spring Harbor Laboratory Press, N Y, 2001; Frederick M. Ausubel et al. (editors) "Short Protocols in Molecular Biology" (fifth edition), John Wiley and Sons, 2002; John M. Walker (editor) "Protein Protocols Handbook" (second edition), Humana Press, 2002; and Leandro Peña (editor) "Transgenic Plants: Methods and Protocols", Humana Press, 2004.

Other suitable methods for detecting or measuring transcription of the recombinant DNA construct in the non-natural transgenic plant cell of the invention include measurement of any other trait that is a direct or proxy indication of suppression of the target gene in the transgenic plant cell in which the recombinant DNA construct is transcribed, relative to one in which the recombinant DNA is not transcribed, e.g., gross or microscopic morphological traits, growth rates, yield, reproductive or recruitment rates, resistance to pests or pathogens, or resistance to biotic or abiotic stress (e.g., water deficit stress, salt stress, nutrient stress, heat or cold stress). Such methods can use direct measurements of a phenotypic trait or proxy assays (e. g., in plants, these assays include plant part assays such as leaf or root assays to determine tolerance of abiotic stress). Non-limiting methods include direct measurements of resistance to the invertebrate pest (e.g., damage to plant tissues) or proxy assays (e.g., plant yield assays, or bioassays such as the Western corn rootworm (*Diabrotica virgifera virgifera* LeConte) larval bioassay described in International Patent Application Publication WO2005/110068 A2 and U.S. Patent Application Publication US 2006/0021087 A1, incorporated by reference, or the soybean cyst nematode bioassay described by Steeves et al. (2006) *Funct. Plant Biol.,* 33:991-999, wherein cysts per plant, cysts per gram root, eggs per plant, eggs per gram root, and eggs per cyst are measured.

The recombinant DNA constructs of the invention can be stacked with other recombinant DNA for imparting additional traits (e.g., in the case of transformed plants, traits including herbicide resistance, pest resistance, cold germination tolerance, water deficit tolerance, and the like) for example, by expressing or suppressing other genes. Constructs for coordinated decrease and increase of gene expression are disclosed in U.S. Patent Application Publication 2004/0126845 A1, incorporated by reference.

Seeds of transgenic, fertile plants can be harvested and used to grow progeny generations, including hybrid generations, of non-natural transgenic plants of this invention that include the recombinant DNA construct in their genome. Thus, in addition to direct transformation of a plant with a recombinant DNA construct of this invention, non-natural transgenic plants of the invention can be prepared by crossing a first plant having the recombinant DNA with a second plant lacking the construct. For example, the recombinant DNA can be introduced into a plant line that is amenable to transformation to produce a transgenic plant, which can be crossed with a second plant line to introgress the recombinant DNA into the resulting progeny. A transgenic plant of the invention can be crossed with a plant line having other recombinant DNA that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s).

Typically, in such breeding for combining traits the transgenic plant donating the additional trait is a male line and the transgenic plant carrying the base traits is the female line. The progeny of this cross segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, e.g., usually 6 to 8 generations, to produce a progeny plant with substantially the same genotype as one original transgenic parental line but for the recombinant DNA of the other transgenic parental line.

Yet another aspect of the invention is a non-natural transgenic plant grown from the non-natural transgenic seed of the invention. This invention contemplates transgenic plants grown directly from transgenic seed containing the recombinant DNA as well as progeny generations of plants, including inbred or hybrid plant lines, made by crossing a transgenic plant grown directly from transgenic seed to a second plant not grown from the same transgenic seed.

Crossing can include, for example, the following steps:

(a) plant seeds of the first parent plant (e.g., non-transgenic or a transgenic) and a second parent plant that is transgenic according to the invention;
(b) grow the seeds of the first and second parent plants into plants that bear flowers;
(c) pollinate a flower from the first parent with pollen from the second parent; and
(d) harvest seeds produced on the parent plant bearing the fertilized flower.

It is often desirable to introgress recombinant DNA into elite varieties, e.g., by backcrossing, to transfer a specific desirable trait from one source to an inbred or other plant that lacks that trait. This can be accomplished, for example, by first crossing a superior inbred ("A") (recurrent parent) to a donor inbred ("B") (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent "B", and then the selected progeny are mated back to the superior recurrent parent "A". After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e., one or more transformation events.

Through a series of breeding manipulations, a selected DNA construct can be moved from one line into an entirely different line without the need for further recombinant manipulation. One can thus produce inbred plants which are true breeding for one or more DNA constructs. By crossing different inbred plants, one can produce a large number of different hybrids with different combinations of DNA constructs. In this way, plants can be produced which have the desirable agronomic properties frequently associated with hybrids ("hybrid vigor"), as well as the desirable characteristics imparted by one or more DNA constructs.

Genetic markers can be used to assist in the introgression of one or more DNA constructs of the invention from one genetic background into another. Marker assisted selection offers advantages relative to conventional breeding in that it can be used to avoid errors caused by phenotypic variations. Further, genetic markers can provide data regarding the relative degree of elite germplasm in the individual progeny of a particular cross. For example, when a plant with a desired trait which otherwise has a non-agronomically desirable genetic background is crossed to an elite parent, genetic markers can be used to select progeny which not only possess the trait of interest, but also have a relatively large proportion of the desired germplasm. In this way, the number of generations required to introgress one or more traits into a particular genetic background is minimized. The usefulness of marker assisted selection in breeding non-natural transgenic plants of the current invention, as well as types of useful molecular markers, such as but not limited to SSRs and SNPs, are discussed in PCT Application Publication WO 02/062129 and U.S. Patent Application Publications Numbers 2002/0133852, 2003/0049612, and 2003/0005491, each of which is incorporated by reference in their entirety.

In certain non-natural transgenic plant cells and non-natural transgenic plants of the invention, it may be desirable to concurrently express (or suppress) a gene of interest while also regulating expression of a target gene. Thus, in some embodiments, the transgenic plant contains recombinant DNA including both a transgene transcription unit for expressing at least one gene of interest and a gene suppression element for suppressing a target gene.

Thus, as described herein, the non-natural transgenic plant cells or non-natural transgenic plants of the invention can be obtained by use of any appropriate transient or stable, integrative or non-integrative transformation method known in the art or presently disclosed. The recombinant DNA constructs can be transcribed in any plant cell or tissue or in a whole plant of any developmental stage. Transgenic plants can be derived from any monocot or dicot plant, such as, but not limited to, plants of commercial or agricultural interest, such as crop plants (especially crop plants used for human food or animal feed), wood-, fiber-, pulp-, or cellulose-producing trees and plants, vegetable plants, fruit plants, and ornamental plants. Non-limiting examples of plants of interest include grain crop plants (such as wheat, oat, barley, maize, rye, triticale, rice, millet, sorghum, *quinoa*, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, macadamia, and the like); sugarcane, coconut, date palm, olive, sugarbeet, tea, and coffee; wood-, fiber-, pulp-, or cellulose-producing trees and plants (for example, cotton, flax, jute, ramie, sisal, kenaf, switchgrass, and bamboo); vegetable crop plants such as legumes (for example, beans, peas, lentils, alfalfa, peanut), lettuce, asparagus, artichoke, celery, carrot, radish, cassava, sweet potato, yam, cocoa, coffee, tea, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, *quinoa*, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, *papaya*, avocado, fig, mango, and berries; and ornamental plants including ornamental flowering plants, ornamental trees and shrubs, ornamental groundcovers, and ornamental grasses. Preferred dicot plants include, but are not limited to, canola, broccoli, cabbage, carrot, cauliflower, Chinese cabbage, cucumber, dry beans, eggplant, fennel, garden beans, gourds, lettuces, melons, okra, peas, peppers, pumpkin, radishes, spinach, squash, watermelon, cotton, potato, *quinoa*, amaranth, buckwheat, safflower, soybean, sugarbeet, and sunflower. Preferred monocots include, but are not limited to, wheat, oat, barley, maize (including sweet corn and other varieties), rye, triticale, rice, ornamental and forage grasses, sorghum, millet, onions, leeks, and sugarcane, more preferably maize, wheat, and rice.

The ultimate goal in plant transformation is to produce plants which are useful to man. In this respect, non-natural transgenic plants of the invention can be used for virtually any purpose deemed of value to the grower or to the consumer. For example, one may wish to harvest the transgenic plant itself, or harvest transgenic seed of the transgenic plant for planting purposes, or products can be made from the transgenic plant or its seed such as oil, starch, ethanol or other fermentation products, animal feed or human food, pharmaceuticals, and various industrial products. For example, maize is used extensively in the food and feed industries, as well as in industrial applications. Further discussion of the uses of maize can be found, for example, in U.S. Pat. Nos. 6,194,636, 6,207,879, 6,232,526, 6,426,446, 6,429,357, 6,433,252, 6,437,217, and 6,583,338, incorporated by reference, and PCT Publications WO 95/06128 and WO 02/057471. Thus, this invention also provides commodity products produced from a non-natural transgenic plant cell, plant, or seed of this invention, including, but not limited to, harvested leaves, roots, shoots, tubers, stems, fruits, seeds, or other parts of a plant, meals, oils, extracts, fermentation or digestion products, crushed or whole grains or seeds of a plant, or any food or non-food product including such commodity products produced from a transgenic plant cell, plant, or seed of this invention. The detection of one or more of nucleic acid sequences of the recombinant DNA constructs of this invention in one or more commodity or commodity products contemplated herein is de facto evidence that the commodity or commodity product contains or is derived from a transgenic plant cell, plant, or seed of this invention.

In preferred embodiments, the non-natural transgenic plant prepared from the non-natural transgenic plant cell of this invention, i.e., a transgenic plant having in its genome a recombinant DNA construct of this invention has at least one additional altered trait, relative to a plant lacking the recombinant DNA construct, selected from the group of traits consisting of:

(a) improved abiotic stress tolerance;
(b) improved biotic stress tolerance;
(c) modified primary metabolite composition;
(d) modified secondary metabolite composition;
(e) modified trace element, carotenoid, or vitamin composition;
(f) improved yield;
(g) improved ability to use nitrogen or other nutrients;
(h) modified agronomic characteristics;
(i) modified growth or reproductive characteristics; and
(j) improved harvest, storage, or processing quality.

In particularly preferred embodiments, the non-natural transgenic plant is characterized by: improved tolerance of abiotic stress (e.g., tolerance of water deficit or drought, heat, cold, non-optimal nutrient or salt levels, non-optimal light levels) or of biotic stress (e.g., crowding, allelopathy, or wounding); by a modified primary metabolite (e.g., fatty acid, oil, amino acid, protein, sugar, or carbohydrate) composition; a modified secondary metabolite (e.g., alkaloids, terpenoids, polyketides, non-ribosomal peptides, and secondary metabolites of mixed biosynthetic origin) composition; a modified trace element (e.g., iron, zinc), carotenoid (e.g., beta-carotene, lycopene, lutein, zeaxanthin, or other carotenoids and xanthophylls), or vitamin (e. g., tocopherols) composition; improved yield (e.g., improved yield under non-stress conditions or improved yield under biotic or abiotic stress); improved ability to use nitrogen or other nutrients; modified agronomic characteristics (e.g., delayed ripening; delayed senescence; earlier or later maturity; improved shade tolerance; improved resistance to root or stalk lodging; improved resistance to "green snap" of stems; modified photoperiod response); modified growth or reproductive characteristics (e.g., intentional dwarfing; intentional male sterility, useful, e.g., in improved hybridization procedures; improved vegetative growth rate; improved germination; improved male or female fertility); improved harvest, storage, or processing quality (e.g., improved resistance to pests during storage, improved resistance to breakage, improved appeal to consumers); or any combination of these traits.

In one preferred embodiment, non-natural transgenic seed, or seed produced by the non-natural transgenic plant, has modified primary metabolite (e.g., fatty acid, oil, amino acid, protein, sugar, or carbohydrate) composition, a modified secondary metabolite (e.g., alkaloids, terpenoids, polyketides, non-ribosomal peptides, and secondary metabolites of mixed biosynthetic origin) composition, a modified trace element (e.g., iron, zinc, sulfur), organic phosphate (e. g, phytic acid), carotenoid (e.g., beta-carotene, lycopene, lutein, zeaxanthin, or other carotenoids and xanthophylls), or vitamin (e.g., tocopherols) composition, an improved harvest, storage, or processing quality, or a combination of these. For example, it can be desirable to modify the amino acid (e.g., lysine, methionine, tryptophan, or total protein), oil (e.g., fatty acid composition or total oil), carbohydrate (e.g., simple sugars or starches), trace element, carotenoid, or vitamin content of seeds of crop plants (e.g., canola, cotton, safflower, soybean, sugarbeet, sunflower, wheat, maize, or rice), preferably in combination with improved seed harvest, storage, or processing quality, and thus provide improved seed for use in animal feeds or human foods. In another example, it can be desirable to modify the quantity or quality of polysaccharides (e.g., starch, cellulose, or hemicellulose) in plant tissues for use in animal feeds or human foods or for fermentation or biofuel production. In another instance, it can be desirable to change levels of native components of the transgenic plant or seed of a transgenic plant, for example, to decrease levels of proteins with low levels of lysine, methionine, or tryptophan, or to increase the levels of a desired amino acid or fatty acid, or to decrease levels of an allergenic protein or glycoprotein (e. g., peanut allergens including ara h 1, wheat allergens including gliadins and glutenins, soy allergens including P34 allergen, globulins, glycinins, and conglycinins) or of a toxic metabolite (e.g., cyanogenic glycosides in cassava, solanum alkaloids in members of the Solanaceae).

EXAMPLES

Example 1

This example describes a non-limiting embodiment of DNA encoding a transcript that folds into hybridized RNA that is cleaved in phase in vivo into multiple small double-stranded RNAs for gene suppression. More specifically, this example provides nucleic acid sequences, obtained from monocot crop plants, that are useful in making a single recombinant DNA molecule encoding a transcript that folds into hybridized RNA that is cleaved in phase in vivo into multiple small double-stranded RNAs for gene suppression, independently of an RNA-dependent RNA polymerase.

Several RNA libraries were cloned from mature rice (*Oryza sativa*) grain and from various maize (*Zea mays*) tissues by high-throughput sequencing (Margulies et al. (2005) *Nature,* 437:376-380). Among the most abundant sequences cloned from mature rice grain and maize root, 32 DAP (days after pollinations) and 39 DAP kernels were seven 21-mer RNAs (SEQ ID NO. 1, SEQ ID NO. 2, SEQ ID NO. 3, SEQ ID NO. 4, SEQ ID NO. 5, SEQ ID NO. 6, and SEQ ID NO. 7), listed in Table 1.

TABLE 1

| SEQ ID NO. | Clone number | DNA sequence | Species/ Tissue* |
|---|---|---|---|
| 1 | 141121 | ATGCAAGT GATGTAGC GCCCC | rice grain, maize root, maize 32DAP and 39DAP kernel |
| 2 | 297263 | ATATAGGA GTCACTCA GGAAA | rice grain, maize 32DAP kernel |
| 3 | 1196700 | TCTTTGCC CTCTTTAG TGCTT | rice grain, maize 32DAP kernel |
| 4 | 880479 | TATGGATG GGCACCAT CTTCA | rice grain, maize 32DAP kernel |
| 5 | 1275002 | TGGCCACC AACAACAT CAGCA | rice grain, maize 32DAP kernel |
| 6 | 1379342 | TGCCCCAC CAAGAGAA CGCCG | rice grain, maize root, maize leaf, maize 32DAP and 39DAP kernel |
| 7 | 544819 | TGCCTGAG GAACACCA CCAGG | rice grain, maize root, maize 32DAP and 39DAP kernel |

*DAP, days after pollination

These seven 21-mer RNAs, when aligned to the rice genome at locus Os6g21900, were located in two adjacent regions containing seven and six 21-nt siRNAs aligned end to end, respectively, and forming a single foldback structure depicted in FIG. 1. No siRNAs from this gene were present in other libraries, and only a very small number were sequenced from the putative loop region between arms of the foldback structure. Additional sequencing results indicated that this foldback structure contained at least three other potential 21-mer RNAs (in phase with and distal to the first seven 21-mers and loop), although small RNAs predicted to result from in vivo cleavage of these additional phased small double-stranded RNAs were cloned only at low abundances.

Although many variants of small RNAs were identified, only a single unique 21-nucleotide (21-nt) phase from the plus strand was supported by sequence information (Table 2). "Phase fullness" indicates how many 21-nt phases are occupied by sequenced small RNAs in both strands; for example, a fullness of 0.5 for frame 7.0 with a phase length of 8 indicates that all eight 21-nt frames are occupied in the plus strand, but none are occupied in the hypothetical minus strand. "Phase uniqueness" represents a probability score for phased small RNAs, which takes into account phase occupancy and abundance of small RNAs in each phase. Frame 16.1 and Frame 7.0 represent each side of the foldback structure (depicted in FIG. 1, with the first seven phased small RNAs shown) and its abundant phased small RNAs; phasing is highly supported (uniqueness >0.97) for this structure, whereas all other potential small RNA phases were poorly supported by sequence data (uniqueness <0.005).

TABLE 2

| Frame | Start (phase number) | Phase length | Phase fullness | Phase uniqueness | Small RNA abundance | Average copies |
|---|---|---|---|---|---|---|
| 16.1 | 5099(1), 5120(2), 5141(3), 5162(4), 5183(5), 5204(6), 5246(8) | 8 | 0.43 | 0.9963 | 344, 89484, 3393, 3121, 10455, 71, 31 | 15271 |
| 7.0 | 3620(1), 3641(2), 3662(3), 3683(4), 3704(5), 3725(6), 3746(7), 3767(8) | 8 | 0.5 | 0.9717 | 67, 6875, 1289, 3, 151, 7, 67, 11619 | 2510 |
| 19.0 | 3611(1), −3630(2), −3651(3), 3653(3), −3693(5), −3714(6), −3735(7), 3737(7), −3756(8), 3758(8) | 8 | 0.62 | 0.0049 | 27, 1, 1, 59, 1, 3, 6, 2, 1, 1 | 10 |
| 16.0 | 3629(1), 3650(2), 3671(3), −3711(5), 3713(5) | 5 | 0.5 | 0.0013 | 1, 5, 2, 2, 2 | 2 |
| 4.0 | 3638(1), 3680(3), 3722(5), −3741(6), 3764(7) | 7 | 0.35 | 0.0011 | 17, 1, 2, 2, 1 | 5 |
| 18.0 | −5120(1), 5122(1), −5141(2), 5164(3), 5185(4) | 4 | 0.62 | 0.001 | 1, 15, 1, 73, 17 | 21 |

TABLE 2-continued

| Frame | Start (phase number) | Phase length | Phase fullness | Phase uniqueness | Small RNA abundance | Average copies |
|---|---|---|---|---|---|---|
| 6.0 | 3640(1), 3661(2), 3682(3), 3724(5), 3745(6), 3766(7) | 7 | 0.42 | 0.0008 | 9, 3, 1, 1, 2, 2 | 3 |
| 15.0 | 5140(1), 5161(2), 5182(3), 5203(4) | 4 | 0.5 | 0.0007 | 1, 71, 4, 4 | 20 |
| 14.0 | 3669(1), 3711(3), 3753(5) | 5 | 0.3 | 0.0006 | 1, 6, 1 | 3 |
| 11.0 | 5199(1), 5220(2), 5262(4) | 4 | 0.37 | 0.0004 | 1, 3, 1 | 2 |
| 20.0 | 3654(1), 3675(2), −3736(5), 3780(7) | 7 | 0.28 | 0.0003 | 2, 2, 1, 2 | 2 |
| 3.0 | 3637(1), 3658(2), 3700(4), 3721(5), −3740(6) | 6 | 0.41 | 0.0003 | 2, 1, 2, 1, 1 | 1 |

The genomic sequence and putative precursors for the *Oryza sativa* foldback structure are given in SEQ ID NO. 8, SEQ ID NO. 9, SEQ ID NO. 10, and SEQ ID NO. 11. One genomic DNA sequence (SEQ ID NO. 9) was predicted to include the cDNA sequence, intronic sequence, and foldback arms as shown in FIG. 2, and several alternatively spliced versions of this transcript were found in cDNA databases. One abundant alternatively spliced transcript (SEQ ID NO. 10) indicates removal of one half of the foldback structure, probably preventing small RNA production. An expressed sequence tag (SEQ ID NO. 11) was identified as representing the complementary sequence to SEQ ID NO. 10. A canonical TATA box (indicated by the boxed nucleotides in FIG. 2) is located 34 bases upstream of the predicted transcription start site in SEQ ID NO. 8, evidence that this is the bona fide 5' end of the transcript. A single foldback structure is thus transcribed from one promoter and forms, independently of an RNA-dependent RNA polymerase, the hybridized RNA that is cleaved in phase in vivo into multiple small double-stranded RNAs for gene suppression. Alternatively, two (or more) splicing variants transcribed from the same promoter each contains one of each of the arms of the foldback structure, and come together in trans, independently of an RNA-dependent RNA polymerase, to form the hybridized RNA that is cleaved in phase in vivo into multiple small double-stranded RNAs.

The evidence collected supports this locus as a novel type of RNA-mediated regulatory (suppression) element. Unlike trans-acting siRNAs, all of the multiple small double-stranded RNAs derive from the original RNA transcript or plus strand of the precursor, independently of an RNA-dependent RNA polymerase and without a miRNA target site that initiates production of double-stranded RNA. Unlike microRNAs, the locus is cleaved in vivo to multiple abundant phased small RNAs, and (as described below in Example 5), this process requires DCL4 (or a DCL4 orthologue) and not DCL1. The inventors therefore term this novel locus a "phased small RNA" locus.

Expression of this particular phased small RNA locus appears to be restricted primarily to mature grain in both maize and rice, indicating an endogenous function related to repression of genes involved in maturation or maintenance of the embryogenic state in mature grain. Putative targets were predicted for each of the seven phased small RNAs (SEQ ID NO. 1, SEQ ID NO. 2, SEQ ID NO. 3, SEQ ID NO. 4, SEQ ID NO. 5, SEQ ID NO. 6, and SEQ ID NO. 7), following target prediction guidelines described in Allen et al. (2005) *Cell,* 121:207-221. Non-limiting examples of these targets, which include members of the HAK2 high affinity potassium transporter family, are given in Table 3; the corresponding maize loci from the public database, Maize Assembled Genomic Island (available on line at magi.plantgenomics.iastate.edu, see Fu et al. (2005) *Proc. Natl. Acad. Sci. USA,* 102:12282-12287) are also provided.

TABLE 3

| SEQ ID NO. | Clone number | DNA sequence | Target gene (rice) | Maize locus* | E value |
|---|---|---|---|---|---|
| 3 | 1196700 | TCTTTGCC CTCTTTAG TGCTT | Os01g12300 Protein kinase domain | MAGI4_89402 | 3.00E-24 |
| | | | | MAGI4_122217 | 7.00E-19 |
| | | | | MAGI4_104144 | 1.00E-17 |
| | | | | MAGI4_99444 | 1.00E-14 |
| | | | | MAGI4_39748 | 2.00E-14 |
| | | | | MAGI4_22926 | 3.00E-14 |
| | | | Os12g17310 myosin heavy chain | MAGI4_70672 | 0 |
| | | | | MAGI4_141564 | 0 |
| 5 | 1275002 | TGGCCACC AACAACAT CAGCA | Os09g29660 ABC-2 type transporter | MAGI4_27534 | 2.00E-22 |
| | | | Os01g70940 Potassium transporter 7 | MAGI4_99444 | 0 |
| | | | Os09g27580 potassium uptake protein | MAGI4_99444 | 3.00E-68 |
| | | | Os08g38980 Chloride channel protein | MAGI4_25450 | e-127 |

*publicly available at magi.plantgenomics.iastate.edu

Example 2

This example describes a non-limiting embodiment of a recombinant DNA construct including a promoter operably linked to DNA that transcribes to RNA including: (a) at least one exogenous recognition site recognizable by a phased small RNA expressed in a specific cell of a multicellular eukaryote, and (b) target RNA to be suppressed in the specific cell, wherein the target RNA is to be expressed in cells of the multicellular eukaryote other than the specific cell. More specifically, this example describes a recombinant DNA construct including DNA that transcribes to RNA containing an exogenous recognition site corresponding to at least one phased small RNA derived from an endogenous phased small RNA locus.

Recombinant DNA constructs were designed to include a gene expression element for expression of a gene of interest (in this non-limiting example, the reporter gene, beta-glucoronidase, "GUS"), and a recognition site (target site) corresponding to at least one phased small RNA of this invention (e.g., any one or more of SEQ ID NO. 1, SEQ ID NO. 2, SEQ ID NO. 3, SEQ ID NO. 4, SEQ ID NO. 5, SEQ ID NO. 6, and SEQ ID NO. 7 as described in Example 1). Similar recombinant DNA constructs can be designed, wherein a recognition site (target site) corresponding to at least one phased small RNA of this invention is included to regulate the expression of a gene expression element for the expression of a gene of interest (which can be translatable or coding sequence or non-coding sequence, including regulatory sequence), e.g., those described under the heading "Target Genes", or alternatively to regulate the expression of a gene suppression element (e.g., sense, anti-sense, combinations of sense and anti-sense, tandem repeats of sense or of anti-sense, microRNAs, siRNAs, and any other construct designed to reduce the expression of a target gene).

A control construct (pMON94320) with a 35S promoter driving expression of GUS and an Hsp17 terminator included the partial sequence SEQ ID NO. 12, with an insertion site (indicated in bold font in FIG. 3B) located between the GUS coding sequence and the Hsp17 terminator. Three additional constructs based on this control construct were designed, each containing at least one recognition site corresponding to a phased small RNA of this invention. The first construct (pMON100574) included the partial sequence SEQ ID NO. 13, which contained one of the 21-mer phased small RNAs (SEQ ID NO. 6) described in Example 1, incorporated in the sense orientation at the insertion site (FIG. 3C). The second construct (pMON100575) included the partial sequence SEQ ID NO. 14, which contained one of the 21-mer phased small RNAs (SEQ ID NO. 6) described in Example 1, incorporated in the anti-sense orientation (i.e., as a recognition site corresponding to SEQ ID NO. 6 in the sense orientation) at the insertion site (FIG. 3D). The third construct (pMON100576) included the partial sequence SEQ ID NO. 15, which contained two of the 21-mer phased small RNAs (SEQ ID NO. 5 and SEQ ID NO. 6) described in Example 1, both incorporated in the anti-sense orientation (i.e., as recognition sites corresponding to SEQ ID NO. 5 and SEQ ID NO. 6 in the sense orientation) at the insertion site (FIG. 3E).

Maize tissue from developing kernels was analyzed by northern blot using a single probe with the sequence CGGCGTTCTCTTGGTGGGGCA (SEQ ID NO. 16, i.e., the anti-sense sequence of SEQ ID NO. 6). The results, depicted in FIG. 4, indicated transcription of the endogenous maize phased small RNA locus, especially in developing embryo and to a lower extent in developing endosperm, further corroborating the cloning results given in Table 1.

Maize zygotic embryos (21-22 days after pollination) were transformed with the recombinant DNA constructs by particle bombardment, using about 0.5 micrograms DNA delivered with one shot of a helium particle gun. Bombarded tissue was incubated for 24 or 48 hours in a dark reach-in growth chamber at 26 degrees Celsius. The embryos were stained in 5-bromo-4-chloro-3-indolyl-beta-D-glucuronic acid solution (24 hours at 37 degrees Celsius) followed by clearing of the stained tissue in 70% ethanol. Expression of the gene of interest (GUS) encoded by the gene expression element was indicated by the level of staining in the embryos; GUS expression was predicted to be silenced by the endogenous maize phased small RNA locus. As predicted, GUS expression was silenced in the embryos transformed with the constructs (pMON100575 and pMON100576) containing at least one recognition site corresponding to a phased small RNA of this invention (FIG. 3A). The silencing observed in the embryos transformed with pMON100574 was presumably due to endogenous anti-sense transcript present in low abundance as was observed in the cloned rice RNA libraries (see Table 2 for abundances of cloned small RNAs).

Recognition sites corresponding to phased small RNAs of this invention are useful for regulating expression of a transgene in a construct including at least one such recognition site. Thus, this invention provides a recombinant DNA construct including a promoter operably linked to DNA that transcribes to RNA including: (a) at least one exogenous recognition site recognizable by a phased small RNA expressed in a specific cell of a multicellular eukaryote, and (b) target RNA to be suppressed in the specific cell, wherein the target RNA is to be expressed in cells of the multicellular eukaryote other than the specific cell. The invention includes a recombinant DNA construct including a transgene and at least one recognition site that corresponds to one or more phased small RNAs of this invention, useful for expression of that transgene in tissues other than those in which the phased small RNAs are expressed, and suppression of the transgene in tissues where the phased small RNAs are expressed. For example, SEQ ID NO. 6 has been shown to be expressed in rice kernel (Example 1) and in corn kernel (this example); a construct containing a transgene (e.g., an herbicide tolerance gene such as 5-enolpyruvylshikimate-3-phosphate synthase) and at least one recognition site corresponding to SEQ ID NO. 6 is useful for suppression of the transgene in at least rice or corn kernel.

Example 3

This example describes a non-limiting embodiment of a recombinant DNA construct including DNA that transcribes to: (a) a first series of contiguous RNA segments, and (b) a second series of contiguous RNA segments, wherein the first series of contiguous RNA segments hybridize in vivo to the second series of RNA segments to form hybridized RNA that is cleaved in phase in vivo into multiple small double-stranded RNAs ("phased small RNAs") for gene suppression. Preferably the hybridized RNA is produced independently of an RNA-dependent RNA polymerase. The recombinant DNA construct of this invention can include a synthetic phased small RNA locus (which can transcribe to a longer or shorter transcript than that transcribed from a naturally occurring phased small RNA locus), designed to be cleaved in vivo and in phase into any number of phased small RNAs for suppression of one or more target genes.

This example provides an embodiment of a recombinant DNA construct including nucleic acid sequences derived from monocot crop plants, that transcribes to an RNA containing a single foldback structure cleavable in vivo and in phase to multiple small double-stranded RNAs for gene suppression, independently of an RNA-dependent RNA polymerase. A phased small RNA locus from monocot crops was found to have the single foldback structure depicted in FIG. 1 (see Example 1). This locus includes at least seven 21-mer RNAs (SEQ ID NO. 1, SEQ ID NO. 2, SEQ ID NO. 3, SEQ ID NO. 4, SEQ ID NO. 5, SEQ ID NO. 6, and SEQ ID NO. 7), each and any of which can be engineered to suppress expression of one target gene or of multiple target genes in trans. In this non-limiting example, a recombinant DNA construct based on this locus was designed to transcribe to a single transcript including an imperfect foldback structure for suppressing multiple endogenous genes in maize: (1) the messenger RNA encoding the LKR region of the lysine ketoglutarate reductase/saccharopine dehydrogenase gene, LKR/SDH, and (2) the messenger RNA encoding the dominant Waxy gene, which encodes an enzyme for starch synthesis; a "waxy" (non-starchy) mutant phenotype characterized by decreased amylose and increased amylopectin (branched starch) is typically seen in plants homozygous for the naturally occurring, recessive allele (wx/wx) and is useful as a visual marker of inheritance in maize breeding.

The recombinant DNA sequence was designed based on a 939-nucleotide starting sequence (SEQ ID NO. 17), which included, in order:

(1) a 5' leader sequence (SEQ ID NO. 18);

(2) the 5' arm of the foldback structure, including a first series of contiguous RNA segments, i.e., seven contiguous 21-mers (SEQ ID NO. 1, SEQ ID NO. 2, SEQ ID NO. 19, SEQ ID NO. 20, SEQ ID NO. 21, SEQ ID NO. 22, and SEQ ID NO. 7) in the order listed (5' to 3');

(3) spacer sequence (SEQ ID NO. 23) forming a loop joining the 5' and 3' arms of the foldback structure;

(4) the 3' arm of the foldback structure, including a second series of contiguous RNA segments, i.e., seven contiguous 21-mers (SEQ ID NO. 24, SEQ ID NO. 6, SEQ ID NO. 5, SEQ ID NO. 4, SEQ ID NO. 3, SEQ ID NO. 25, and SEQ ID NO. 26) in the order listed (5' to 3'); and (5) a 3' untranslated region and terminator (SEQ ID NO. 27)

This starting sequence (SEQ ID NO. 17) is useful as a phased small RNA template on which a gene suppression construct is based; any one or more of the contiguous 21-mers (or the contiguous RNA segments in the corresponding RNA transcript) that form the foldback structure can be modified or engineered to silence a target gene, as described above under the heading "A Recombinant DNA Construct Transcribing to a First and Second Series of Contiguous RNA Segments that Form Hybridized RNA that is Cleaved in Phase in vivo". In this non-limiting embodiment, the 21-mers engineered to silence one or more target genes are preferably selected from SEQ ID NO. 1, SEQ ID NO. 2, SEQ ID NO. 3, SEQ ID NO. 4, SEQ ID NO. 5, SEQ ID NO. 6, and SEQ ID NO. 7. Preferably, a spacer sequence (such as SEQ ID NO. 23) forming a loop joining the 5' and 3' arms of the foldback structure is maintained in the engineered gene suppression construct.

In one specific example, selected 21-mer sequences (synthetic phased small RNAs) were designed to target LKR (SEQ ID NO. 28, and SEQ ID NO. 29) or Waxy (SEQ ID NO. 30, and SEQ ID NO. 31), respectively. These are cloned into expressed phase locations of the template sequence to yield the gene suppression construct having the sequence (SEQ ID NO. 32)

aatcttattctacatatttctatcttatatagaacaactagcata
gctctcgttgcccagccaggttgcccagccaggttgcctggtgca
caatgagagctggctagggcggactcattctgctgttggtgccca
acgatgctagctgctactcatactagtgaagcctgccatggttct
gagaaattttggatactccgctgcgtagatatgcactaaaagct
tgtatgtttcgctgactacatactatggatatcacctgtttgaca
agagaaggattacataccacgatgaagatgaattggaacatgATG
CAAGTGATGTAGCGCCCCATATAGGAGTCACTCAGGAAAGCGCaG
CTCGCCAccGAGATGcGCCcAAGATGCAGGTGcATGCTGAcgcta
TTGGcGGCCtCGCATAGATCcCTTGATaTCACTTTGTgGATGCAG
AaAGCGGTGcccacggcgacgccaaaaaatgcaaagttggccaac
acatagctcactgcatcgtcaagtagagctgcttaatcactgagg
gtatatacatttagttcgccttcttcagcgttgccatggacaCCG
CTcTCTGCATCaACAAAGTGAcATCAAGtGATCTATGCGtGGCCa
CCAAcaacaTCAGCATaCACCTGCATCTTtGGCaCATCTCctTGG
CGAGCgGCGCttTCCGTAGTGATTCCTATACGGGGTGCTACTTCA
CTTGGATCAtgttacaatttatcttcatcgtgatatatgctcctt
ctgttctcacataggtgatatcttaaaatgtatgaggcatatata
ctttctacctaatattataaagtatatgcctctatatagatcaaa
taaagcagaaaagtcattgttattaccaatcgtgtacttttgttc
taaacatctcaactagtttaaagtatttgtctctcttga;

the 5' and 3' arms of the foldback structure are indicated by underlined text, engineered 21-mers are shown in bold font, and intentionally mismatched nucleotides are indicated by lower case font. Additional sequence on each foldback arm was also modified in order to preserve the original secondary structure (including the location of mismatched bases) of the template sequence (SEQ ID NO. 17). FIG. 5 depicts the predicted secondary structure of the RNA transcribed respectively from the template sequence (SEQ ID NO. 17) and from the engineered gene suppression construct (SEQ ID NO. 32). Expression of the engineered gene suppression construct is driven by an appropriate endosperm specific promoter, such as a maize zein or B32 promoter (nucleotides 848 through 1259 of GenBank accession number X70153, see also Hartings et al. (1990) *Plant Mol. Biol.,* 14:1031-1040, which is incorporated herein by reference). Additional synthetic phased small RNA constructs are designed in a similar manner to silence multiple target genes, such as combinations of endogenous genes (e.g., LKR/SDH, GLABRA1, DWARF4, and CLAVATA) or transgenes (e.g., reporter genes such as GUS or GFP, or selectable markers such as a gene imparting antibiotic or herbicide tolerance).

Example 4

This example describes a non-limiting embodiment of an RNA transcript that folds into hybridized RNA that is cleaved in phase in vivo into multiple small double-stranded RNAs for gene suppression, wherein the hybridized RNA is produced independently of an RNA-dependent RNA polymerase. More specifically, this example provides nucleic acid sequences, obtained from monocot crop plants, that are useful in making a recombinant DNA construct encoding a transcript that folds into hybridized RNA that is cleaved in phase in vivo into multiple small double-stranded RNAs for gene suppression, independently of an RNA-dependent RNA polymerase.

Figure 7A:
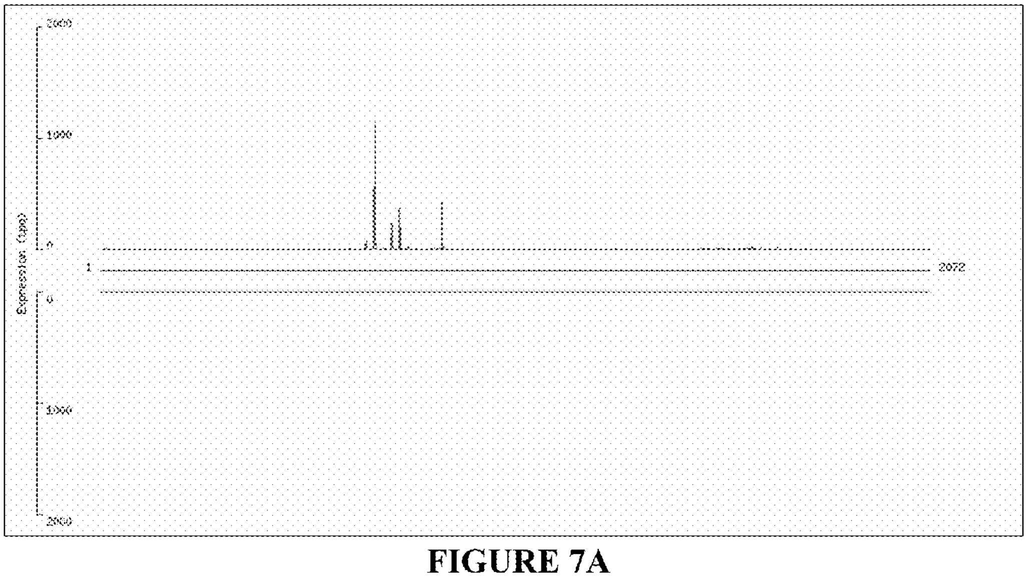
FIG. 7A depicts the small RNA abundance in transcripts per quarter million sequences ("tpq") along about 2 kilobases of the phased small RNA locus having the sequence of SEQ ID NO. 33, as described in Example 4.
Figure 7B:
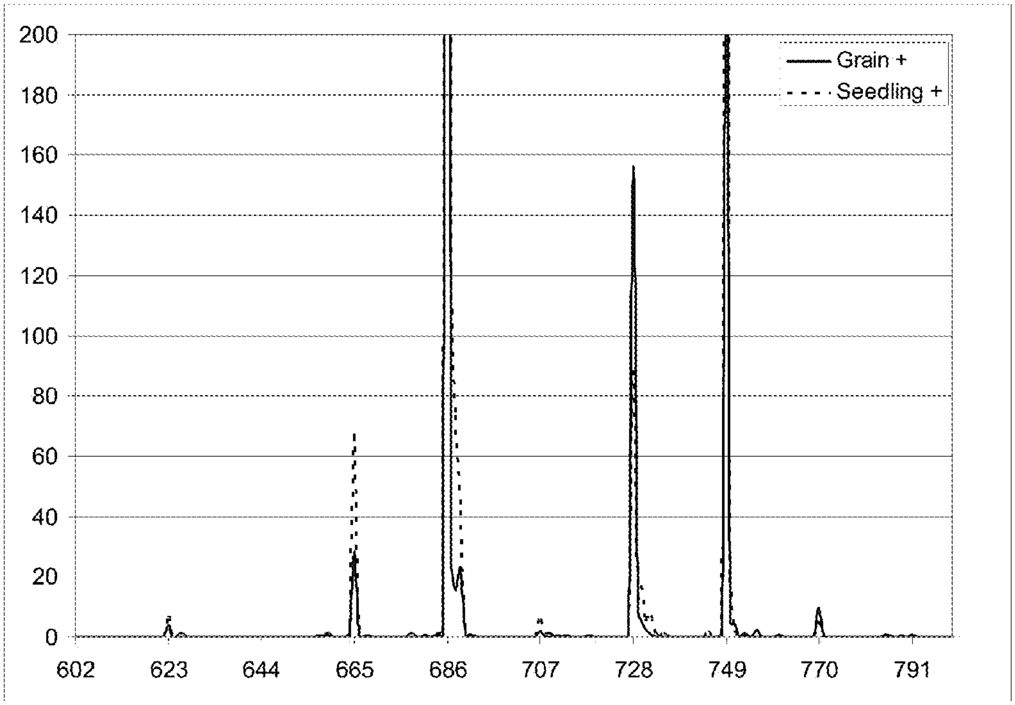
FIG. 7B depicts an expanded view of this small RNA region and the 21-nucleotide phasing of the small RNA abundance.

Following the methods described in detail in Example 1, a second "phased small RNA" locus was identified from rice (*Oryza sativa*) mature grain and seedling RNA libraries. This locus, LOC_Os12g42380.1|11982.m08017, had the DNA sequence GATTCTCCCCTGCGCCGCCGCCGC-CGCCGCCGCCTCAATCGGGCGAAGCCGCCCTCGC-CGCCG TCGCGGCGGCGGCGGCGAGGGCGAGCTC-CTGCGAGAGATCCTCCGCCGCCTCATGCCTCGCG CGCGCGCTCCCGCTCCCGCTCTCGCCTGCAGT-ATTTGTTCCATTGCCGCGCACCACTTTCCGGT GGGCGGCGGGCAATGCTAGGGGTTAAGAGACCT-TCTCTCCCCGAGATGGAGGCGCCGGGCGG CGCG-GCGGGGGACGCGGAGGAGGAAGTTGATGCCCG-GATCCGCTGGGTTCCATGGTGGCTGC TATGGAATGGTGGAATTGCTTGGATGGCCAC-GAAGGGGATCGACGCCAATTGTTTGGCGACCT CTACGATAGAATCGCGTCGAGTCGGGGTGT-TCTTTCCTGTTATTACTAGAAGTAGTTGAATTTC GTGATTGAACACACAAGGAAGCTTGA-TATCGCGTCGGGGGTGTTCTTTCCTGTTAT-TACTAGA TGTAGTTGGGTTTCGTGATTGAACAC-CTAAGGAAAGGAAGCTTGATAAATGGAAGATAGT-CC AGCAAGTTTTGAAGATGATAGAAAATTT-GAGCGCGTCGTAGTAACTGTCGTCCACGATCACGT CCAGTGTTGTTCATGGCATGGGGGATGGAGTCAG-GATCCTTGAGGCGTCTGCTCCTGTTGCAC TGCT-TCATGCCTTTCCTGCCTTCTAGGATGCTTAAGATG-GTTGCGAAGTCAGGTGCTTGGGAGT TCATGAAGCGGTCATAATCAATTTCGCTCTCTGTAG-TACTTTCTCTGGTGTCTTCCCCGTTGCTT CCTTTTG-GAAGAAAAGCGTCCTTTAGAATCTCTTGAGA-GAGTGCACTTTCTCCCTCTCCTGCCA TCAGTAGTGCCTTTATTTTCGCTTGGTTTCCGCAT-CATCAGGTGGCACTTATAGAAATTATTTT ATGGAG-GAAAAAGCATTGTATGGCATGATAGAAATATCCT-TATGGATAAAACTAGGACACTT GCAAGTGTTCAATGGGAGTCACCTTACCTTTTTT-GCCTACCTGTCTGCATTTCATGAATGGGAT TCCT-TCTCCTGCGCCGGTGCTGTCTTCT-CAAATGGGAAATGGAGGCAAGCATCTGCCCTGTTCC ATGGTGGCAGCCATGGAATGATGGGATTTCTTT-GATGGTCATAAAGGAGATCAAAACCAACG GTTG-GCAATCTCTGCAGGGATGATGAACCAGGCTTG-TAATATCTGTTGCTGATTTCTTTGGAA GACATAACGGCAAGCTTCATGGGGCACGATG-GATTTCAGATGGTTGCTTCAGCCATGTCTCAA GAT-TCAGTTGATGGACCTCAAGTTTCTGGGTGCAGTGC-CACGAGTCTTGGTCAGCCCAAGAGT AAGCGCAGGACTGGTGACAAGGCAAGAGGGGA-GAAGAAGGCACTCAAAGTTAAGATTAACC TTGC-CAGCCCGGCCAAAAAAATTAAGAAAAGTAG-CAAAAAGAAGGGCAAAAAGGGCACTGT TGCTGGCAGGATAGGGAGAAAATGCACTCTCT-CAAGAGATTCTAAAGGGCGCTTTCTTCCAAG AGA-GAGTAAGGGGGGAGACATCGGAGGAAATGCTACA-GAGAGTGAAGTTGATTATGACCGCT TCATGAACTTTCAGGCACCTGACTTCGCTAC-CATCTTAAGTATTTTGAAAGGCTGGAAAGGCA TGAAGCAATGTAACAAGATCAGGCGCCT-CAAGGATCCTGACTTCGTCCCTCTCATGAACGTCA TGAGCAACACTGGATATGTGACCGAGGATGATGGT-CACTATGATGTGCTGAAAGTCTTGATGC ATGCA-GATGGCTGGTCTGCATAGTGATTCAAGCTCT-CAAATCAAAACATTCAGGCCTATGGCC TTGTTGCTAGAACAGTGGTTTCTTCTTTCACCTT-TAAAACTTGATGGACTTTGTTCCATTTATCT TAGAAATTTTGTTGCCCTTGAGTCCGGTGGATATG-TACTGGAGTATGCTATACTGGGTGATTTA ATGGTGA-TAATGTTAAATCTTGATACTAGT-TCAAAAAAAAAAAAAAAAAAAAAAAA (SEQ ID NO. 33), and a phase uniqueness score of 0.959, highly supportive of the predicted RNA transcript having the sequence AGUCCAGCAAGUUUUGAAGAUGAUA-GAAAAUUUGAGCGCGUCGUAGUAACUGUCGUC-CAC GAUCACGUCCAGUGUUGUUCAUG-GCAUGGGGGAUGGAGUCAGGAUCCUUGAGGCG-UCUGC UCCUGUUGCACUGCUUCAUGCCUUUCCUGC-CUUCUAGGAUGCUUAAGAUGGUUGCGAAGUC AGGUGCUUGGGAGUUCAUGAAGCGGUCAUAAU-CAAUUUCGCUCUCUGUAGUACUUUCUCU GGUGU-CUUCCCCGUUGCUUCCUUUUGGAAGAAAAGCGU-CCUUUAGAAUCUCUUGAGAGAG UGCACUUUCUCCCUCUCCUGCCAUCAGUAGUGC-CUUUAUUUUCGCUUGGUUUCCGGCAAAA AGGGCACUGUUGCUGGCAGGAUAGGGA-GAAAAUGCACUCUCUCAAGAGAUUCUAAAGGGC GCUUUCUUCCAAGAGAGAGUAAGGGGGGAGA-CAUCGGAGGAAAUGCUACAGAGAGUGAAG UUGAUUAUGACCGCUUCAUGAACUUUCAGGCAC-CUGACUUCGCUACCAUCUUAAGUAUUU UGAAAGGCUGGAAAGGCAUGAAGCAAUGUAACA-GAUCAGGCGCCUCAAGGAUCCUGACUU CGUCC-CUCUCAUGAACGUCAUGAGCAACACUGGAUAU-GUGACCGAGGAUGAUGGUCACUA UGAUGUGCUGAAA (SEQ ID NO. 34) and containing the sequence and single foldback structure as shown in FIG. 6. FIG. 7A depicts the siRNA abundance in transcripts per quarter million sequences ("tpq") along the entire sequence (about 2 kilobases), and FIG. 7B depicts an expanded view of the siRNA region and the 21-nucleotide phasing of the small RNA abundance from this locus.

As with the phased small RNA locus described in Example 1, the locus having SEQ ID NO. 33 was predicted to transcribe to RNA (SEQ ID NO. 34) forming hybridized RNA independently of an RNA-dependent RNA polymerase and to be cleavable in vivo in phase into multiple small double-stranded RNAs. Unlike trans-acting siRNAs, all of the multiple small double-stranded RNAs derive from the original RNA transcript or plus strand of the precursor, independently of an RNA-dependent RNA polymerase and without a miRNA target site that initiates production of double-stranded RNA. Unlike microRNAs, the locus is cleaved in vivo to multiple abundant phased small RNAs, and (as described below in Example 5), this process requires DCL4 or a DCL4 orthologue and not DCL1.

Data on the phased small RNAs from this locus (SEQ ID NO. 33) are provided in Table 4. The majority of these phased small RNAs were cloned from the rice small RNA libraries, and several were also identified in maize (*Zea mays*) RNA libraries prepared from kernels (32 days after pollination and 39 days after pollination) and root (V9 stage), indicating that a similar phased small RNA locus exists in maize. The transcript (SEQ ID NO. 34) predicted from this locus (SEQ ID NO. 33) also includes 5' flanking sequence AGUCCAGCAAGUUUUGAAGAUGAUA-GAAAAUUUGAGCGCGUCGUAGUAACUGUCG UCCACGA (SEQ ID NO. 66) and 3' flanking sequence GAGGAUGAUGGUCACUAUGAUGUGCUGAAA (SEQ ID NO. 67) as well as a spacer sequence UUUAUUUUCGCUUGGUUUCCGGCAAAAAGGG (SEQ ID NO. 68) located between the 5' and 3' arms of the foldback structure, that includes a 3-nucleotide turn. FIG. 6 depicts the relative position of each small RNA along the 5' and 3' arms of the hybridized RNA (foldback) structure (SEQ ID NO. 34) predicted from the rice locus (SEQ ID NO. 33). Most, but not all, of these small RNAs are 21-mers. The small RNA predicted to be encoded by SEQ ID NO. 59 contains 27 nucleotides, including a large bulge of 8 unpaired nucleotides; modification of this sequence so that this small RNA is closer to two helical turns (about 21 nucleotides) is predicted to result in processing of this small RNA.

Example 5

This example describes a non-limiting embodiment of DNA encoding a transcript that folds into hybridized RNA that is cleaved in phase in vivo into multiple small double-stranded RNAs ("phased small RNAs") for gene suppression, wherein the hybridized RNA is produced independently of an RNA-dependent RNA polymerase. The Os06g21900 phased sRNA locus (described in Example 1 and with the partial structure depicted in FIG. 1) is processed in vivo to multiple phased small RNAs; all of the multiple small double-stranded RNAs derive from the plus strand of the precursor, which distinguishes them from trans-acting

TABLE 4

| | | | | | Abundance (tpq)* | | | | |
|---|---|---|---|---|---|---|---|---|---|
| Location on foldback | sRNA identi-fier | SEQ ID NO. (rice) | SEQ ID NO. (maize)** | Sequence | rice grain | rice seedling | maize 32DAP kernel | maize 39DAP Kernel | maize V9 root |
| 5' arm | 792014 | 35 | | UCACGUCCAGUGUUGUUCAUG | 2.9 | 6.0 | | | |
| 5' arm | *** | 36 | | GCAUGGGGGAUGGAGUCAGGA | | | | | |
| 5' arm | 118041 | 37 | 61 | UCCUUGAGGCGUCUGCUCCUG | 26.1 | 56.8 | 4.2 | | |
| 5' arm | 657519 | 38 | 62 | UUGCACUGCUUCAUGCCUUUC | 798.5 | 817.5 | 23.3 | 0.9 | 1.2 |
| 5' arm | 611711 | 39 | | CUGCCUUCUAGGAUGCUUAAG | 2.0 | 5.0 | | | |
| 5' arm | 1016358 | 40 | | AUGGUUGCGAAGUCAGGUGCU | 143.1 | 86.6 | | | |
| 5' arm | 577487 | 41 | 63 | UGGGAGUUCAUGAAGCGGUCA | 216.2 | 310.7 | 4.2 | | |
| 5' arm | 515019 | 42 | | UAAUCAAUUUCGCUCUCUGUA | 9.4 | 4.0 | | | |
| 5' arm | 803519 | 43 | | GUACUUUCUCUGGUGUCUUCC | 0.6 | | | | |
| 5' arm | * | 44 | | CCGUUGCUUCCUUUUGGAAGA | | | | | |
| 5' arm | 459001 | 45 | | AAAGCGUCCUUUAGAAUCUCU | 1.4 | 1.0 | | | |
| 5' arm | 1119948 | 46 | 64 | UGAGAGAGUGCACUUUCUCCC | 194.0 | 118.5 | 10.6 | | |
| 5' arm | 645846 | 47 | | UCUCCUGCCAUCAGUAGUGCC | 0.8 | 2.0 | | | |
| 3' arm | * | 48 | | CACUGUUGCUGGCAGGAUAGG | | | | | |
| 3' arm | 1147125 | 49 | | GAGAAAAUGCACUCUCUCAAG | 0.3 | | | | |
| 3' arm | 73294 | 50 | | AGAUUCUAAAGGGCGCUUUC | 3.0 | | | | |
| 3' arm | 1002514 | 51 | | UUCCAAGAGAGAGUAAGGGGG | 0.8 | 3.0 | | | |
| 3' arm | 1160057 | 52 | | GAGACAUCGGAGGAAAUGCUA | 0.3 | 2.0 | | | |
| 3' arm | 1287753 | 53 | | CAGAGAGUGAAGUUGAUUAUG | 0.3 | | | | |
| 3' arm | 1396420 | 54 | | ACCGCUUCAUGAACUUUCAGG | 4.9 | 13.9 | | | |
| 3' arm | 1125181 | 55 | 65 | CACCUGACUUCGCUACCAUCU | 8.4 | 5.0 | 2.1 | | |
| 3' arm | 628491 | 56 | | UAAGUAUUUUGAAAGGCUGGA | 2.3 | | | | |
| 3' arm | 985496 | 57 | | AAGGCAUGAAGCAAUGUAACA | | 3.0 | | | |
| 3' arm | * | 58 | | GAUCAGGCGCCUCAAGGAUC | | | | | |
| 3' arm | * | 59 | | CUGACUUCGUCCCUCUCAUGA ACGUCA | | | | | |
| 3' arm | 1249464 | 60 | | UGAGCAACACUGGAUAUGUGA CC | 2.9 | 1.0 | | | |

*"tpq", transcripts per quarter million sequence reads (given as averages of three sequencing runs)

**small RNA also cloned from maize

***predicted from the phased sRNA locus sequence (SEQ ID NO. 33) but not cloned siRNAs. And, unlike microRNAs, the locus contains multiple abundant phased small RNAs. This example provides further characterization of a phased small RNA locus as clearly distinct from canonical microRNAs and trans-acting siRNAs.

The Os06g21900 phased sRNA locus, located on rice Chromosome 6, was further characterized. A 898-nucleotide precursor that mapped to this locus was sequenced from library clone LIB4833-001-R1-N1-G10 and found to have the DNA sequence AATCTTATTCTACATATTTCTATCT-TATATAGAACAACTAGCATAGCTCTCGTTGCCCA-GCCAG GTTGCCCAGCCAGGTTGCCTGGTGCA-CAATGAGAGCTGGCTAGGGCGGACTCATTCTGCT-GTT GGTGCCCAACGATGCTAGCTGCTACTCATACTAGT-GAAGCCTGCCATGGTTCTGAGAAATTTT TGGA-TACTCCGCTGCGTAGATATGCACTAAAAGCTTGTAT-GTTTCGCTGACTACATACTATGG ATATCACCTGTTTGACAAGAGAAGGATTACATAC-CACGATGAAGATGAATTGGAACATGATG CAAGT-GATGTAGCGCCCCATATAGGAGTCACTCAG-GAAAGCACAGAAGAGGGAGAAGATGTA GACGGTGCCCATCCACATGCTGACGCTATTGGCG-GCCTCGGCGTTCTCCTGGTGGAGCACCTG CCT-GAGGAACACCACCAGGCCCACGGCGACGC-CAAAAAATGCAAAGTTGGCCAACACATAGC TCACTGCATCGTCAAGTAGAGCTGCTTAATCACT-GAGGTATATACATTTAGTTCGCCTTCTTCA GCGTT-GCCATGGACCTGGTGATGTTCTTCCGGCGGGTGC-CCCACCAAGAGAACGCCGTGGCCA CCAACAACATCAGCATATGGATGGGCACCATCT-TCATCTTTGCCCTCTTTAGTGCTTTCCGTAG TGAT-TCCTATACGGGGTGCTACTTCACTTGGATCATGTTA-CAATTTATCTTCATCGTGATATAT GCTCCTTCTGTTCTCACATAGGTGATATCTTAAAAT-GTATGAGGCATATATACTTTCTACCTAA TAT-TATAAAGTATATGCCTCTATATAGAT-CAAATAAAGCAGAAAAGTCATTGTTATTACAAAA AAAAAAAAAAAAAAA (SEQ ID NO. 69); the corresponding transcript contained the phased small RNAs (see Example 1) distributed between two regions along the transcript (FIG. 8A). This locus contains two exons (Exons 2 and 3, indicated by the shaded regions) that form a long, imperfect foldback structure containing eight 21-nucleotide phased small double-stranded RNAs, separated by an ~1.2 kB intron (FIG. 8B). No small RNAs were found that match Exon 1, nor was any miRNA target sequence that could initiate a trans-acting siRNA phasing identified (see Allen et al. (2005) *Cell,* 121:207-221; Vaucheret (2005) *Sci. STKE,* 2005, e43; and Yoshikawa et al. (2005) *Genes Dev.,* 19:2164-2175). RNA gel blot analysis of the most abundant phased small RNA confirmed that expression was specific to rice grain (FIG. 8C). Neither of the two most abundant phased small RNAs ("P7", SEQ ID NO. 6, and "P4", SEQ ID NO. 3) was detected in rice seedlings or in other plant species tested.

The phased small RNAs form a novel class of regulatory small RNAs that differ from both canonical microRNAs (miRNAs) and trans-acting siRNAs. The phased small RNAs disclosed herein are to some extent reminiscent of miR163 in *Arabidopsis* in which two phases of siRNAs were sequenced with a single small RNA (miR163 itself) significantly accumulating; see Allen et al. (2004) *Nat. Genet.,* 36:1282-1290; and Kurihara and Watanabe (2004) *Proc. Natl. Acad. Sci. U.S.A,* 101:12753-12758. However, the phased small RNAs clearly differ from miR163 in that multiple abundant phased small RNAs are processed and can be isolated from a single transcript. The phased small RNAs locus is a single, extended, imperfect foldback structure (for example, the loci depicted in FIG. 1, FIG. 6, or FIG. 8B), and therefore is also clearly different from the trans-acting siRNA loci identified in *Arabidopsis*, which require an RNA-dependent RNA polymerase (RDR6) to generate the double-stranded RNA from which the phased siRNAs are processed.

The extended foldback structure of the Os06g21900 phased small RNA locus suggests that this precursor is not processed via the canonical miRNA pathway. The phased nature of the phased small RNAs further indicates that they are the result of processing by DCL4 or a DCL4 orthologue rather than by DCL1. To further confirm that the phased small RNAs disclosed herein are unique and distinct from both canonical microRNAs (miRNAs) and trans-acting siRNAs, the full length cDNA from the Os06g21900 phased small RNA locus was transformed into *Arabidopsis thaliana* Columbia (Col-0) ecotype and mutants dcl1-7 (a DCL1 knock-out) and dcl4-1 (a DCL4 knock-out). RNA was extracted and blots analyzed using probes corresponding to phased small RNAs "P7" (SEQ ID NO. 6), and "P5" (SEQ ID NO. 4), a canonical miRNA (miR173) and a trans-acting siRNA (ta-siR255) (FIG. 8D).

Phased 21-nucleotide small RNAs were highly expressed in transformation events from Col-0 and dcl1-7, but in the dcl4-1 mutant, 21-nucleotide phased sRNAs were absent, with only faint 24-nucleotide small RNAs observed (similar to what was observed for ta-siR255). These data are consistent with the function of DCL4 in processing small RNAs in phase, but, unlike trans-acting siRNAs, no miRNA initiation site was required in the case of the phased small RNA loci disclosed herein. These data also demonstrated that the phased small RNA locus from a monocot crop plant was efficiently processed in a dicot plant. Thus, phased sRNAs are processed through pathways distinct from those of both canonical microRNAs (miRNAs) and trans-acting siRNAs. As described in other Examples disclosed herein, the phased small RNA locus is useful as a template for designing a recombinant DNA construct encoding a transcript that folds into hybridized RNA that is cleaved in phase in vivo into multiple small double-stranded RNAs for gene suppression, or alternatively as a template for designing a recombinant DNA construct including DNA that transcribes to: (a) a first series of contiguous RNA segments, and (b) a second series of contiguous RNA segments, wherein the first series of contiguous RNA segments hybridize in vivo to the second series of RNA segments to form hybridized RNA that is cleaved in phase in vivo into multiple small double-stranded RNAs ("phased small RNAs") for gene suppression.

Example 6

This example describes a non-limiting embodiment of a recombinant DNA construct including DNA that transcribes to: (a) a first series of contiguous RNA segments, and (b) a second series of contiguous RNA segments, wherein the first series of contiguous RNA segments hybridize in vivo to the second series of RNA segments to form hybridized RNA that is cleaved in phase in vivo into multiple small double-stranded RNAs ("phased small RNAs") for gene suppression.

This example provides an embodiment of a recombinant DNA construct including nucleic acid sequences derived from monocot crop plants, that transcribes to an RNA containing a single foldback structure cleavable in vivo and in phase to multiple small double-stranded RNAs for gene suppression, independently of an RNA-dependent RNA polymerase. This example is a recombinant DNA construct designed to suppress multiple target genes. The Os06g21900 phased small RNA locus (see Example 1) was modified to suppress three target genes as follows: nucleotides of the phased small RNAs with the identifiers 1196700 (SEQ ID NO. 3), 1379342 (SEQ ID NO. 6), and 544819 (SEQ ID NO. 7) were replaced, respectively, with nucleotides corresponding to a segment of the GL1, IDA, and LFY genes from *Arabidopsis thaliana*. The resulting sequence was GGTAC-CAATCTTATTCTACATATTTCTATCTTATATA-GAACAACTAGCATAGCTCTCGTTGCCC AGCCAGGT-TGCCCAGCCAGGTTGCCTGGTGCACAATGAGAG-CTGGCTAGGGCGGACTCATTCT GCTGTTGGTGCCCAACGATGCTAGCTGCTACTCAT-ACTAGTGAAGCCTGCCATGGTTCTGAGA AATTTTTGGATACTCCGCTGCGTAGATATG-CACTAAAAGCTTGTATGTTTCGCTGACTACATAC TATGGATATCACCTGTTTGACAAGAGAAGGATTA-CATACCACGATGAAGATGAATTGGAACA TGATG-CAAGTGATGTAGCGCCCCATATAGGAGTCACTCAG-GACTCCACGGTCATTGTGTATCA TGTAGACGGTGCCCATCCACATGCTGACGCTATTG-GCGGCCTTGGTCCTTCATAGAGACCCAA CCTAACA-GTGAACGTACTGTCGCCCCACGGCGACGC-CAAAAAATGCAAAGTTGGCCAACACA TAGCTCACTGCATCGTCAAGTAGAGCTGCTTAAT-CACTGAGGTATATACATTTAGTTCGCCTTC TTCA-GCGTTGCCATGGAGCGACAGAACGTTCACGGT-TAGGTTGTGTCTCTTTGAAGGACCATG GCCACCAACAACATCAGCATATGGATGGGCAC-CATCTTCATGATGAACAATGACGGTGGAGT CCG-TAGTGATTCCTATACGGGGTGCTACTTCACTTGGAT-CATGTTACAATTTATCTTCATCGTG ATATATGCTCCTTCTGTTCTCACATAGGTGATATCT-TAAAATGTATGAGGCATATATACTTTCT ACCTAATAT-TATAAAGTATATGCCTCTATATAGAT-CAAATAAAGCAGAAAAGTCATTGTTATT ACGTTAAC (SEQ ID NO. 70). This sequence was synthesized, subcloned into a dicot binary vector (pMON97890) including a glyphosate resistance selectable marker, and transformed into *Arabidopsis thaliana* using a floral dip technique as described by Clough and Bent (1998), *Plant* 1, 16:735-743. The resulting events are selected using glyphosate, and selected plants are screened for the expected phenotypes, i.e., loss of trichomes by GL1 suppression (Marks and Feldmann (1989) *Plant Cell,* 1:1043-1050), prevention of petal abscission by IDA suppression (Butenko et al. (2003) *Plant Cell,* 15:2296-2307), and flower to leaf conversion by LFY suppression (Schwab et al. (2006) *Plant Cell,* 18:1121-1133).

Example 7

This example describes a non-limiting embodiment of a recombinant DNA construct including DNA that transcribes to: (a) a first series of contiguous RNA segments, and (b) a second series of contiguous RNA segments, wherein the first series of contiguous RNA segments hybridize in vivo to the second series of RNA segments to form hybridized RNA that is cleaved in phase in vivo into multiple small double-stranded RNAs ("phased small RNAs") for gene suppression. More specifically, this example describes a recombinant DNA construct that transcribes to RNA that is cleaved in vivo in phase into phased small RNAs for gene suppression of multiple viruses in plants.

Phased small RNAs were designed to target highly homologous regions of economically important geminiviruses, tospoviruses, and a potexvirus that infect tomato. These viruses include Tomato yellow leaf curl virus (Dominican Republic isolate), Tomato leaf curl New Delhi virus, Tomato severe leaf curl virus, Pepper huasteco yellow vein virus, Pepper golden mosaic virus, Pepino mosaic virus, Tomato spotted wilt virus, Groundnut bud necrosis virus, and *Capsicum chlorosis* virus. Homologous regions allow a limited set of phased small RNAs to control many viruses; additionally, these conserved regions are predicted to be less likely to evolve resistance due to base changes that would impede or prevent suppression by phased small RNAs. Reynolds score, functional asymmetry, and miRNA properties were considered when selecting target sequences for suppression. Multiple phased small RNAs are utilized to improve silencing and prevent resistance.

In this non-limiting example, nucleotide sequences for suppressing multiple viral targets were used to replace native sequences (i.e., segments each of 21 contiguous nucleotides) of the abundant phased small RNAs derived from a scaffold sequence (the Os06g21900 cDNA, SEQ ID NO. 69), with additional nucleotides changed where necessary in order to preserve secondary structure as found in the native precursor transcript. The replacement 21-nucleotide segments included two sequences for suppressing geminiviruses, TGGTACAACGTCATTGATGAC (SEQ ID NO. 71) and TGGACCTTACATGGCCCTTCA (SEQ ID NO. 72), one sequence for suppressing potexviruses, TAATTGT-GCAGCTCATCACCC (SEQ ID NO. 73), and three sequences for suppressing tospoviruses (one for each segment of these tripartite viruses), TAGATGGGAAATATA-GATATC (SEQ ID NO. 74, targetting the tospovirus M segment), TGCTTATATGTATGTTCTGTA (SEQ ID NO. 75, targetting the tospovirus L segment), and TCAAGAGTCTTTGAAAGAAAG (SEQ ID NO. 76, targetting the tospovirus S segment). The replacement segments were incorporated into a DNA sequence encoding a synthetic phased small RNA precursor (i.e., an RNA transcript that is cleaved in vivo in phase into phased small RNAs for gene suppression of multiple viruses in plants), (SEQ ID NO. 77)

AATCTTATTCTACATATTTCTATCTTATATAGAACAACTAGCATA

GCTCTCGTTGCCCAGCCAGGTTGCCCAGCCAGGTTGCCTGGTGCA

CAATGAGAGCTGGCTAGGGCGGACTCATTCTGCTGTTGGTGCCCA

ACGATGCTAGCTGCTACTCATACTAGTGAAGCCTGCCATGGTTCT

GAGAAATTTTTGGATACTCCGCTGCGTAGATATGCACTAAAAGCT

TGTATGTTTCGCTGACTACATACTATGGATATCACCTGTTTGACA

AGAGAAGGATTACATACCACGATGAAGATGAATTGGAACATGTGG

ACCTTACATGGCCCTTCAATATAGGAGTCACTCAGGAgtcatCcG tgacGttAtAccAgacAtcCatatttCccatcCActtTctCttag agacCcttgTgGGtGaTgagtTGcacaGttaCCTGCTTATATGTA

TGTTCTGTACCCACGGCGACGCCAAAAAATGCAAAGTTGGCCAAC

ACATAGCTCACTGCATCGTCAAGTAGAGCTGCTTAATCACTGAGG

TATATACATTTAGTTCGCCTTCTTCAGCGTTGCCATGGAtacaGa aAatacaTatCaGCGGGTAATTGTGCAGCTCATCACCCTCAAGAG

TCTTTGAAAGAAAGTAGATGGGAAATATAGATATCTGGTACAACG

TCATTGATGACTCCGTAGTGATTCCTATACtGaagGgccacgtAa

-continued ggtGcaCATGTTACAATTTATCTTCATCGTGATATATGCTCCTTC

TGTTCTCACATAGGTGATATCTTAAAATGTATGAGGCATATATAC

TTTCTACCTAATATTATAAAGTATATGCCTCTATATAGATCAAAT

AAAGCAGAAAAGTCATTGTTATTAC, where underlined text indicates the location of the replacement 21-nucleotide segments (phased small RNAs) for suppressing viruses, bold text indicates nucleotides in the foldback structure, and lower-case font indicates nucleotides changed to preserve secondary structure as found in the native precursor transcript. FIG. 9A depicts the foldback structure of the transcript of the endogenous Os06g21900 phased small RNA locus (SEQ ID NO. 69); FIG. 9B depicts the foldback structure of the synthetic phased small RNA precursor encoded by SEQ ID NO. 77.

Example 8

This example describes identification of targets of an RNA that is cleaved in vivo in phase into phased small RNAs for gene suppression. More specifically, this example describes identification of targets of phased small RNAs produced from a native phased small RNA locus.

Putative target genes regulated by the phased small RNAs (see Table 4) produced from the locus having SEQ ID NO. 33 were predicted from plant cDNA databases using the miRSite algorithm. miRSite predicts miRNA targets by comparison of sequence similarity between the input miRNA and the target cDNA dataset. The miRNA:target pairs (or analogously, the phased small RNA:target pairs) were scored based on rules established from experimentally validated miRNA targets (Allen et al. (2005) *Cell,* 121:207-221). Briefly, mispairs and single nucleotide gaps were scored as 1, G:U pairs as 0.5, scores for mispairs from bases at positions 2 to 13 (in a sequence of contiguous 21 nucleotides) doubled, and summed along the length of the target. The predicted targets were ranked according to their penalty scores, with scores less than 4.5 considered as putative targets. In the case of conserved miRNAs or phased small RNA, targets present in orthologous genes and locations were given preference. Table 5 provides non-limiting examples of target genes (and the recognition site identified in the target gene's RNA transcript) predicted to be regulated by regulated by phased small RNAs from the locus having SEQ ID NO. 33; the alignment of the phased small RNA and the recognition site is also depicted.

TABLE 5

<table>
<tr><th>phased small RNA SEQ ID NO.</th><th>recognition site SEQ ID NO.</th><th colspan="3">predicted target</th><th>alignment (phased small RNA depicted 3' to 5' above, recognition site depicted 5' to 3' below)</th><th>score</th><th>mismatch</th></tr>
<tr><th></th><th></th><th>target SEQ ID NO</th><th>reference transcript, locus</th><th>annotation</th><th></th><th></th><th></th></tr>
<tr><td>45</td><td>78</td><td>79</td><td>MRT4577_ 6596C.4, TC331707</td><td>Leaf senescence related protein-like (1e-162)</td><td>3' CCCUCUUUCACGUGAGAGAGU 5'<br>| |||||||||| ||||||||<br>gugagaaagugcccucucuca</td><td>3</td><td>2</td></tr>
<tr><td>45</td><td>80</td><td>81</td><td>MRT4577_ 307557C.6, TC321686</td><td>Endosomal protein-like</td><td>3' CCCUCUUUCACGUGAGAGAGU 5'<br>||| |||:||| |||||||||<br>gggcgaaggugaacucucuca</td><td>3.5</td><td>3</td></tr>
<tr><td>45</td><td>82</td><td>83</td><td>MRT4577_ 331298C.1</td><td>DEAD/DEAH box helicase</td><td>3' CCCUCUUUCACGUGAGAGAGU 5'<br>|  ||||:||||||| |||||<br>gccagaaggugcacugucuca</td><td>4.5</td><td>4</td></tr>
<tr><td>37</td><td>84</td><td>85</td><td>MRT4530_ 211478C.3, Os02g39550.3</td><td>Leucine zipper-EF-hand containing transmembrane protein 1; calcium-binding mitochondrial protein Anon-60Da</td><td>3' CUUUCCGUACUUCGUCACGUU 5'<br>|:||||| | |||||||||||<br>ggaaggccu-aagcagugcaa</td><td>3.5</td><td>3</td></tr>
<tr><td>37</td><td>86</td><td>87</td><td>MRT4530_ 191028C, Os07g40750.1</td><td>pentatri-copeptide repeat protein</td><td>3' CUUUCCGUAC-UUCGUCACGUU 5'<br>||||  |||| ||||||||||:<br>gaaauucauggaagcagugcag</td><td>4.5</td><td>4</td></tr>
<tr><td>37</td><td>88</td><td>89</td><td>MRT4577_ 382031C.4, TC363134</td><td>Unknown protein</td><td>3' CUUUCCGUACUUCGUCACGUU 5'<br>||||||| ||||||| |||||<br>ggaaggccugaagca-ugcaa</td><td>3.5</td><td>3</td></tr>
<tr><td>40</td><td>90</td><td>91</td><td>MRT4530_ 165139C.1, Os10g28820</td><td>BTB/POZ domain protein</td><td>3' ACUGGCGAAGUACUUGAGGGU 5'<br>||:|:||| ||||:||||||:<br>uggcugcuacauggacucccg</td><td>4.5</td><td>5</td></tr>
<tr><td>40</td><td>92</td><td>93</td><td>MRT4577_ 124267C.1,</td><td>ABC transporter ATPase</td><td>3' ACUGGCGAAGUACUUGAGGGU 5'<br>|:||  :||||||||||||||<br>aggccuuuucaugaacuccca</td><td>3</td><td>4</td></tr>
</table>

TABLE 5-continued

<table>
<tr><th>phased small RNA SEQ ID NO.</th><th>recog- nition site SEQ ID NO.</th><th colspan="3">predicted target</th><th>alignment (phased small RNA depicted 3' to 5' above, recognition site depicted 5' to 3' below)</th><th>score</th><th>mismatch</th></tr>
<tr><th></th><th></th><th>target SEQ ID NO</th><th>reference transcript, locus</th><th>annotation</th><th></th><th></th><th></th></tr>
<tr><td>39</td><td>94</td><td>95</td><td>MRT4530_ 10744C.5, Os11g30910</td><td>Sulfotransferase domain protein</td><td>3' UCGUGGACUGAAGCGUUGGUA 5'<br>:||:|: | ||||||||||||<br>ggcgcucgccuucgcaaccau</td><td>4.5</td><td>5</td></tr>
<tr><td>39</td><td>96</td><td>97</td><td>MRT4530_ 105985C.3, Os06g13720</td><td>Pyruvate dehydrogenase E1 alpha subunit</td><td>3' UCGUGGACUGAAGCGUUGGUA 5'<br>:|| | ||||||:||||||||<br>ggcccaugacuuugcaaccac</td><td>4.5</td><td>5</td></tr>
</table>

The technique known as RNA ligase-mediated rapid amplification of cDNA 5' ends ("5' RLM-RACE") is used to experimentally validate predicted targets in plants (e.g., rice and maize); see, for example, Kasschau et al. (2003) *Dev. Cell,* 4:205-217, and Llave et al. (2002) *Science,* 297:2053-2056. This approach relies on ligation of an RNA adapter molecule to the 5' end of the cleavage site and is dependent on the 5' phosphate left by RNAase III enzymes including Ago1. The resulting PCR products are sequenced and the relative number of clones which align to the predicted miRNA (or phased small RNA) cleavage site between nucleotides 10 and 11 relative to the miRNA (or phased small RNA) 5' end provide an estimate of miRNA (or phased small RNA) activity. Results from 5' RLM-RACE assays are used to confirm cleavage of a predicted target by any of the phased small RNAs.

Identification and validation of endogenous genes regulated by phased small RNAs from a natively expressed phased small RNA locus is useful, e.g., to eliminate or modify a phased small RNA recognition site in an endogenous gene in order to decouple expression of that gene from regulation by the phased small RNA that natively regulates expression of the gene. For example, the number of mispairs involving bases at positions 2 to 13 (in a phased small RNA recognition site having contiguous 21 nucleotides) can be increased to prevent recognition and cleavage by the phased small RNA.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of providing to a plant at least three small RNAs for gene suppression, comprising expressing in a plant a recombinant DNA construct encoding a single RNA molecule comprising the nucleotide sequence of the plus-strand transcript of an endogenous phased small RNA locus, wherein the plus-strand transcript of the endogenous phased small RNA locus forms a single foldback structure containing at least three endogenous phased small RNAs that are produced by in-phase cleavage by a plant DCL4 ribonuclease, wherein nucleotides of at least one of the endogenous phased small RNAs have been replaced with nucleotides of a target gene, wherein the secondary structure of the single foldback structure comprises a secondary structure of any one of SEQ ID NOs: 17, 34, or 69, and wherein the small RNAs are produced by phased cleavage of the single RNA molecule.

2. The method of claim 1, wherein the target gene is a gene of a plant, a plant pest, or a plant pathogen.

3. The method of claim 1, wherein the target gene is multiple target genes.

4. The method of claim 1, wherein the target gene is at least one gene of an insect pest of a plant, and the recombinant DNA construct further encodes an insecticidal protein.

* * * * *